United States Patent
Kadereit et al.

(10) Patent No.: US 10,806,797 B2
(45) Date of Patent: Oct. 20, 2020

(54) PRODRUGS COMPRISING AN GLP-1/GLUCAGON DUAL AGONIST LINKER HYALURONIC ACID CONJUGATE

(71) Applicant: SANOFI, Paris (FR)

(72) Inventors: Dieter Kadereit, Frankfurt am Main (DE); Michael Wagner, Frankfurt am Main (DE); Thomas Olpp, Frankfurt am Main (DE); Nino Meyer, Frankfurt am Main (DE); Pradeep Dhal, Bridgewater, NJ (US); Paul Konowicz, Bridgewater, NJ (US); Robert Miller, Bridgewater, NJ (US); James Stefano, Bridgewater, NJ (US); Magnus Besev, Bridgewater, NJ (US); Martin Bossart, Frankfurt am Main (DE); Katrin Lorenz, Frankfurt am Main (DE); Torsten Haack, Frankfurt am Main (DE); Andreas Evers, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/574,480

(22) PCT Filed: Jun. 2, 2016

(86) PCT No.: PCT/EP2016/062496
§ 371 (c)(1),
(2) Date: Nov. 15, 2017

(87) PCT Pub. No.: WO2016/193371
PCT Pub. Date: Dec. 8, 2016

(65) Prior Publication Data
US 2018/0289822 A1 Oct. 11, 2018

(30) Foreign Application Priority Data

Jun. 5, 2015 (EP) .................................... 15305858

(51) Int. Cl.
| | |
|---|---|
| *A61K 38/03* | (2006.01) |
| *A61K 47/61* | (2017.01) |
| *A61K 47/69* | (2017.01) |
| *A61P 3/10* | (2006.01) |
| *A61K 9/00* | (2006.01) |
| *A61K 9/10* | (2006.01) |
| *A61K 38/26* | (2006.01) |
| *A61K 47/36* | (2006.01) |

(52) U.S. Cl.
CPC ............ *A61K 47/61* (2017.08); *A61K 9/0019* (2013.01); *A61K 9/10* (2013.01); *A61K 38/26* (2013.01); *A61K 47/36* (2013.01); *A61K 47/6903* (2017.08); *A61P 3/10* (2018.01)

(58) Field of Classification Search
None
See application file for complete search history.

(56) References Cited

U.S. PATENT DOCUMENTS

| | | |
|---|---|---|
| 5,424,286 A | 6/1995 | Eng |
| 5,641,757 A | 6/1997 | Bornstein et al. |
| 6,284,727 B1 | 9/2001 | Kim et al. |
| 6,329,336 B1 | 12/2001 | Bridon et al. |
| 6,344,180 B1 | 2/2002 | Holst et al. |
| 6,410,511 B2 | 6/2002 | L'Italien et al. |
| 6,429,197 B1 | 8/2002 | Coolidge et al. |
| 6,451,974 B1 | 9/2002 | Hansen |
| 6,458,924 B2 | 10/2002 | Knudsen et al. |
| 6,482,799 B1 | 11/2002 | Guseé et al. |
| 6,506,724 B1 | 1/2003 | Hiles et al. |

(Continued)

FOREIGN PATENT DOCUMENTS

| | | |
|---|---|---|
| CN | 101538323 A | 9/2009 |
| CN | 101559041 A | 10/2009 |

(Continued)

OTHER PUBLICATIONS

US 8,729,011 B2, 05/2014, Dimarchi et al. (withdrawn)
Xu, Cancer Res Prey Treat, vol. 42, No. 4, 2013 (Year: 2013).*
Xiaoyu, Progress in Pharmaceutical Sciences, vol. 31, 2007 (Year: 2007).*
Aramadhaka et al. (Apr. 18, 2013) "Connectivity maps for biosimilar drug discovery in venoms: The case of Gila Monster Venom and the anti-diabetes drug Byetta®," Toxicon. 69:160-167.

(Continued)

*Primary Examiner* — Satyanarayana R Gudibande
(74) *Attorney, Agent, or Firm* — Lathrop GPM LLP; James H. Velema, Esq.

(57) ABSTRACT

The present invention relates to a prodrug or a pharmaceutically acceptable salt thereof comprising an GLP-1/Glucagon agonist linker conjugate $Z-L^1-L^2-L-Y-R^{20}$, wherein Y represents an GLP-1/Glucagon agonist moiety; and -L is a linker moiety—by formula (Ia), wherein the dashed line indicates the attachment to one of the amino groups of the GLP-1/Glucagon agonist moiety by forming an amide bond. The invention further relates to pharmaceutical compositions comprising said prodrugs as well as their use as a medicament for treating or preventing diseases or disorders which can be treated by GLP-1/Glucagon agonist.

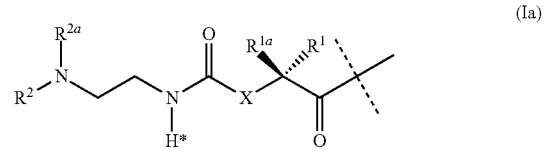

(Ia)

28 Claims, 15 Drawing Sheets

Specification includes a Sequence Listing.

(56) References Cited

U.S. PATENT DOCUMENTS

| | | |
|---|---|---|
| 6,514,500 B1 | 2/2003 | Bridon et al. |
| 6,528,486 B1 | 3/2003 | Larsen et al. |
| 6,579,851 B2 | 6/2003 | Goeke et al. |
| 6,593,295 B2 | 7/2003 | Bridon et al. |
| 6,703,359 B1 | 3/2004 | Young et al. |
| 6,706,689 B2 | 3/2004 | Coolidge et al. |
| 6,723,530 B1 | 4/2004 | Drucker |
| 6,821,949 B2 | 11/2004 | Bridon et al. |
| 6,828,303 B2 | 12/2004 | Kim et al. |
| 6,849,714 B1 | 2/2005 | Bridon et al. |
| 6,858,576 B1 | 2/2005 | Young et al. |
| 6,861,236 B2 | 3/2005 | Moll et al. |
| 6,872,700 B1 | 3/2005 | Young et al. |
| 6,884,579 B2 | 4/2005 | Holst et al. |
| 6,887,470 B1 | 5/2005 | Bridon et al. |
| 6,887,849 B2 | 5/2005 | Bridon et al. |
| 6,894,024 B2 | 5/2005 | Coolidge et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,969,702 B2 | 11/2005 | Bertilsson et al. |
| 6,972,319 B1 | 12/2005 | Pan et al. |
| 6,982,248 B2 | 1/2006 | Coolidge et al. |
| 6,989,366 B2 | 1/2006 | Beeley et al. |
| 6,998,387 B1 | 2/2006 | Goke et al. |
| 7,056,734 B1 | 6/2006 | Egan et al. |
| 7,056,887 B2 | 6/2006 | Coolidge et al. |
| 7,105,489 B2 | 9/2006 | Hathaway et al. |
| 7,105,490 B2 | 9/2006 | Beeley et al. |
| 7,115,569 B2 | 10/2006 | Beeley et al. |
| 7,138,375 B2 | 11/2006 | Beeley et al. |
| 7,138,546 B2 | 11/2006 | Tang |
| 7,141,240 B2 | 11/2006 | Perfetti et al. |
| 7,141,547 B2 | 11/2006 | Rosen et al. |
| 7,144,863 B2 | 12/2006 | Defelippis et al. |
| 7,153,825 B2 | 12/2006 | Young et al. |
| 7,157,555 B1 | 1/2007 | Beeley et al. |
| 7,179,788 B2 | 2/2007 | Defelippis et al. |
| 7,189,690 B2 | 3/2007 | Rosen et al. |
| 7,220,721 B1 | 5/2007 | Beeley et al. |
| 7,223,725 B1 | 5/2007 | Beeley et al. |
| 7,256,253 B2 | 8/2007 | Bridon et al. |
| 7,259,136 B2 | 8/2007 | Hathaway et al. |
| 7,259,233 B2 | 8/2007 | Dodd |
| 7,259,234 B2 | 8/2007 | Bachovchin et al. |
| 7,265,087 B1 | 9/2007 | Göke et al. |
| 7,271,149 B2 | 9/2007 | Glaesner et al. |
| 7,297,761 B2 | 11/2007 | Beeley et al. |
| 7,312,196 B2 | 12/2007 | L'Italien et al. |
| 7,329,646 B2 | 2/2008 | Sun et al. |
| 7,399,489 B2 | 7/2008 | Kolterman et al. |
| 7,399,744 B2 | 7/2008 | Mack et al. |
| 7,407,932 B2 | 8/2008 | Young et al. |
| 7,407,955 B2 | 8/2008 | Himmelsbach et al. |
| 7,414,107 B2 | 8/2008 | Larsen |
| 7,419,952 B2 | 9/2008 | Beeley et al. |
| 7,442,680 B2 | 10/2008 | Young et al. |
| 7,442,682 B2 | 10/2008 | Kitaura et al. |
| 7,452,858 B2 | 11/2008 | Hiles et al. |
| 7,456,254 B2 | 11/2008 | Wright et al. |
| 7,476,652 B2 | 1/2009 | Brunner-Schwarz et al. |
| 7,507,714 B2 | 3/2009 | Pan et al. |
| 7,521,423 B2 | 4/2009 | Young et al. |
| 7,544,657 B2 | 6/2009 | Ebbehøj et al. |
| 7,563,871 B2 | 7/2009 | Wright et al. |
| 7,576,050 B2 | 8/2009 | Greig et al. |
| 7,585,837 B2 | 9/2009 | Shechter et al. |
| 7,592,010 B2 | 9/2009 | Rosen et al. |
| 7,595,293 B2 | 9/2009 | Engelund et al. |
| 7,595,294 B2 | 9/2009 | Nestor |
| 7,608,692 B2 | 10/2009 | Prickett et al. |
| 7,612,176 B2 | 11/2009 | Wright et al. |
| 7,632,806 B2 | 12/2009 | Juul-Mortensen et al. |
| 7,638,299 B2 | 12/2009 | Cho et al. |
| 7,682,356 B2 | 3/2010 | Alessi et al. |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,704,953 B2 | 4/2010 | Herman et al. |
| 7,713,930 B2 | 5/2010 | Brunner-Schwarz et al. |
| 7,723,471 B2 | 5/2010 | Levy et al. |
| 7,741,269 B2 | 6/2010 | Young et al. |
| 7,749,955 B2 | 7/2010 | Hansen et al. |
| 7,772,189 B2 | 8/2010 | Herman et al. |
| 7,790,681 B2 | 9/2010 | Hathaway et al. |
| 7,799,344 B2 | 9/2010 | Oberg |
| 7,799,759 B2 | 9/2010 | Rosen et al. |
| 7,803,404 B2 | 9/2010 | Hokenson et al. |
| 7,829,664 B2 | 11/2010 | Tatake et al. |
| 7,847,079 B2 | 12/2010 | Rosen et al. |
| 7,858,740 B2 | 12/2010 | Beeley et al. |
| 7,867,972 B2 | 1/2011 | Ballance et al. |
| 7,879,028 B2 | 2/2011 | Alessi et al. |
| 7,888,314 B2 | 2/2011 | Hathaway et al. |
| 7,897,560 B2 | 3/2011 | Dorwald et al. |
| 7,906,146 B2 | 3/2011 | Kolterman et al. |
| 7,928,065 B2 | 4/2011 | Young et al. |
| 7,928,186 B2 | 4/2011 | Chang |
| 7,935,786 B2 | 5/2011 | Larsen |
| 7,939,494 B2 | 5/2011 | Khan et al. |
| 7,960,341 B2 | 6/2011 | Hathaway et al. |
| 7,977,306 B2 | 7/2011 | Rosen et al. |
| 7,981,861 B2 | 7/2011 | Coolidge et al. |
| 7,989,585 B2 | 8/2011 | Dodd et al. |
| 7,994,121 B2 | 8/2011 | Bachovchin et al. |
| 7,994,122 B2 | 8/2011 | Riber et al. |
| 8,008,255 B2 | 8/2011 | Ong et al. |
| 8,012,464 B2 | 9/2011 | Rosen et al. |
| 8,026,210 B2 | 9/2011 | Young et al. |
| 8,030,273 B2 | 10/2011 | Lau et al. |
| 8,039,432 B2 | 10/2011 | Bridon et al. |
| 8,057,822 B2 | 11/2011 | Prickett et al. |
| 8,071,539 B2 | 12/2011 | Rosen et al. |
| 8,076,288 B2 | 12/2011 | Levy et al. |
| 8,080,516 B2 | 12/2011 | Bridon et al. |
| 8,084,414 B2 | 12/2011 | Bridon et al. |
| 8,093,206 B2 | 1/2012 | Bridon et al. |
| 8,097,239 B2 | 1/2012 | Johnsson et al. |
| 8,097,586 B2 | 1/2012 | Lv et al. |
| 8,114,632 B2 | 2/2012 | Melarkode et al. |
| 8,114,833 B2 | 2/2012 | Pedersen et al. |
| 8,114,958 B2 | 2/2012 | Soares et al. |
| 8,114,959 B2 | 2/2012 | Juul-Mortensen |
| 8,119,648 B2 | 2/2012 | Himmelsbach et al. |
| 8,143,217 B2 | 3/2012 | Balkan et al. |
| 8,158,579 B2 | 4/2012 | Ballance et al. |
| 8,158,583 B2 | 4/2012 | Knudsen et al. |
| 8,178,495 B2 | 5/2012 | Chilkoti |
| 8,178,541 B2 | 5/2012 | Himmelsbach et al. |
| 8,197,450 B2 | 6/2012 | Glejbol et al. |
| 8,211,439 B2 | 7/2012 | Rosen et al. |
| 8,232,281 B2 | 7/2012 | Dugi et al. |
| 8,236,760 B2 | 8/2012 | Pimentel et al. |
| 8,252,739 B2 | 8/2012 | Rosen et al. |
| 8,263,545 B2 | 9/2012 | Levy et al. |
| 8,263,550 B2 | 9/2012 | Beeley et al. |
| 8,263,554 B2 | 9/2012 | Tatarkiewicz et al. |
| 8,268,781 B2 | 9/2012 | Gotthardt et al. |
| 8,278,272 B2 | 10/2012 | Greig et al. |
| 8,278,420 B2 | 10/2012 | Wang et al. |
| 8,288,338 B2 | 10/2012 | Young et al. |
| 8,293,726 B2 | 10/2012 | Habib |
| 8,293,869 B2 | 10/2012 | Bossard et al. |
| 8,293,871 B2 | 10/2012 | Wright et al. |
| 8,299,024 B2 | 10/2012 | Rabinovitch et al. |
| 8,299,025 B2 | 10/2012 | Alessi et al. |
| 8,329,419 B2 | 12/2012 | Nicolaou et al. |
| 8,329,648 B2 | 12/2012 | Fineman et al. |
| 8,338,368 B2 | 12/2012 | Dimarchi et al. |
| 8,343,910 B2 | 1/2013 | Shechter et al. |
| 8,372,804 B2 | 2/2013 | Richardson et al. |
| 8,377,869 B2 | 2/2013 | Richardson et al. |
| 8,389,473 B2 | 3/2013 | Hathaway et al. |

(56) References Cited

U.S. PATENT DOCUMENTS

| | | |
|---|---|---|
| 8,404,637 B2 | 3/2013 | Levy et al. |
| 8,410,047 B2 | 4/2013 | Bock et al. |
| 8,420,604 B2 | 4/2013 | Hokenson et al. |
| 8,424,518 B2 | 4/2013 | Smutney et al. |
| 8,426,361 B2 | 4/2013 | Levy et al. |
| 8,431,685 B2 | 4/2013 | Wright et al. |
| 8,445,647 B2 | 5/2013 | Prickett et al. |
| 8,450,270 B2 | 5/2013 | Dimarchi et al. |
| 8,454,971 B2 | 6/2013 | Day et al. |
| 8,461,105 B2 | 6/2013 | Wright et al. |
| 8,481,490 B2 | 7/2013 | Tatarkiewicz et al. |
| 8,485,180 B2 | 7/2013 | Smutney et al. |
| 8,497,240 B2 | 7/2013 | Levy et al. |
| 8,499,757 B2 | 8/2013 | Smutney et al. |
| 8,546,327 B2 | 10/2013 | Dimarchi et al. |
| 8,551,946 B2 | 10/2013 | Dimarchi et al. |
| 8,551,947 B2 | 10/2013 | Coolidge et al. |
| 8,557,769 B2 | 10/2013 | Coskun et al. |
| 8,557,771 B2 | 10/2013 | Fan et al. |
| 8,569,481 B2 | 10/2013 | Köster et al. |
| 8,575,097 B2 | 11/2013 | Xu et al. |
| 8,580,919 B2 | 11/2013 | Bossard et al. |
| 8,598,120 B2 | 12/2013 | Soares et al. |
| 8,603,761 B2 | 12/2013 | Nicolaou et al. |
| 8,603,969 B2 | 12/2013 | Levy et al. |
| 8,614,181 B2 | 12/2013 | Juul-Mortensen et al. |
| 8,617,613 B2 | 12/2013 | Wright et al. |
| 8,636,001 B2 | 1/2014 | Smutney et al. |
| 8,641,683 B2 | 2/2014 | Glejbol et al. |
| 8,642,544 B2 | 2/2014 | Alfaro-Lopez et al. |
| 8,664,232 B2 | 3/2014 | Himmelsbach et al. |
| 8,669,228 B2 | 3/2014 | Dimarchi et al. |
| 8,673,927 B2 | 3/2014 | Dugi et al. |
| 8,697,647 B2 | 4/2014 | Levy et al. |
| 8,697,838 B2 | 4/2014 | Dimarchi et al. |
| 8,710,002 B2 | 4/2014 | Rothkopf |
| 8,710,181 B2 | 4/2014 | Christiansen et al. |
| 8,716,221 B2 | 5/2014 | Lv et al. |
| 8,729,018 B2 | 5/2014 | Chilkoti |
| 8,729,019 B2 | 5/2014 | Oberg et al. |
| 8,735,350 B2 | 5/2014 | Shechter et al. |
| 8,748,376 B2 | 6/2014 | Ludvigsen et al. |
| 8,759,290 B2 | 6/2014 | James |
| 8,759,295 B2 | 6/2014 | Ghosh et al. |
| 8,772,232 B2 | 7/2014 | Lau et al. |
| 8,778,872 B2 | 7/2014 | Dimarchi et al. |
| 8,785,396 B2 | 7/2014 | Leone-Bay et al. |
| 8,801,700 B2 | 8/2014 | Alessi et al. |
| 8,809,499 B2 | 8/2014 | Fan et al. |
| 8,816,047 B2 | 8/2014 | Levetan et al. |
| 8,841,255 B2 | 9/2014 | Chilkoti |
| 8,853,157 B2 | 10/2014 | Knudsen et al. |
| 8,853,160 B2 | 10/2014 | Greig et al. |
| 8,877,252 B2 | 11/2014 | Wright et al. |
| 8,877,709 B2 | 11/2014 | Shechter et al. |
| 8,883,449 B2 | 11/2014 | Kjeldsen et al. |
| 8,889,619 B2 | 11/2014 | Bai et al. |
| 8,900,593 B2 | 12/2014 | Day et al. |
| 8,969,288 B2 | 3/2015 | Dimarchi et al. |
| 8,969,294 B2 | 3/2015 | Bianchi et al. |
| 8,980,830 B2 | 3/2015 | Dimarchi et al. |
| 8,981,047 B2 | 3/2015 | Dimarchi et al. |
| 9,018,164 B2 | 4/2015 | Dimarchi et al. |
| 9,181,305 B2 | 11/2015 | Haack et al. |
| 9,365,632 B2 | 6/2016 | Haack et al. |
| 9,457,066 B2 | 10/2016 | Rau et al. |
| 9,670,261 B2 | 6/2017 | Haack et al. |
| 9,694,053 B2 | 7/2017 | Haack et al. |
| 9,745,360 B2 | 8/2017 | Haack et al. |
| 9,750,788 B2 | 9/2017 | Kadereit et al. |
| 9,751,926 B2 | 9/2017 | Kadereit et al. |
| 9,758,561 B2 | 9/2017 | Bossart et al. |
| 9,771,406 B2 | 9/2017 | Bossart et al. |
| 9,775,904 B2 | 10/2017 | Bossart et al. |
| 9,789,165 B2 | 10/2017 | Kadereit et al. |
| 2001/0011071 A1 | 8/2001 | Knudsen et al. |
| 2001/0027180 A1 | 10/2001 | Isaacs |
| 2001/0043934 A1 | 11/2001 | L'Italien et al. |
| 2002/0061838 A1 | 5/2002 | Holmquist et al. |
| 2002/0137666 A1 | 9/2002 | Beeley et al. |
| 2002/0146405 A1 | 10/2002 | Coolidge et al. |
| 2003/0036504 A1 | 2/2003 | Kolterman et al. |
| 2003/0050237 A1 | 3/2003 | Kim et al. |
| 2003/0069182 A1 | 4/2003 | Rinella et al. |
| 2003/0087820 A1 | 5/2003 | Young et al. |
| 2003/0087821 A1 | 5/2003 | Beeley et al. |
| 2003/0092606 A1 | 5/2003 | L'Italien et al. |
| 2003/0119021 A1 | 6/2003 | Koster et al. |
| 2003/0119734 A1 | 6/2003 | Flink et al. |
| 2003/0180287 A1 | 9/2003 | Gombotz et al. |
| 2003/0216287 A1 | 11/2003 | Tang |
| 2003/0220255 A1 | 11/2003 | Knudsen et al. |
| 2004/0023871 A1 | 2/2004 | Hiles et al. |
| 2004/0029784 A1 | 2/2004 | Hathaway |
| 2004/0037826 A1 | 2/2004 | Michelsen et al. |
| 2004/0038865 A1 | 2/2004 | Gelber et al. |
| 2004/0048783 A1 | 3/2004 | Brunner-Schwarz et al. |
| 2004/0097510 A1 | 5/2004 | Himmelsbach et al. |
| 2004/0209255 A1 | 10/2004 | Koster et al. |
| 2004/0209803 A1 | 10/2004 | Baron et al. |
| 2004/0242853 A1 | 12/2004 | Greig et al. |
| 2004/0266670 A9 | 12/2004 | Hiles et al. |
| 2004/0266678 A1 | 12/2004 | Beeley et al. |
| 2004/0266683 A1 | 12/2004 | Hathaway et al. |
| 2004/0266692 A1 | 12/2004 | Young et al. |
| 2005/0009742 A1 | 1/2005 | Bertilsson et al. |
| 2005/0009847 A1 | 1/2005 | Bertilsson et al. |
| 2005/0009988 A1 | 1/2005 | Harris et al. |
| 2005/0043238 A1 | 2/2005 | Young et al. |
| 2005/0059601 A1 | 3/2005 | Beeley et al. |
| 2005/0096276 A1 | 5/2005 | Coolidge et al. |
| 2005/0101537 A1 | 5/2005 | Beeley et al. |
| 2005/0106214 A1 | 5/2005 | Chen |
| 2005/0142152 A1 | 6/2005 | Leshchiner et al. |
| 2005/0143303 A1 | 6/2005 | Quay et al. |
| 2005/0171019 A1 | 8/2005 | Young et al. |
| 2005/0186174 A1 | 8/2005 | Bossard |
| 2005/0197287 A1 | 9/2005 | Mack et al. |
| 2005/0209142 A1 | 9/2005 | Bertilsson et al. |
| 2005/0215469 A1 | 9/2005 | Beeley et al. |
| 2005/0215475 A1 | 9/2005 | Ong et al. |
| 2005/0267034 A1 | 12/2005 | Prickett et al. |
| 2005/0271702 A1 | 12/2005 | Wright et al. |
| 2005/0281879 A1 | 12/2005 | Chen et al. |
| 2006/0003918 A1 | 1/2006 | Kim et al. |
| 2006/0057137 A1 | 3/2006 | Steiness |
| 2006/0069029 A1 | 3/2006 | Kolterman et al. |
| 2006/0073182 A1 | 4/2006 | Wong et al. |
| 2006/0074012 A1 | 4/2006 | Hiles et al. |
| 2006/0079448 A1 | 4/2006 | Bertilsson et al. |
| 2006/0084605 A1 | 4/2006 | Engelund et al. |
| 2006/0094652 A1 | 5/2006 | Levy et al. |
| 2006/0094653 A1 | 5/2006 | Levy et al. |
| 2006/0110423 A1 | 5/2006 | Wright et al. |
| 2006/0135586 A1 | 6/2006 | Kozlowski et al. |
| 2006/0135747 A1 | 6/2006 | Levy et al. |
| 2006/0148713 A1 | 7/2006 | Beeley et al. |
| 2006/0165733 A1 | 7/2006 | Betz et al. |
| 2006/0171920 A1 | 8/2006 | Shechter et al. |
| 2006/0172001 A1 | 8/2006 | Ong et al. |
| 2006/0178304 A1 | 8/2006 | Juul-Mortensen et al. |
| 2006/0183677 A1 | 8/2006 | Young et al. |
| 2006/0183682 A1 | 8/2006 | Juul-Mortensen |
| 2006/0210614 A1 | 9/2006 | Quay et al. |
| 2006/0247167 A1 | 11/2006 | Schlein et al. |
| 2006/0275252 A1 | 12/2006 | Harris et al. |
| 2006/0287221 A1 | 12/2006 | Knudsen et al. |
| 2006/0293232 A1 | 12/2006 | Levy et al. |
| 2006/0293499 A1 | 12/2006 | Bentley et al. |
| 2007/0010424 A1 | 1/2007 | Pedersen et al. |
| 2007/0010656 A1 | 1/2007 | Beeley et al. |
| 2007/0014818 A1 | 1/2007 | Betz et al. |
| 2007/0021336 A1 | 1/2007 | Anderson et al. |
| 2007/0037750 A1 | 2/2007 | Young et al. |

(56) References Cited

U.S. PATENT DOCUMENTS

| | | |
|---|---|---|
| 2007/0049531 A1 | 3/2007 | Knudsen et al. |
| 2007/0059373 A1 | 3/2007 | Oberg |
| 2007/0059374 A1 | 3/2007 | Hokenson et al. |
| 2007/0065469 A1 | 3/2007 | Betz et al. |
| 2007/0066528 A1 | 3/2007 | Beeley et al. |
| 2007/0092482 A1 | 4/2007 | Bossard et al. |
| 2007/0129284 A1 | 6/2007 | Kjeldsen et al. |
| 2007/0166352 A1 | 7/2007 | Wright et al. |
| 2007/0196416 A1 | 8/2007 | Li et al. |
| 2007/0281940 A1 | 12/2007 | Dugi et al. |
| 2008/0071063 A1 | 3/2008 | Allan et al. |
| 2008/0091176 A1 | 4/2008 | Alessi et al. |
| 2008/0119393 A1 | 5/2008 | Beeley et al. |
| 2008/0119569 A1 | 5/2008 | Wright et al. |
| 2008/0125348 A1 | 5/2008 | Wright et al. |
| 2008/0125349 A1 | 5/2008 | Wright et al. |
| 2008/0125351 A1 | 5/2008 | Wright et al. |
| 2008/0125353 A1 | 5/2008 | Hiles et al. |
| 2008/0125361 A1 | 5/2008 | Ludvigsen et al. |
| 2008/0171848 A1 | 7/2008 | Christiansen et al. |
| 2008/0176802 A1 | 7/2008 | Prickett et al. |
| 2008/0176804 A1 | 7/2008 | Mack et al. |
| 2008/0200390 A1 | 8/2008 | Prickett et al. |
| 2008/0213288 A1 | 9/2008 | Michelsen et al. |
| 2008/0214467 A1 | 9/2008 | Prickett et al. |
| 2008/0233053 A1 | 9/2008 | Gross et al. |
| 2008/0249007 A1 | 10/2008 | Lau et al. |
| 2008/0249018 A1 | 10/2008 | Kolterman et al. |
| 2008/0249089 A1 | 10/2008 | Himmelsbach et al. |
| 2008/0255159 A1 | 10/2008 | Himmelsbach et al. |
| 2008/0260838 A1 | 10/2008 | Hokenson et al. |
| 2008/0260847 A1 | 10/2008 | Wright et al. |
| 2008/0274952 A1 | 11/2008 | Soares et al. |
| 2008/0280814 A1 | 11/2008 | Ludvigsen et al. |
| 2008/0300171 A1 | 12/2008 | Balkan et al. |
| 2008/0312157 A1 | 12/2008 | Levy et al. |
| 2008/0318865 A1 | 12/2008 | Juul-Mortensen |
| 2009/0011976 A1 | 1/2009 | Ludvigsen et al. |
| 2009/0018053 A1 | 1/2009 | L'Italien et al. |
| 2009/0029913 A1 | 1/2009 | Beeley et al. |
| 2009/0035253 A1 | 2/2009 | Wright et al. |
| 2009/0036364 A1 | 2/2009 | Levy et al. |
| 2009/0043264 A1 | 2/2009 | Glejbol et al. |
| 2009/0054315 A1 | 2/2009 | Bock et al. |
| 2009/0069226 A1 | 3/2009 | Ong et al. |
| 2009/0082255 A1 | 3/2009 | Brunner-Schwarz et al. |
| 2009/0088369 A1 | 4/2009 | Steiness |
| 2009/0098130 A1 | 4/2009 | Bradshaw et al. |
| 2009/0110647 A1 | 4/2009 | Richardson et al. |
| 2009/0111749 A1 | 4/2009 | Richardson et al. |
| 2009/0137456 A1 | 5/2009 | Dimarchi et al. |
| 2009/0137466 A1 | 5/2009 | Anderson et al. |
| 2009/0148534 A1 | 6/2009 | Yasugi et al. |
| 2009/0163423 A1 | 6/2009 | Young et al. |
| 2009/0170750 A1 | 7/2009 | Kjeldsen et al. |
| 2009/0176704 A1 | 7/2009 | Beeley et al. |
| 2009/0180953 A1 | 7/2009 | Gotthardt et al. |
| 2009/0186817 A1 | 7/2009 | Ghosh et al. |
| 2009/0186819 A1 | 7/2009 | Carrier et al. |
| 2009/0203597 A1 | 8/2009 | Rabinovitch et al. |
| 2009/0203603 A1 | 8/2009 | Baron et al. |
| 2009/0215688 A1 | 8/2009 | Knudsen et al. |
| 2009/0215694 A1 | 8/2009 | Kolterman et al. |
| 2009/0221485 A1 | 9/2009 | James |
| 2009/0226431 A1 | 9/2009 | Habib |
| 2009/0232775 A1 | 9/2009 | Bertilsson et al. |
| 2009/0232807 A1 | 9/2009 | Glaesner et al. |
| 2009/0232891 A1 | 9/2009 | Gelber et al. |
| 2009/0239796 A1 | 9/2009 | Fineman et al. |
| 2009/0247463 A1 | 10/2009 | Wright et al. |
| 2009/0253625 A1 | 10/2009 | Greig et al. |
| 2009/0258818 A1 | 10/2009 | Surolia et al. |
| 2009/0264352 A1 | 10/2009 | Anderson et al. |
| 2009/0280169 A1 | 11/2009 | Leonard |
| 2009/0280170 A1 | 11/2009 | Lee et al. |
| 2009/0286716 A1 | 11/2009 | Knudsen et al. |
| 2009/0286723 A1 | 11/2009 | Levy et al. |
| 2009/0291886 A1 | 11/2009 | Ong et al. |
| 2009/0298757 A1 | 12/2009 | Bloom |
| 2009/0308390 A1 | 12/2009 | Smutney et al. |
| 2009/0308391 A1 | 12/2009 | Smutney et al. |
| 2009/0308392 A1 | 12/2009 | Smutney et al. |
| 2009/0325860 A1 | 12/2009 | Constantino et al. |
| 2010/0009904 A1 | 1/2010 | Lv et al. |
| 2010/0016806 A1 | 1/2010 | Glejbol et al. |
| 2010/0022455 A1 | 1/2010 | Chilkoti |
| 2010/0029554 A1 | 2/2010 | Ghosh et al. |
| 2010/0041867 A1 | 2/2010 | Shechter et al. |
| 2010/0056451 A1 | 3/2010 | Juul-Mortensen et al. |
| 2010/0087365 A1 | 4/2010 | Cherif-Cheikh et al. |
| 2010/0099619 A1 | 4/2010 | Levy et al. |
| 2010/0137558 A1 | 6/2010 | Lee et al. |
| 2010/0152097 A1 | 6/2010 | Wright et al. |
| 2010/0152111 A1 | 6/2010 | Wright et al. |
| 2010/0168011 A1 | 7/2010 | Jennings, Jr. |
| 2010/0173844 A1 | 7/2010 | Ludvigsen et al. |
| 2010/0185184 A1 | 7/2010 | Alessi et al. |
| 2010/0190699 A1 | 7/2010 | Dimarchi et al. |
| 2010/0190701 A1 | 7/2010 | Day et al. |
| 2010/0190715 A1 | 7/2010 | Schlein et al. |
| 2010/0196405 A1 | 8/2010 | Ng et al. |
| 2010/0197565 A1 | 8/2010 | Smutney et al. |
| 2010/0210505 A1 | 8/2010 | Bossard et al. |
| 2010/0216692 A1 | 8/2010 | Brunner-Schwarz et al. |
| 2010/0240586 A1 | 9/2010 | Bao et al. |
| 2010/0247661 A1 | 9/2010 | Hokenson et al. |
| 2010/0261637 A1 | 10/2010 | Spetzler et al. |
| 2010/0278924 A1 | 11/2010 | Oberg et al. |
| 2010/0292172 A1 | 11/2010 | Ghosh et al. |
| 2010/0317056 A1 | 12/2010 | Tiwari et al. |
| 2010/0317576 A1 | 12/2010 | Rothkopf |
| 2010/0331246 A1 | 12/2010 | Dimarchi et al. |
| 2011/0003004 A1 | 1/2011 | Hokenson et al. |
| 2011/0034373 A1 | 2/2011 | Coskun et al. |
| 2011/0034377 A1 | 2/2011 | Young et al. |
| 2011/0059181 A1 | 3/2011 | Hu et al. |
| 2011/0065633 A1 | 3/2011 | Dimarchi et al. |
| 2011/0065731 A1 | 3/2011 | Dugi et al. |
| 2011/0071076 A1 | 3/2011 | Beeley et al. |
| 2011/0091420 A1 | 4/2011 | Liu et al. |
| 2011/0097386 A1 | 4/2011 | Steiner et al. |
| 2011/0097751 A1 | 4/2011 | Nicolaou et al. |
| 2011/0098217 A1 | 4/2011 | Dimarchi et al. |
| 2011/0112277 A1 | 5/2011 | Kozlowski et al. |
| 2011/0118136 A1 | 5/2011 | Köster et al. |
| 2011/0123487 A1 | 5/2011 | Chilkoti |
| 2011/0129522 A1 | 6/2011 | Mevorat-Kaplan et al. |
| 2011/0136737 A1 | 6/2011 | Levy et al. |
| 2011/0152181 A1 | 6/2011 | Alsina-Fernandez et al. |
| 2011/0152182 A1 | 6/2011 | Alsina-Fernandez et al. |
| 2011/0152185 A1 | 6/2011 | Plum et al. |
| 2011/0166062 A1 | 7/2011 | Dimarchi et al. |
| 2011/0166554 A1 | 7/2011 | Alessi et al. |
| 2011/0171178 A1 | 7/2011 | Levetan et al. |
| 2011/0178014 A1 | 7/2011 | Hathaway et al. |
| 2011/0178242 A1 | 7/2011 | Harris et al. |
| 2011/0190200 A1 | 8/2011 | Dimarchi et al. |
| 2011/0195897 A1 | 8/2011 | Kajihara et al. |
| 2011/0230409 A1 | 9/2011 | Knudsen et al. |
| 2011/0237503 A1 | 9/2011 | Alsina-Fernandez et al. |
| 2011/0237510 A1 | 9/2011 | Steiner et al. |
| 2011/0245162 A1 | 10/2011 | Fineman et al. |
| 2011/0257092 A1 | 10/2011 | Dimarchi et al. |
| 2011/0263496 A1 | 10/2011 | Fineman et al. |
| 2011/0281798 A1 | 11/2011 | Kolterman et al. |
| 2011/0288003 A1 | 11/2011 | Dimarchi et al. |
| 2011/0301080 A1 | 12/2011 | Bush et al. |
| 2011/0301081 A1 | 12/2011 | Becker et al. |
| 2011/0301084 A1 | 12/2011 | Lau et al. |
| 2011/0306549 A1 | 12/2011 | Tatarkiewicz et al. |
| 2012/0004168 A1 | 1/2012 | Young et al. |
| 2012/0021978 A1 | 1/2012 | Werner et al. |
| 2012/0040899 A1 | 2/2012 | Costello et al. |
| 2012/0046222 A1 | 2/2012 | Alfaro-Lopez et al. |

(56) References Cited

U.S. PATENT DOCUMENTS

| | | |
|---|---|---|
| 2012/0071510 A1 | 3/2012 | Leone-Bay et al. |
| 2012/0071817 A1 | 3/2012 | Ward et al. |
| 2012/0094356 A1 | 4/2012 | Chung et al. |
| 2012/0100070 A1 | 4/2012 | Ahn et al. |
| 2012/0122783 A1 | 5/2012 | Dimarchi et al. |
| 2012/0135922 A1 | 5/2012 | Prickett et al. |
| 2012/0136318 A1 | 5/2012 | Lanin et al. |
| 2012/0148586 A1 | 6/2012 | Chou et al. |
| 2012/0149639 A1 | 6/2012 | Balkan et al. |
| 2012/0157932 A1 | 6/2012 | Glejbol et al. |
| 2012/0172295 A1 | 7/2012 | Dimarchi et al. |
| 2012/0177697 A1 | 7/2012 | Chen |
| 2012/0196795 A1 | 8/2012 | Xu et al. |
| 2012/0196796 A1 | 8/2012 | Soares et al. |
| 2012/0196802 A1 | 8/2012 | Lv et al. |
| 2012/0196804 A1 | 8/2012 | Dimarchi et al. |
| 2012/0208755 A1 | 8/2012 | Leung et al. |
| 2012/0208831 A1 | 8/2012 | Himmelsbach et al. |
| 2012/0209213 A1 | 8/2012 | Theucher |
| 2012/0225810 A1 | 9/2012 | Pedersen et al. |
| 2012/0231022 A1 | 9/2012 | Bass et al. |
| 2012/0238493 A1 | 9/2012 | Dimarchi et al. |
| 2012/0238496 A1 | 9/2012 | Fan et al. |
| 2012/0253023 A1 | 10/2012 | Levy et al. |
| 2012/0258912 A1 | 10/2012 | Bentley et al. |
| 2012/0258985 A1 | 10/2012 | Kozlowski et al. |
| 2012/0264683 A1 | 10/2012 | Coskun et al. |
| 2012/0264684 A1 | 10/2012 | Kajihara et al. |
| 2012/0276098 A1 | 11/2012 | Hamilton et al. |
| 2012/0277154 A1 | 11/2012 | Fan et al. |
| 2012/0283179 A1 | 11/2012 | Brunner-Schwarz et al. |
| 2012/0294855 A1 | 11/2012 | Van Cauter et al. |
| 2012/0295836 A1 | 11/2012 | Knudsen et al. |
| 2012/0295846 A1 | 11/2012 | Hagendorf et al. |
| 2012/0295850 A1 | 11/2012 | Tatarkiewicz et al. |
| 2012/0302501 A1 | 11/2012 | Coolidge et al. |
| 2012/0309975 A1 | 12/2012 | Colca et al. |
| 2012/0316108 A1 | 12/2012 | Chen et al. |
| 2012/0316138 A1 | 12/2012 | Colca et al. |
| 2012/0322725 A1 | 12/2012 | Dimarchi et al. |
| 2012/0322728 A1 | 12/2012 | Colca et al. |
| 2012/0329715 A1 | 12/2012 | Greig et al. |
| 2013/0005664 A1 | 1/2013 | Chilkoti |
| 2013/0023470 A1 | 1/2013 | Young et al. |
| 2013/0023471 A1 | 1/2013 | Rabinovitch et al. |
| 2013/0046245 A1 | 2/2013 | Raab et al. |
| 2013/0053350 A1 | 2/2013 | Colca et al. |
| 2013/0065826 A1 | 3/2013 | Soula et al. |
| 2013/0079277 A1 | 3/2013 | Chilkoti |
| 2013/0079278 A1 | 3/2013 | Lau et al. |
| 2013/0084277 A1 | 4/2013 | Arnold et al. |
| 2013/0085099 A1 | 4/2013 | Chilkoti |
| 2013/0085104 A1 | 4/2013 | Chilkoti |
| 2013/0089878 A1 | 4/2013 | Nicolaou et al. |
| 2013/0090286 A1 | 4/2013 | Dimarchi et al. |
| 2013/0095037 A1 | 4/2013 | Gotthardt et al. |
| 2013/0096258 A1 | 4/2013 | Bossard et al. |
| 2013/0104887 A1 | 5/2013 | Smutney et al. |
| 2013/0116172 A1 | 5/2013 | Dimarchi et al. |
| 2013/0116175 A1 | 5/2013 | Shechter et al. |
| 2013/0118491 A1 | 5/2013 | Richardson et al. |
| 2013/0123178 A1 | 5/2013 | Dimarchi et al. |
| 2013/0123462 A1 | 5/2013 | Dimarchi et al. |
| 2013/0125886 A1 | 5/2013 | Richardson et al. |
| 2013/0130977 A1 | 5/2013 | Wright et al. |
| 2013/0137631 A1 | 5/2013 | Levy et al. |
| 2013/0137645 A1 | 5/2013 | Rosendahl |
| 2013/0142795 A1 | 6/2013 | Bai et al. |
| 2013/0156849 A1 | 6/2013 | De Fougerolles et al. |
| 2013/0157934 A1 | 6/2013 | Dimarchi et al. |
| 2013/0157953 A1 | 6/2013 | Petersen et al. |
| 2013/0164310 A1 | 6/2013 | Annathur et al. |
| 2013/0165370 A1 | 6/2013 | Bock et al. |
| 2013/0165379 A1 | 6/2013 | Kolterman et al. |
| 2013/0172274 A1 | 7/2013 | Chilkoti |
| 2013/0178411 A1 | 7/2013 | Chilkoti |
| 2013/0178415 A1 | 7/2013 | Soula et al. |
| 2013/0184203 A1 | 7/2013 | Alfaro-Lopez et al. |
| 2013/0184443 A1 | 7/2013 | Bentley et al. |
| 2013/0189328 A1 | 7/2013 | Cleeman et al. |
| 2013/0189365 A1 | 7/2013 | Hokenson et al. |
| 2013/0199527 A1 | 8/2013 | Smutney et al. |
| 2013/0203660 A1 | 8/2013 | Day et al. |
| 2013/0209586 A1 | 8/2013 | Hathaway et al. |
| 2013/0217622 A1 | 8/2013 | Lee et al. |
| 2013/0236974 A1 | 9/2013 | De Fougerolles |
| 2013/0237592 A1 | 9/2013 | De Fougerolles et al. |
| 2013/0237593 A1 | 9/2013 | De Fougerolles et al. |
| 2013/0237594 A1 | 9/2013 | De Fougerolles et al. |
| 2013/0244278 A1 | 9/2013 | De Fougerolles et al. |
| 2013/0244279 A1 | 9/2013 | De Fougerolles et al. |
| 2013/0245104 A1 | 9/2013 | De Fougerolles et al. |
| 2013/0245105 A1 | 9/2013 | De Fougerolles et al. |
| 2013/0245106 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0253043 A1 | 9/2013 | De Fougerolles et al. |
| 2013/0259923 A1 | 10/2013 | Bancel et al. |
| 2013/0259924 A1 | 10/2013 | Bancel et al. |
| 2013/0266640 A1 | 10/2013 | De Fougerolles et al. |
| 2013/0280206 A1 | 10/2013 | Kozlowski et al. |
| 2013/0281368 A1 | 10/2013 | Bilsky et al. |
| 2013/0281374 A1 | 10/2013 | Levy et al. |
| 2013/0284912 A1 | 10/2013 | Vogel et al. |
| 2013/0288958 A1 | 10/2013 | Lau et al. |
| 2013/0289241 A1 | 10/2013 | Bai et al. |
| 2013/0291866 A1 | 11/2013 | Smutney et al. |
| 2013/0291867 A1 | 11/2013 | Smutney et al. |
| 2013/0296236 A1 | 11/2013 | Silvestre et al. |
| 2013/0303442 A1 | 11/2013 | Levy et al. |
| 2013/0310310 A1 | 11/2013 | Liu et al. |
| 2013/0310538 A1 | 11/2013 | Chilkoti |
| 2013/0331322 A1 | 12/2013 | Young et al. |
| 2013/0336893 A1 | 12/2013 | Haack et al. |
| 2013/0338065 A1 | 12/2013 | Smutney et al. |
| 2013/0338071 A1 | 12/2013 | Knudsen et al. |
| 2013/0345134 A1 | 12/2013 | Sauerberg et al. |
| 2014/0007873 A1 | 1/2014 | Smutney et al. |
| 2014/0011732 A1 | 1/2014 | Spetzler et al. |
| 2014/0014106 A1 | 1/2014 | Smutney et al. |
| 2014/0017208 A1 | 1/2014 | Osei |
| 2014/0031281 A1 | 1/2014 | Wright et al. |
| 2014/0038891 A1 | 2/2014 | Prickett et al. |
| 2014/0056924 A1 | 2/2014 | Van Cauter |
| 2014/0066368 A1 | 3/2014 | Mack et al. |
| 2014/0083421 A1 | 3/2014 | Smutney et al. |
| 2014/0088003 A1 | 3/2014 | Wright et al. |
| 2014/0100156 A1 | 4/2014 | Haack et al. |
| 2014/0107019 A1 | 4/2014 | Erickson et al. |
| 2014/0107021 A1 | 4/2014 | Dimarchi et al. |
| 2014/0120120 A1 | 5/2014 | Woo et al. |
| 2014/0121352 A1 | 5/2014 | Shechter et al. |
| 2014/0128318 A1 | 5/2014 | Jung et al. |
| 2014/0128604 A1 | 5/2014 | Himmelsbach et al. |
| 2014/0135348 A1 | 5/2014 | Dugi et al. |
| 2014/0141467 A1 | 5/2014 | Tiwari et al. |
| 2014/0142037 A1 | 5/2014 | Yue |
| 2014/0162943 A1 | 6/2014 | Alfaro-Lopez et al. |
| 2014/0187483 A1 | 7/2014 | Steiness |
| 2014/0200183 A1 | 7/2014 | Hathaway et al. |
| 2014/0206608 A1 | 7/2014 | Haack et al. |
| 2014/0206609 A1 | 7/2014 | Haack et al. |
| 2014/0206613 A1 | 7/2014 | Rabinovitch et al. |
| 2014/0206615 A1 | 7/2014 | Knudsen et al. |
| 2014/0212419 A1 | 7/2014 | Dimarchi et al. |
| 2014/0212440 A1 | 7/2014 | Jung et al. |
| 2014/0213513 A1 | 7/2014 | Haack et al. |
| 2014/0213516 A1 | 7/2014 | Chilkoti |
| 2014/0220029 A1 | 8/2014 | Michelsen et al. |
| 2014/0220134 A1 | 8/2014 | Zierhut et al. |
| 2014/0221280 A1 | 8/2014 | Bloom |
| 2014/0221281 A1 | 8/2014 | Haack et al. |
| 2014/0221282 A1 | 8/2014 | Sun et al. |
| 2014/0227264 A1 | 8/2014 | Hamilton et al. |

(56) References Cited

U.S. PATENT DOCUMENTS

| | | |
|---|---|---|
| 2014/0235535 A1 | 8/2014 | Erickson et al. |
| 2014/0243263 A1 | 8/2014 | Rothkopf |
| 2014/0249299 A1 | 9/2014 | Levy et al. |
| 2014/0308358 A1 | 10/2014 | Oberg et al. |
| 2014/0309168 A1 | 10/2014 | Rosendahl |
| 2014/0315953 A1 | 10/2014 | Leone-Bay et al. |
| 2015/0011467 A1 | 1/2015 | Bloom et al. |
| 2015/0126440 A1 | 5/2015 | Day et al. |
| 2015/0164995 A1 | 6/2015 | Kadereit et al. |
| 2015/0164996 A1 | 6/2015 | Kadereit et al. |
| 2015/0164997 A1 | 6/2015 | Haack et al. |
| 2015/0166625 A1* | 6/2015 | Haack .................... A61K 38/22 424/9.3 |
| 2015/0166627 A1 | 6/2015 | Kadereit et al. |
| 2015/0216941 A1 | 8/2015 | Bley et al. |
| 2015/0232527 A1 | 8/2015 | Gong et al. |
| 2015/0315260 A1 | 11/2015 | Bossart et al. |
| 2015/0322128 A1 | 11/2015 | Bossart et al. |
| 2015/0322129 A1 | 11/2015 | Bossart et al. |
| 2015/0368311 A1 | 12/2015 | Haack et al. |
| 2016/0168225 A1 | 6/2016 | Haack et al. |
| 2016/0220643 A1 | 8/2016 | Haack et al. |
| 2016/0235855 A1 | 8/2016 | Xiong et al. |
| 2017/0008944 A1 | 1/2017 | Bossart et al. |
| 2017/0216406 A1 | 8/2017 | Haack et al. |
| 2018/0154005 A1 | 6/2018 | Kadereit et al. |

FOREIGN PATENT DOCUMENTS

| | | |
|---|---|---|
| CN | 101663317 A | 3/2010 |
| CN | 101798588 A | 8/2010 |
| CN | 101870728 A | 10/2010 |
| CN | 101601646 B | 3/2011 |
| CN | 102100906 A | 6/2011 |
| CN | 102363633 A | 2/2012 |
| CN | 102421796 A | 4/2012 |
| CN | 101444618 B | 6/2012 |
| CN | 102532301 A | 7/2012 |
| CN | 102649947 A | 8/2012 |
| CN | 102816244 A | 12/2012 |
| CN | 102827270 A | 12/2012 |
| CN | 101670096 B | 1/2013 |
| CN | 103304660 A | 9/2013 |
| CN | 103421094 A | 12/2013 |
| CN | 103665148 A | 3/2014 |
| CN | 103833841 A | 6/2014 |
| CN | 103908657 A | 7/2014 |
| CN | 102766204 B | 10/2014 |
| CN | 104926934 A | 9/2015 |
| EP | 1 140 145 B1 | 7/2005 |
| EP | 0 619 322 B1 | 12/2005 |
| EP | 1 609 478 A1 | 12/2005 |
| EP | 1 143 989 B1 | 12/2006 |
| EP | 1 790 665 A1 | 5/2007 |
| EP | 1 658 856 B1 | 3/2010 |
| EP | 1 684 793 B1 | 9/2011 |
| EP | 1 633 391 B1 | 10/2011 |
| EP | 2 387 989 A2 | 11/2011 |
| EP | 1 633 390 B1 | 1/2012 |
| EP | 2 494 983 A1 | 9/2012 |
| EP | 2 626 368 A2 | 8/2013 |
| EP | 2 664 374 A1 | 11/2013 |
| EP | 1 817 048 B1 | 2/2014 |
| EP | 2 769 990 A2 | 8/2014 |
| JP | 2014-227368 A | 12/2014 |
| KR | 10-2012-0137271 A | 12/2012 |
| KR | 10-2012-0139579 A | 12/2012 |
| KR | 10-2014-0018462 A | 2/2014 |
| KR | 10-2014-0058104 A | 5/2014 |
| KR | 10-2014-0058387 A | 5/2014 |
| KR | 10-2014-0130659 A | 11/2014 |
| KR | 10-2014-0133493 A | 11/2014 |
| RU | 2009121626 A | 2/2011 |
| WO | 1996/019229 A1 | 6/1996 |
| WO | 1998/005351 A1 | 2/1998 |
| WO | 1998/008871 A1 | 3/1998 |
| WO | 1998/030231 A1 | 7/1998 |
| WO | 1999/007404 A1 | 2/1999 |
| WO | 1999/025727 A2 | 5/1999 |
| WO | 1999/025728 A1 | 5/1999 |
| WO | 1999/034822 A1 | 7/1999 |
| WO | 1999/043708 A1 | 9/1999 |
| WO | 1999/047160 A1 | 9/1999 |
| WO | 1999/064061 A1 | 12/1999 |
| WO | 2000/015224 A1 | 3/2000 |
| WO | 2000/037098 A1 | 6/2000 |
| WO | 2000/041546 A2 | 7/2000 |
| WO | 2000/041548 A2 | 7/2000 |
| WO | 2000/055119 A1 | 9/2000 |
| WO | 2000/066629 A1 | 11/2000 |
| WO | 2000/071175 A1 | 11/2000 |
| WO | 2000/073331 A2 | 12/2000 |
| WO | 2001/051078 A1 | 7/2001 |
| WO | 2002/016309 A1 | 2/2002 |
| WO | 2002/034285 A2 | 5/2002 |
| WO | 2002/067989 A1 | 9/2002 |
| WO | 2003/011892 A2 | 2/2003 |
| WO | 2003/020201 A2 | 3/2003 |
| WO | 2003/061362 A2 | 7/2003 |
| WO | 2003/077851 A2 | 9/2003 |
| WO | 2003/084563 A1 | 10/2003 |
| WO | 2003/092581 A2 | 11/2003 |
| WO | 2003/099314 A1 | 12/2003 |
| WO | 2003/101395 A2 | 12/2003 |
| WO | 2003/105888 A1 | 12/2003 |
| WO | 2003/105897 A1 | 12/2003 |
| WO | 2004/004779 A1 | 1/2004 |
| WO | 2004/004780 A1 | 1/2004 |
| WO | 2004/004781 A1 | 1/2004 |
| WO | 2004/005342 A1 | 1/2004 |
| WO | 2004/012672 A2 | 2/2004 |
| WO | 2004/018468 A2 | 3/2004 |
| WO | 2004/035623 A2 | 4/2004 |
| WO | 2004/045592 A2 | 6/2004 |
| WO | 2004/056313 A2 | 7/2004 |
| WO | 2004/056317 A2 | 7/2004 |
| WO | 2004/089280 A2 | 10/2004 |
| WO | 2004/089985 A1 | 10/2004 |
| WO | 2004/105781 A2 | 12/2004 |
| WO | 2004/105790 A1 | 12/2004 |
| WO | 2005/000222 A2 | 1/2005 |
| WO | 2005/000360 A2 | 1/2005 |
| WO | 2005/012347 A2 | 2/2005 |
| WO | 2005/021022 A2 | 3/2005 |
| WO | 2005/046716 A1 | 5/2005 |
| WO | 2005/048989 A1 | 6/2005 |
| WO | 2005/049061 A2 | 6/2005 |
| WO | 2005/049069 A1 | 6/2005 |
| WO | 2005/054291 A1 | 6/2005 |
| WO | 2005/077072 A2 | 8/2005 |
| WO | 2005/077094 A2 | 8/2005 |
| WO | 2005/081619 A2 | 9/2005 |
| WO | 2005/102293 A1 | 11/2005 |
| WO | 2005/110425 A1 | 11/2005 |
| WO | 2005/115437 A2 | 12/2005 |
| WO | 2005/117584 A2 | 12/2005 |
| WO | 2005/120492 A1 | 12/2005 |
| WO | 2006/017688 A2 | 2/2006 |
| WO | 2006/024275 A2 | 3/2006 |
| WO | 2006/024631 A2 | 3/2006 |
| WO | 2006/029634 A2 | 3/2006 |
| WO | 2006/037811 A2 | 4/2006 |
| WO | 2006/044531 A2 | 4/2006 |
| WO | 2006/051103 A2 | 5/2006 |
| WO | 2006/051110 A2 | 5/2006 |
| WO | 2006/066024 A2 | 6/2006 |
| WO | 2006/069388 A2 | 6/2006 |
| WO | 2006/073890 A2 | 7/2006 |
| WO | 2006/074600 A1 | 7/2006 |
| WO | 2006/083254 A1 | 8/2006 |
| WO | 2006/086769 A2 | 8/2006 |
| WO | 2006/097535 A2 | 9/2006 |
| WO | 2006/110887 A2 | 10/2006 |

(56) References Cited

FOREIGN PATENT DOCUMENTS

| | | |
|---|---|---|
| WO | 2006/114396 A1 | 11/2006 |
| WO | 2006/125763 A1 | 11/2006 |
| WO | 2006/134340 A2 | 12/2006 |
| WO | 2006/138572 A2 | 12/2006 |
| WO | 2007/019331 A2 | 2/2007 |
| WO | 2007/022123 A2 | 3/2007 |
| WO | 2007/024700 A2 | 3/2007 |
| WO | 2007/033316 A2 | 3/2007 |
| WO | 2007/033372 A2 | 3/2007 |
| WO | 2007/035665 A1 | 3/2007 |
| WO | 2007/047834 A2 | 4/2007 |
| WO | 2007/047922 A2 | 4/2007 |
| WO | 2007/056362 A2 | 5/2007 |
| WO | 2007/064691 A1 | 6/2007 |
| WO | 2007/065156 A2 | 6/2007 |
| WO | 2007/067964 A2 | 6/2007 |
| WO | 2007/075534 A2 | 7/2007 |
| WO | 2007/109354 A2 | 9/2007 |
| WO | 2007/120899 A2 | 10/2007 |
| WO | 2007/121411 A2 | 10/2007 |
| WO | 2007/128761 A2 | 11/2007 |
| WO | 2007/133778 A2 | 11/2007 |
| WO | 2007/139941 A2 | 12/2007 |
| WO | 2007/140284 A2 | 12/2007 |
| WO | 2008/021133 A2 | 2/2008 |
| WO | 2008/021560 A2 | 2/2008 |
| WO | 2008/023050 A1 | 2/2008 |
| WO | 2008/038147 A2 | 4/2008 |
| WO | 2008/058461 A1 | 5/2008 |
| WO | 2008/071972 A1 | 6/2008 |
| WO | 2008/073448 A2 | 6/2008 |
| WO | 2008/081418 A1 | 7/2008 |
| WO | 2008/086086 A2 | 7/2008 |
| WO | 2008/098212 A2 | 8/2008 |
| WO | 2008/101017 A2 | 8/2008 |
| WO | 2008/148839 A2 | 12/2008 |
| WO | 2008/152403 A1 | 12/2008 |
| WO | 2009/020802 A2 | 2/2009 |
| WO | 2009/024015 A1 | 2/2009 |
| WO | 2009/029847 A1 | 3/2009 |
| WO | 2009/030771 A1 | 3/2009 |
| WO | 2009/035540 A2 | 3/2009 |
| WO | 2009/055740 A2 | 4/2009 |
| WO | 2009/055742 A2 | 4/2009 |
| WO | 2009/058662 A2 | 5/2009 |
| WO | 2009/058734 A1 | 5/2009 |
| WO | 2009/063072 A2 | 5/2009 |
| WO | 2009/067268 A1 | 5/2009 |
| WO | 2009/095479 A2 | 8/2009 |
| WO | 2009/099763 A1 | 8/2009 |
| WO | WO2009095479 * | 8/2009 |
| WO | WO-2009095479 A2 * | 8/2009 ........... A61K 31/553 |
| WO | 2009/113099 A2 | 9/2009 |
| WO | 2009/137078 A1 | 11/2009 |
| WO | 2009/137080 A1 | 11/2009 |
| WO | 2009/143014 A1 | 11/2009 |
| WO | 2009/143285 A2 | 11/2009 |
| WO | 2009/152477 A2 | 12/2009 |
| WO | 2009/153960 A1 | 12/2009 |
| WO | 2009/155257 A1 | 12/2009 |
| WO | 2009/155258 A2 | 12/2009 |
| WO | 2009/158704 A2 | 12/2009 |
| WO | 2010/011439 A2 | 1/2010 |
| WO | 2010/013012 A2 | 2/2010 |
| WO | 2010/043566 A2 | 4/2010 |
| WO | 2010/070251 A1 | 6/2010 |
| WO | 2010/070252 A1 | 6/2010 |
| WO | 2010/070253 A1 | 6/2010 |
| WO | 2010/070255 A1 | 6/2010 |
| WO | 2010/071807 A1 | 6/2010 |
| WO | 2010/096052 A1 | 8/2010 |
| WO | 2010/096142 A1 | 8/2010 |
| WO | 2010/102148 A2 | 9/2010 |
| WO | 2010/120476 A2 | 10/2010 |
| WO | 2010/121559 A1 | 10/2010 |
| WO | 2010/123290 A2 | 10/2010 |
| WO | 2010/133675 A1 | 11/2010 |
| WO | 2010/133676 A1 | 11/2010 |
| WO | 2010/138671 A1 | 12/2010 |
| WO | 2010/142665 A1 | 12/2010 |
| WO | 2010/148089 A1 | 12/2010 |
| WO | 2011/000095 A1 | 1/2011 |
| WO | 2011/006497 A1 | 1/2011 |
| WO | 2011/011675 A1 | 1/2011 |
| WO | 2011/012718 A1 | 2/2011 |
| WO | 2011/020319 A1 | 2/2011 |
| WO | 2011/020320 A1 | 2/2011 |
| WO | 2011/024110 A2 | 3/2011 |
| WO | 2011/039096 A1 | 4/2011 |
| WO | 2011/049713 A2 | 4/2011 |
| WO | 2011/052523 A1 | 5/2011 |
| WO | 2011/056713 A2 | 5/2011 |
| WO | 2011/058082 A1 | 5/2011 |
| WO | 2011/058083 A1 | 5/2011 |
| WO | 2011/075393 A1 | 6/2011 |
| WO | 2011/075514 A1 | 6/2011 |
| WO | 2011/075623 A1 | 6/2011 |
| WO | 2011/080103 A1 | 7/2011 |
| WO | 2011/084453 A1 | 7/2011 |
| WO | 2011/084456 A1 | 7/2011 |
| WO | 2011/084459 A1 | 7/2011 |
| WO | 2011/087671 A1 | 7/2011 |
| WO | 2011/087672 A1 | 7/2011 |
| WO | 2011/088837 A1 | 7/2011 |
| WO | 2011/094337 A1 | 8/2011 |
| WO | 2011/109784 A1 | 9/2011 |
| WO | 2011/117415 A1 | 9/2011 |
| WO | 2011/117416 A1 | 9/2011 |
| WO | 2011/119657 A1 | 9/2011 |
| WO | 2011/143208 A1 | 11/2011 |
| WO | 2011/143209 A1 | 11/2011 |
| WO | 2011/144751 A1 | 11/2011 |
| WO | 2011/153965 A1 | 12/2011 |
| WO | 2011/156407 A2 | 12/2011 |
| WO | 2011/160630 A2 | 12/2011 |
| WO | 2011/162830 A2 | 12/2011 |
| WO | 2011/163012 A2 | 12/2011 |
| WO | 2011/163272 A2 | 12/2011 |
| WO | 2011/163473 A1 | 12/2011 |
| WO | 2012/012352 A1 | 1/2012 |
| WO | 2012/012460 A1 | 1/2012 |
| WO | 2012/015975 A2 | 2/2012 |
| WO | 2012/031518 A1 | 3/2012 |
| WO | 2012/035139 A1 | 3/2012 |
| WO | 2012/050923 A2 | 4/2012 |
| WO | 2012/059762 A1 | 5/2012 |
| WO | 2012/064892 A1 | 5/2012 |
| WO | 2012/080471 A1 | 6/2012 |
| WO | 2012/088116 A2 | 6/2012 |
| WO | 2012/088157 A2 | 6/2012 |
| WO | 2012/122535 A2 | 9/2012 |
| WO | 2012/130015 A1 | 10/2012 |
| WO | 2012/138941 A1 | 10/2012 |
| WO | 2012/140647 A2 | 10/2012 |
| WO | 2012/150503 A2 | 11/2012 |
| WO | 2012/158965 A2 | 11/2012 |
| WO | 2012/162547 A2 | 11/2012 |
| WO | 2012/167744 A1 | 12/2012 |
| WO | 2012/169798 A2 | 12/2012 |
| WO | 2012/173422 A1 | 12/2012 |
| WO | 2012/177443 A2 | 12/2012 |
| WO | 2012/177444 A2 | 12/2012 |
| WO | 2012/177929 A2 | 12/2012 |
| WO | 2013/002580 A2 | 1/2013 |
| WO | 2013/004983 A1 | 1/2013 |
| WO | 2013/009545 A1 | 1/2013 |
| WO | 2013/029279 A1 | 3/2013 |
| WO | 2013/041678 A1 | 3/2013 |
| WO | 2012/174478 A9 | 5/2013 |
| WO | 2013/060850 A1 | 5/2013 |
| WO | 2013/074910 A1 | 5/2013 |
| WO | 2013/078500 A1 | 6/2013 |
| WO | 2013/090648 A1 | 6/2013 |
| WO | 2013/092703 A2 | 6/2013 |

(56) References Cited

FOREIGN PATENT DOCUMENTS

| | | |
|---|---|---|
| WO | 2013/093720 A2 | 6/2013 |
| WO | 2013/101749 A1 | 7/2013 |
| WO | 2013/104861 A1 | 7/2013 |
| WO | 2013/148871 A1 | 10/2013 |
| WO | 2013/148966 A1 | 10/2013 |
| WO | 2013/151663 A1 | 10/2013 |
| WO | 2013/151664 A1 | 10/2013 |
| WO | 2013/151665 A2 | 10/2013 |
| WO | 2013/151666 A2 | 10/2013 |
| WO | 2013/151667 A1 | 10/2013 |
| WO | 2013/151668 A2 | 10/2013 |
| WO | 2013/151669 A1 | 10/2013 |
| WO | 2013/151670 A2 | 10/2013 |
| WO | 2013/151671 A1 | 10/2013 |
| WO | 2013/151672 A2 | 10/2013 |
| WO | 2013/151736 A2 | 10/2013 |
| WO | 2013/160397 A1 | 10/2013 |
| WO | 2013/163162 A1 | 10/2013 |
| WO | 2013/164484 A1 | 11/2013 |
| WO | 2013/171135 A1 | 11/2013 |
| WO | 2013/177565 A1 | 11/2013 |
| WO | 2013/186240 A2 | 12/2013 |
| WO | 2013/192129 A1 | 12/2013 |
| WO | 2013/192130 A1 | 12/2013 |
| WO | 2014/012069 A2 | 1/2014 |
| WO | 2014/016300 A1 | 1/2014 |
| WO | 2014/017843 A1 | 1/2014 |
| WO | 2014/017845 A2 | 1/2014 |
| WO | 2014/017849 A1 | 1/2014 |
| WO | 2014/027253 A1 | 2/2014 |
| WO | 2014/027254 A1 | 2/2014 |
| WO | 2014/041195 A1 | 3/2014 |
| WO | 2014/041375 A1 | 3/2014 |
| WO | 2014/049610 A2 | 4/2014 |
| WO | 2014/056872 A1 | 4/2014 |
| WO | 2014/073842 A1 | 5/2014 |
| WO | 2014/073845 A1 | 5/2014 |
| WO | 2014/081872 A1 | 5/2014 |
| WO | 2014/091316 A2 | 6/2014 |
| WO | 2014/096145 A1 | 6/2014 |
| WO | WO 2014096148 A1 | 6/2014 |
| WO | WO 2014096149 A1 | 6/2014 |
| WO | WO 2014096150 A1 | 6/2014 |
| WO | 2014/140222 A1 | 9/2014 |
| WO | 2014/152460 A2 | 9/2014 |
| WO | 2014/158900 A1 | 10/2014 |
| WO | 2014/170496 A1 | 10/2014 |
| WO | 2015/055801 A1 | 4/2015 |
| WO | 2015/055802 A2 | 4/2015 |
| WO | 2015/067716 A1 | 5/2015 |
| WO | 2015/086728 A1 | 6/2015 |
| WO | 2015/086729 A1 | 6/2015 |
| WO | 2015/086730 A1 | 6/2015 |
| WO | 2015/086731 A1 | 6/2015 |
| WO | 2015/086732 A1 | 6/2015 |
| WO | 2015/086733 A1 | 6/2015 |
| WO | WO 2015/086731 A1 | 6/2015 |
| WO | 2015/100876 A1 | 7/2015 |
| WO | 2015/104314 A1 | 7/2015 |
| WO | 2015/132599 A1 | 9/2015 |
| WO | 2016/055610 A1 | 4/2016 |
| WO | 2016/065090 A1 | 4/2016 |
| WO | 2016/198604 A1 | 12/2016 |
| WO | 2016/198624 A1 | 12/2016 |
| WO | WO 2018/100174 A1 | 6/2018 |

OTHER PUBLICATIONS

Bhavsar et al. (Mar. 2013) "Evolution of exenatide as a diabetes therapeutic," Curr. Diabetes Rev. 9(2):161-193.

Gao et al. (Jun. 4, 2012) "A site-specific PEGylated analog of exendin-4 with improved pharmacokinetics and pharmacodynamics in vivo," J. Pharm. Pharmacol. 64(11):1646-1653.

Gupta (May 2013) "Glucagon-like peptide-1 analogues: An overview," Indian J. Endocrinol. Metab. 17(3):413-421.

Hou et al. (Jan. 23, 2013) "Long-term treatment with EXf, a peptide analog of Exendin-4, improves β-cell function and survival in diabetic KKAy mice," Peptides. 40:123-132.

Kim et al. (Nov. 9, 2012) "Site-specific PEGylated Exendin-4 modified with a high molecular weight trimeric PEG reduces steric hindrance and increases type 2 antidiabetic therapeutic effects," Bioconjug. Chem. 23(11):2214-2220.

Lee et al. (Oct. 17, 2013) "Decanoic acid-modified glycol chitosan hydrogels containing tightly adsorbed palmityl-acylated exendin-4 as a long-acting sustained-release anti-diabetic system," Acta Biomater. 10(2):812-820.

Parkes et al. (Dec. 12, 2012) "Discovery and development of exenatide: the first antidiabetic agent to leverage the multiple benefits of the incretin hormone, GLP-1," Expert Opin. Drug Discov. 8(2):219-244.

Qian et al. (Jul. 1, 2013) "Characterization of a site-specific PEGylated analog of exendin-4 and determination of the PEGylation site," Int. J. Pharm. 454(1):553-558.

Simonsen et al. (Jan. 11, 2013) "The C-terminal extension of exendin-4 provides additional metabolic stability when added to GLP-1, while there is minimal effect of truncating exendin-4 in anaesthetized pigs," Regul. Pept. 181:17-21.

Sun et al. (Nov. 6, 2013) "Bifunctional PEGylated exenatide-amylinomimetic hybrids to treat metabolic disorders: an example of long-acting dual hormonal therapeutics," J. Med. Chem. 56(22):9328-9341.

Yim et al. (Aug. 8, 2013) "Synthesis and preclinical characterization of [64Cu]NODAGA-MAL-exendin-4 with a Nε-maleoyl-L-lysyl-glycine linkage," Nucl. Med. Biol. 40(8):1006-1012.

Yue et al. (Jan. 28, 2013) "Development of a new thiol site-specific prosthetic group and its conjugation with [Cys(40)]-exendin-4 for in vivo targeting of insulinomas," Bioconjug. Chem. 24(7):1191-1200.

Guryanov et al. (May 30, 2016) "Innovative chemical synthesis and conformational hints on the lipopeptide liraglutide," J. Pept. Sci. 22:471-479.

Lau et al. (Aug. 26, 2015) "Discovery of the once-weekly Glucagon-like Peptide-1 (GLP-1) analogue Semaglutide," Journal of Medicinal Chemistry. 58:7370-7380.

International Search Report with Written Opinion corresponding to International Patent Application No. PCT/EP2016/063305, dated Oct. 4, 2016.

International Search Report with Written Opinion corresponding to International Patent Application No. PCT/EP2016/066299, dated Jan. 10, 2017.

Shendi et al. (Mar. 14, 2016) "Tunable, bioactive protein conjugated hyaluronic acid hydrogel for neural engineering applications," J. Mater. Chem. B. 4:2803-2818.

Amylin Pharmaceuticals, Inc. (2007) "Byetta: Exenatide Injection," Product Information. Accessible on the Internet at URL: http://www.accessdata.fda.gov/drugsatfda_docs/label/2008/021773s012lbl.pdf. [Last Accessed Jun. 2, 2014].

Baggio et al. (2007) "Biology of incretins: GLP-1 and GIP," Gastroenterology. 132:2131-2157.

Bhat et al. (Jun. 1, 2013) "A novel GIP-oxyntomodulin hybrid peptide acting through GIP, glucagon and GLP-1 receptors exhibits weight reducing and anti-diabetic properties," Biochem. Pharmacol. 85:1655-1662.

Ghat et al. (Mar. 17, 2013) "A DPP-IV-resistant triple-acting agonist of GIP, GLP-1 and glucagon receptors with potent glucose-lowering and insulinotropic actions in high-fat-fed mice," Diabetologia. 56:1417-1424.

Biron et al. (2006) "Optimized selective N-methylation of peptides on solid support," J. Peptide Sci. 12:213-219.

Bis et al. (Jun. 27, 2014) "Antimicrobial preservatives induce aggregation of interferon alpha-2a: the order in which preservatives induce protein aggregation is independent of the protein," Int. J. Pharm. 472:356-361.

Braga et al. (2005) "Making Crystals from Crystals: a green route to crystal engineering and polymorphism," Chem. Commun. 2005:3635-3645.

Bromer (1983) "Chemical Characteristics of Glucagon," Handbook of Experimental Pharmacology. 66:1-22.

(56) References Cited

OTHER PUBLICATIONS

Bunck et al. (Sep. 2011) "Effects of Exenatide on Measures of B-Cell Function After 3 Years in Metformin-Treated Patients with Type 2 Diabetes," Diabetes Care. 34:2041-2047.
Buse et al. (2009) "Liraglutide once a day versus exenatide twice a day for type 2 diabetes: a 26-week randomised, parallel group, multinational, open-label trial (LEAD-6)," The Lancet. 374:39-47.
Chae et al. (2010) "The fatty acid conjugated exendin-4 analogs for type 2 antidiabetic therapeutics," Journal of Controlled Release. 144:10-16.
Chen et al. (Jan. 2014) "Hyaluronic acid-based drug conjugates: state-of-the-art and perspectives," J. Biomed. Nanotechnol. 10(1):4-16.
Chhabra et al. (1998) "An Appraisal of New Variants of Dde Amine Protecting Group for Solid Phase Peptide Synthesis," Tetrahedron Letters. 39:1603-1606.
Creutzfeld et al. (1978) "Gastric inhibitory polypeptide (GIP) and insulin in obesity: increased response to stimulation and defective feedback control of serum levels," Diabetologia. 14:15-24.
Day et al. (2009) "A New Glucagon and GLP-1 co-agonist Eliminates Obesity in Rodents," Nature Chemical Biology. 5 (10):749-757.
Deacon (2004) "Circulation and degradation of GIP and GLP-1," Horm. Metab. Res. 36:761-765.
Donnelly (May 2012) "The structure and function of the glucagon-like peptide-1 receptor and its ligands," Br. J. Pharmacol. 166(1):27-41.
Druce et al. (2009) "Investigation of structure-activity relationships of Oxyntomodulin (Oxm) using Oxm analogs," Endocrinology. 150(4):1712-1722.
Drucker et al. (2010) "Liraglutide," New Reviews—Drug Discovery. 9(4):267-268.
Eng et al. (1990) "Purification and structure of exendin-3, a new pancreatic secretagogue isolated from Heloderma horridum venom," J. Biol. Chem. 265:20259-20262.
Eng et al. (1992) "Isolation and Characterization of Exendin-4, an Exendin-3 Analogue, from Heloderma Suspectum Venom," The Journal of Biological Chemistry. 267(11):7402-7405.
Eng et al. (1996) "Prolonged Effect of Exendin-4 on Hyperglycemia of db/db Mice," Diabetes. 45:152A. Abstract 554.
Ferry, Jr. "Diabetes Health (cont.)," MedicineNet. Accessible on the Internet at URL: http://www.onhealth.com/diabetes_health/page3.htm. [Last Accessed Aug. 22, 2013].
Ficht et al. (2008) "Solid-phase Synthesis of Peptide and Glycopeptide Thioesters through Side-Chain-Anchoring Strategies," Chem. Eur. J. 14:3620-3629.
Finan et al. (Dec. 8, 2014) "A rationally designed monomeric peptide triagonist corrects obesity and diabetes in rodents," Nat. Med. 21(1):27-36.—with supplementary information.
Finan et al. (Oct. 30, 2013) "Unimolecular Dual Incretins Maximize Metabolic Benefits in Rodents, Monkeys, and Humans," Sci. Trans. Med. 5:209RA151.
Furman (Mar. 15, 2012) "The development of Byetta (exenatide) from the venom of the Gilo monster as an anti-diabetic agent," Toxicon. 59:464-471.
Gault et al. (2007) "Chemical gastric inhibitory polypeptide receptor antagonism protects against obesity, insulin resistance, glucose intolerance and associated disturbances in mice fed high-fat and cafeteria diets," Diabetologia. 50:1752-1762.
Gault et al. (Aug. 1, 2011) "Administration of an acylated GLP-1 and GIP preparation provides added beneficial glucose-lowering and insulinotropic actions over single incretins in mice with Type 2 diabetes and obesity," Clin Sci (Lond). 121:107-117.
Gentilella et al. (2009) "Exenatide: A Review from Pharmacology to Clinical Practice," Diabetes, Obesity, and Metabolism. 11:544-556.
Göke et al. (1993) "Exendin-4 is a high potency agonist and truncated exendin-(9-39)-amide an antagonist at the glucagon-like peptide 1-(7-36)-amide receptor of insulin-secreting beta-cells," J. Biol. Chem. 268:19650-19655.
Hadji-Georgopoulos et al. (1983) "Increased gastric inhibitory polypeptide levels in patients with symptomatic postprandial hypoglycemia," J. Endocrinol. Metabol. 56(4):648-652.
Hargrove et al. (2007) "Biological Activity of AC3174, A Peptide Analog of Exendin-4," Regulatory Peptides. 141:113-119.
Heppner et al. (2010) "Glucagon regulation of energy metabolism," Physiol. Behav. 100:545-548.
Herling et al. (1998) "Pharmacodynamic profile of a novel inhibitor of the hepatic glucose-6-phosphatase system," Am. J. Physiol. 274(6 Pt 1):G1087-G1093.
Hjorth et al. (1994) "Glucagon and Glucagon-like Peptide 1: Selective Receptor Recognition via Distinct Peptide Epitopes," The Journal of Biological Chemistry. 269(48):30121-30124.
Holst (2007) "The physiology of glucagon-like peptide 1," Physiol. Rev. 87(4):1409-1439.
Joshi et al. (2000) "The degradation pathways of glucagon in acidic solutions," Int. J. Pharm. 203(1-2):115-125.
Kaiser et al. (1970) "Color test for detection of free terminal amino groups in the solid-phase synthesis of peptides." Anal. Biochem. 34:595-598.
Kamerzell et al. (2011) "Protein—excipient interactions: Mechanisms and biophysical characterization applied to protein formulation development," Adv. Drug Deliv. Rev. 63:1118-1159.
Kazakos et al. (2011) "Incretin effect: GLP-1, GIP, DPP4," Diabetes Res Clin Pract. 93(Suppl 1):S32-536. et al. (2011) "Incretin effect: GLP-1, GIP, DPP4," Diabetes Res Clin Pract. 93(Suppl 1):S32-S36.
King et al. (1990) "A Cleavage Method which Minimizes Side Reactions Following Fmoc Solid Phase Peptide Synthesis," International Journal of Peptide Protein Research. 36:255-266.
Knudsen et al. (2000) "Potent derivatives of glucagon-like peptide-1 with pharmacokinetic properties suitable for once daily administration" J. Med. Chem. 43(9):1664-1669.
Kong et al. (2010) "Long acting hyaluronate—exendin 4 conjugate for the treatment of type 2 diabetes," Biomaterials. 31:4121-4128.
Korczyn et al. (2002) "Emerging Therapies in the Pharmacological Treatment of Parkinson's Disease," Drugs. 62:775-786.
Kosinski et al. (Mar. 16, 2012) "The glucagon receptor is involved in mediating the body weight-lowering effects of oxyntomodulin," Obesity (Silver Spring). 20:1566-1571.
Krstenansky et al. (1986) "Importance of the 10-13 Region of Glucagon for Its Receptor Interaction and Activation of Adenylate Cyclase," Biochemistry. 25(13):3833-3839.
Lee et al. (May 10, 2013) "Hormonal Response to a Mixed-Meal Challenge After Reversal of Gastric Bypass for Hypoglycemia," J. Clin. Endocrinol. Metab. 98(7):E1208-E1212.
Li et al. (Jul. 25, 2012) "Cloning, expressing of Exendin-4 analogue and bioactivity analysis in vivo," Chinese Journal of Biotechnology. 28(7):877-886.
Liu et al. (2011) "Solid phase peptide synthesis and analysis for exendin-4," China Biotechnology. 31(2):69-73.—English abstract and drawings.
Bayram et al. (Sep. 2014) "Effects of glucagon-like peptide-1 in diabetic rat small resistance arteries," Journal of Cardiovascular Pharmacology. 64(3):277-84.
Brom et al. (Feb. 1, 2014) "Non-invasive quantification of the beta cell mass by SPECT with 111In-labelled exendin," Diabetologia. 57(5):950-959.
Cai et al. (Dec. 2014) "Rb and p107 are required for alpha cell survival, beta cell cycle control and glucagon-like peptide-1 action," Diabetologia. 57(12):2555-2565.
Charokopou et al. (Nov. 2014) "Cost-effectiveness of saxagliptin compared to GLP-1 analogues as an add-on to insulin in the treatment of type 2 diabetes mellitus from a UK health care perspective," Value in Health. 17(7):A347. Abstract No. PDB89.
Chen et al. (Dec. 14, 2013) "Exendin-4 is effective against metabolic disorders induced by intrauterine and postnatal overnutrition in rodents," Diabetologia. 57(3):614-622.
Choi et al. (Jun. 2014) "A long-acting exendin-4 analog conjugate to the human fc fragment reveals low immunogenic potential," Diabetes. 63(Suppl 1):A259-A260. Abstract No. 1009-P.
Clemmensen et al. (Dec. 30, 2013) "GLP-1/glucagon coagonism restores leptin responsiveness in obese mice chronically maintained on an obesogenic diet," Diabetes. 63(4):1422-1427.

(56) References Cited

OTHER PUBLICATIONS

De Marinis et al. (Jun. 2014) "Differential action of GLP-1 and GIP on human pancreatic islet function and viability," Diabetes. 63(Suppl 1):A52. Abstract No. 196-OR.

De Marinis et al. (Sep. 2014) "Differential action of GLP-1 and GIP on human pancreatic islet function and viability," Diabetologia. 57(Suppl 1):S171. Abstract No. 401.

Eriksson et al. (Feb. 10, 2014) "Detection of metastatic insulinoma by positron emission tomography with [(68)ga] exendin-4—a case report," J. Clin. Endocrinol. Metab. 99(5):1519-1524.

Eriksson et al. (May 2014) "Effects of the glucagon-like peptide-1 analog exendin-4 on reendothelialization and intimal hyperplasia formation in an animal model of vascular injury," Arteriosclerosis, Thrombosis, and Vascular Biology. 34(Suppl 1): Abstract No. 515.

Gong et al. (Apr. 18, 2014) "Geniposide and its iridoid analogs exhibit antinociception by acting at the spinal GLP-1 receptors," Neuropharmacology. 84:31-45.

Gupta et al. (Sep. 25, 2014) "Mitigation of autophagy ameliorates hepatocellular damage following ischemia reperfusion injury in murine steatotic liver," Am. J. Physiol. Gastrointest. Liver Physiol. 307(11):G1088-G1099.

Jerlhag et al. (Jun. 2014) "A glucagon like peptide-1 analogue reduces alcohol intake and prevents relapse drinking," Alcoholism: Clinical and Experimental Research. 38(Suppl 1):85A. Abstract No. 0339.

Jin et al. (Jun. 24, 2014) "Dipeptidyl peptidase IV inhibitor MK-0626 attenuates pancreatic islet injury in tacrolimus-induced diabetic rats," PloS one. 9(6):e100798. pp. 1-10.

Johnson et al. (Sep. 5, 2014) "A Potent α/β-Peptide Analogue of GLP-1 with Prolonged Action in Vivo," Journal of the American Chemical Society. 136(37):12848-12851.

Kwon et al. (Sep. 2014) "Pharmacological evaluation of once-weekly potentials by combination of long-acting insulin with long-acting exendin4 in an animal model," Diabetologia. 57(Suppl 1):S398-S399. Abstract No. 972.

Li et al. (Apr. 2014) "Vascular protective effect of exendin-4 in experimental models of oxidative stress," Cytotherapy. 16(4 Suppl):S37-S38. Abstract No. 115.

Li et al. (Nov. 5, 2014) "Exendin-4 promotes endothelial barrier enhancement via PKA-and Epac1-dependent Rac1 activation," American Journal of Physiology. 308(2):C164-C175.

Lim et al. (Nov. 18, 2014) "Evaluation of PEGylated Exendin-4 Released from Poly (Lactic-co-Glycolic Acid) Microspheres for Antidiabetic Therapy," Journal of Pharmaceutical Sciences. 104(1):72-80.

Lovshin et al. (Oct. 2014) "Blood pressure-lowering effects of incretin-based diabetes therapies," Canadian Journal of Diabetes. 38(5)364-71.

Lynch et al. (Jun. 24, 2014) "A novel DPP IV-resistant C-terminally extended glucagon analogue exhibits weight-lowering and diabetes-protective effects in high-fat-fed mice mediated through glucagon and GLP-1 receptor activation," Diabetologia. 57(9):1927-1936.

Maas et al. (Oct. 2014) "Impact of the mTOR inhibitor Everolimus on peptide receptor radionuclide therapy in a transgenic neuroendocrine tumor mouse model," European Journal of Nuclear Medicine and Molecular Imaging. 41 (Suppl 2):S529. Abstract No. P593.

Masjkur et al. (Nov. 4, 2014) "Hes3 is Expressed in the Adult Pancreatic Islet and Regulates Gene Expression, Cell Growth, and Insulin Release," The Journal of Biological Chemistry. 289(51):35503-35516.

Mondragon et al. (Aug. 13, 2014) "Divergent effects of liraglutide, exendin-4, and sitagliptin on beta-cell mass and indicators of pancreatitis in a mouse model of hyperglycaemia," PloS one. 9(8):e104873. pp. 1-9.

Nagai et al. (Sep. 2014) "Effects of sitagliptin on body fat and intrahepatic lipid content in Japanese overweight patients with type 2 diabetes," Diabetologia. 57(Suppl 1):S356. Abstract No. 876.

Patel et al. (Sep. 29, 2014) "Cannabinoid receptor 1 antagonist treatment induces glucagon release and shows an additive therapeutic effect with GLP-1 agonist in diet-induced obese mice," Canadian Journal of Physiology and Pharmacology. 92(12):975-983.

Pathak et al. (Nov. 6, 2014) "Antagonism of gastric inhibitory polypeptide (GIP) by palmitoylation of GIP analogues with N- and C-terminal modifications improves obesity and metabolic control in high fat fed mice"; Molecular and Cellular Endocrinology. 401:120-129.

Pi et al. (2014) "胰升血糖素样肽1 类似物治疗糖尿病 的临床研究进展 [Clinical research progresses on glucagon-like peptide-1 analogs in treatment of diabetes mellitus]," 检验医学与临床 [Jianyan Yixue Yu Linchuang]. 11(6):830-832.—with English machine translation.

Qian et al. (Jun. 19, 2014) "Analysis of the interferences in quantitation of a site-specifically PEGylated exendin-4 analog by the Bradford method," Analytical Biochemistry. 465C:50-52.

Roed et al. (Nov. 22, 2013) "Real-time trafficking and signaling of the glucagon-like peptide-1 receptor," Mol. Cell Endocrinol. 382(2):938-949.

Russell et al. (Jun. 2014) "The novel GLP-1-GLP-2 dual agonist ZP-GG-72 increases intestinal growth and improves insulin sensitivity in DIO mice," Diabetes. 63(Suppl 1):A98. Abstract No. 374-OR.

Schattauer Gmbh (Jun. 12, 2014) Meeting Abstracts of the Swiss Society of Radiology and the Swiss Society of Nuclear Medicine 2014. Nuklearmedizin. 53(2):A111-A126.

Tashiro et al. (Jan. 10, 2014) "A glucagon-like peptide-1 analog liraglutide suppresses macrophage foam cell formation and atherosclerosis," Peptides. 54:19-26.

Tweedie et al. (May 2014) "Exendin-4, a candidate treatment for the clinical management of traumatic brain injury," Brain Injury. 28(5-6):549-550. Abstract No. 0101.

Vioix et al. (Nov. 2014) "Cost-minimisation analysis of dapagliflozin compared to lixisenatide as an add-on to insulin in the treatment of type 2 diabetes mellitus from a UK health care perspective," Value in Health. 17(7):A348. Abstract No. PDB95.

Wang et al. (Jun. 2014) "Microfluidic multiplexer perifusion device for studying islet immunotoxicity," Diabetes. 63 (Suppl 1):A555. Abstract No. 2181-P.

Wu et al. (May 24, 2014) "(64)Cu labeled sarcophagine exendin-4 for microPET imaging of glucagon like peptide-1 receptor expression," Theranostics. 4(8):770-777.

Xu et al. (Feb. 11, 2014) "Exendin-4 alleviates high glucose-induced rat mesangial cell dysfunction through the AMPK pathway," Cell. Physiol. Biochem. 33(2):423-432.

Xu et al. (Sep. 2014) "Insulinoma imaging with glucagon-like peptide-1 receptor targeting probe (18)F-FBEM-Cys (39)-exendin-4," Journal of Cancer Research and Clinical Oncology. 140(9):1479-1488.

Yang et al. (2014) "Design, synthesis and biological evaluation of novel peptide MC62 analogues as potential antihyperglycemic agents," European Journal of Medicinal Chemistry. 73:105-111.

Yang et al. (Jun. 2014) "Exendin-4, an analogue of glucagon-like peptide-1, attenuates hyperalgesia through serotonergic pathways in rats with neonatal colonic sensitivity," J. Physiol. Pharmacol. 65(3)349-357.

Yosida et al. (May 13, 2014) "Involvement of cAMP/EPAC/TRPM2 activation in glucose- and incretin-induced insulin secretion," Diabetes. 63(10):3394-3403.

Zhang et al. (Aug. 2014) "GLP-1 ameliorates the proliferation activity of INS-1 cells inhibited by intermittent high glucose concentrations through the regulation of cyclins," Molecular Medicine Reports. 10(2):683-688.

Stoessl et al. (2008) "Potential therapeutic targets for Parkinson's disease," Expert Opinion on Therapeutic Targets. 12(4):425-436.

International Preliminary Report on Patentability corresponding to International Patent Application No. PCT/EP2013/077313, dated Feb. 12, 2015.

International Preliminary Report on Patentability corresponding to International Patent Application No. PCT/EP2014/077336, dated Feb. 26, 2016.

(56) References Cited

OTHER PUBLICATIONS

International Preliminary Report on Patentability corresponding to International Patent Application No. PCT/EP2014/077337, dated Jun. 14, 2016.
International Preliminary Report on Patentability corresponding to International Patent Application No. PCT/EP2014/077338, dated Jun. 14, 2016.
International Preliminary Report on Patentability corresponding to International Patent Application No. PCT/EP2014/077339, dated Jun. 14, 2016.
International Preliminary Report on Patentability corresponding to International Patent Application No. PCT/EP2014/077340, dated Jun. 14, 2016.
International Preliminary Report on Patentability corresponding to International Patent Application No. PCT/EP2014/077341, dated Jun. 14, 2016.
International Search Report with Written Opinion corresponding to International Patent Application No. PCT/EP2013/062090, dated Feb. 7, 2014.
International Search Report with Written Opinion corresponding to International Patent Application No. PCT/EP2013/070882, dated Dec. 5, 2013.
International Search Report with Written Opinion corresponding to International Patent Application No. PCT/EP2013/077307, dated Feb. 18, 2014.
International Search Report with Written Opinion corresponding to International Patent Application No. PCT/EP2013/077310, dated Feb. 18, 2014.
International Search Report with Written Opinion corresponding to International Patent Application No. PCT/EP2013/077312, dated Feb. 18, 2014.
International Search Report with Written Opinion corresponding to International Patent Application No. PCT/EP2013/077313, dated Feb. 18, 2014.
International Search Report with Written Opinion corresponding to International Patent Application No. PCT/EP2014/077336, dated Mar. 18, 2015.
International Search Report with Written Opinion corresponding to International Patent Application No. PCT/EP2014/077337, dated Apr. 1, 2015.
International Search Report with Written Opinion corresponding to International Patent Application No. PCT/EP2014/077338, dated Mar. 26, 2015.
International Search Report with Written Opinion corresponding to International Patent Application No. PCT/EP2014/077339, dated May 11, 2015.
International Search Report with Written Opinion corresponding to International Patent Application No. PCT/EP2014/077340, dated Mar. 18, 2015.
International Search Report with Written Opinion corresponding to International Patent Application No. PCT/EP2014/077341, dated Mar. 18, 2015.
International Search Report with Written Opinion corresponding to International Patent Application No. PCT/EP2015/057416, dated Jun. 22, 2015.
International Search Report with Written Opinion corresponding to International Patent Application No. PCT/EP2015/057417, dated Jun. 17, 2015.
International Search Report with Written Opinion corresponding to International Patent Application No. PCT/EP2015/057418, dated Jun. 19, 2015.
International Search Report with Written Opinion corresponding to International Patent Application No. PCT/EP2015/063607, dated Sep. 23, 2015.
International Search Report with Written Opinion corresponding to International Patent Application No. PCT/EP2016/062496, dated Aug. 3, 2016.
International Search Report with Written Opinion corresponding to International Patent Application No. PCT/EP2016/063332, dated Aug. 10, 2016.
International Search Report with Written Opinion corresponding to International Patent Application No. PCT/EP2016/063339, dated Aug. 8, 2016.
Lorenz et al. (2013) "Recent progress and future options in the development of GLP-1 receptor agonists for the reatment of diabesity" Bioorg. Med. Chem. Lett. 23(14):4011-4018.
Lozano et al. (2013) "Polyarginine nanocapsules: a new platform for intracellular drug delivery," Journal of Nanoparticle Research. 15:1515. pp. 1-14.
Margolis (2004) "Diagnosis of Huntington Disease," Clin. Chem. 49:1726-1732.
Martin et al. (1998) "Neurodegeneration in excitotoxicity, global cerebral ischemia, and target deprivation: A perspective on the contributions of apoptosis and necrosis," Brain Res. Bull. 46:281-309.
McLaughlin et al. (2010) "Reversible Hyperinsulinemic Hypoglycemia after Gastric Bypass: A Consequence of Altered Nutrient Delivery," J. Clin. Endocrinol. Metabol. 95(4):1851-1855.
Medline Plus "Obesity," National Insitute of Health. Accessible on the Internet at URL: http://www.nlm.nih.gov/medlineplus/obesity.html. [Last Accessed Aug. 22, 2013].
Meier (Sep. 4, 2012) "GLP-1 receptor agonists for individualized treatment of type 2 diabetes mellitus," Nat. Rev. Endocrinol. 8:728-742.
Meier et al. (May 21, 2015) "Incretin-based therapies: where will we be 50 years from now?" Diabetologia. 58:1745-1750.
Miyawaki et al. (2002) "Inhibition of gastric inhibitory polypeptide signaling prevents obesity," Nat. Med. 8(7):738-742.
Murage et al. (2008) "Search for alpha-helical propensity in the receptor-bound conformation of glucagon-like peptide-1," Bioorg. Med. Chem. 16:10106-10112.
Nauck et al. (1993) "Additive insulinotropic effects of exogenous synthetic human gastric inhibitory polypeptide and glucagon-like peptide-1-(7-36) amide infused at near-physiological insulinotropic hormone and glucose concentrations," J. Clin. Endocrinol. Metab. 76:912-917.
Norris et al. (2009) "Exenatide Efficacy and Safety: A Systematic Review," Diabetic Medicine. 26:837-846.
Norwegian Institute of Public Health (Dec. 19, 2013) ATC/DDD Index for Cardiovascular System.
Oh et al. (2010) "Target specific and long-acting delivery of protein, peptide, and nucleotide therapeutics using hyaluronic acid derivatives," Journal of Controlled Release. 141:2-12.
Pan et al. (2006) "Design of a long acting peptide functioning as both a glucagon-like peptide-1 receptor agonist and a glucagon receptor antagonist." Journal of Biological Chemistry. 281(18):12506-12515.
Pedersen et al. (2006) "N- and C-terminal hydrophobic patches are involved in fibrillation of glucagon," Biochemistry. 45:14503-14512.
Pocai (2009) "Glucagon-like peptide 1/glucagon receptor dual agonism reverses obesity in mice," Diabetes. 58 (10):2258-2266.
Pocai (Dec. 14, 2013) "Action and therapeutic potential of oxyntomodulin," Molecular Metabolism 3:2412-51.
Rentier et al. (Mar. 26, 2015) "Synthesis of diastereomerically pure Lys(Nε-lipoyl) building blocks and their use in Fmoc/tBu solid phase synthesis of lipoyl-containing peptides for diagnosis of primary biliary cirrhosis," Journal of Peptide Science. 21(5):408-414.
Robberecht et al. (1986) "Comparative efficacy of seven synthetic glucagon analogs, modified in position 1, 2 and/or 12, on liver and heart adenylate cyclase from rat," Peptides. 7(1):109-112.
Rovo et al. (May 2014) "Rational design of a-helix-stabilized exendin-4 analogues," Biochemistry. 53(22):3540-3552.
Seddon (2004) "Pseudopolymorph: A polemic," Crystal Growth and Design. 4(6):1087.
Shiau et al. (1998) "The structural basis of estrogen receptor/coactivator recognition and the antagonism of this interaction by tamoxifen," Cell. 95(7):927-937.
St. John Providence Health System "Preventing Obesity in Children," St. John Providence Health System. Accessible on the Internet at URL: http://www.stjohnprovidence.org/HealthInfoLib/swarticle.aspx?type=85&id=P07863. [Last Accessed Aug. 22, 2013].

(56) References Cited

OTHER PUBLICATIONS

Tasyurek et al. (Jul. 2014) "Incretins: Their physiology and application in the treatment of diabetes mellitus," Diabetes Metab. Res. Rev. 30(5):354-371.
Ueda et al. (2010) "Identification of glycosylated exendin-4 analogue with prolonged blood glucose-lowering activity through glycosylation scanning substitution," Bioorg. Med. Chem. Lett. 20(15):4631-4634.
United Healthcare "Diabetes," United Healthcare. Accessible on the Internet at URL: http://www.uhc.com/source4women/health_topics/diabetes/relatedinformation/d0f0417b073bf110VgnVCM1000002f10b10a.htm. [Last Accessed Aug. 22, 2013].
Unison et al. (1993) "The role of histidine-1 in glucagon action," Arch. Biochem. Biophys. 300(2):747-750.
Vippagunta et al. (2001) "Crystalline Solids," Advanced Drug Delivery Reviews. 48:3-26.
Vojkovsky (1995) "Detection of secondary amines on solid phase," Peptide Research 8:236-237.
Ward et al. (Nov. 2013) "Peptide lipidation stabilizes structure to enhance biological function," Mol. Metabol. 2 (4):468-479.
World Health Organization (2007) "Prevention of Cardiovascular Disease," WorldHealth Organization. pp. 1-86.
Yun et al. (Feb. 2012) "Solution Structure of LXXLL-related Cofactor Peptide of Orphan Nuclear Receptor FTZ-F1." Bulletin of the Korean Chemical Society, 33(2):583-588.
European Search Report corresponding to European Patent Application No. 12172010, dated Apr. 19, 2013.
European Search Report corresponding to European Patent Application No. 12306232, dated Apr. 19, 2013.
European Search Report corresponding to European Patent Application No. 12306647, dated May 22, 2013.
European Search Report corresponding to European Patent Application No. 13306712, dated May 27, 2014.
European Search Report corresponding to European Patent Application No. 13306713, dated Jun. 12, 2014.
European Search Report corresponding to European Patent Application No. 13306714, dated May 28, 2014.
European Search Report corresponding to European Patent Application No. 13306715, dated Jun. 12, 2014.
European Search Report corresponding to European Patent Application No. 13306716, dated May 27, 2014.
European Search Report corresponding to European Patent Application No. 13306717, dated Jun. 3, 2014.
European Search Report corresponding to European Patent Application No. 13305222, dated Jul. 15, 2013.
European Search Report corresponding to European Patent Application No. 14305501, dated Sep. 23, 2014.
European Search Report corresponding to European Patent Application No. 14305503, dated Sep. 23, 2014.
International Preliminary Report on Patentability corresponding to International Patent Application No. PCT/EP2013/062090, dated Nov. 24, 2014.
International Preliminary Report on Patentability corresponding to International Patent Application No. PCT/EP2013/070882, dated Dec. 1, 2014.
International Preliminary Report on Patentability corresponding to International Patent Application No. PCT/EP2013/077307, dated Feb. 12, 2015.
International Preliminary Report on Patentability corresponding to International Patent Application No. PCT/EP2013/077310, dated Feb. 2, 2015.
International Preliminary Report on Patentability corresponding to International Patent Application No. PCT/EP2013/077312, dated Feb. 13, 2015.

* cited by examiner

Various Crosslinking Chemistries to Synthesize HA Hydrogel

1) Aldehyde (diol oxidation) – amine reductive amination

2) Hydroxyl mediated alkylation n = 2, 3, 4, etc   R = H, alkyl, aryl     X = halo, sulphonate, other leaving group 3) Auto-crosslinking H+/ freeze-thaw Various Crosslinking Chemistries to Synthesize HA Hydrogel 4) Michael Addition Crosslinking (Thiol – maleimide)

5) Amide Reaction n = 2, 3, 4 etc    R = H, alkyl, aromatic, heteroaromatic diaminoacid ester etc 6) Diol – Epoxide Chemistry n = 0, 1, 2, etc Click Chemistries 2 +2 Cycloaddition Day 4　　　　　　　　Day 15　　　　　　　　Day 26

Day 1　　　　　　　　Day 4

- 30G, 1" needle using 1mL syringe
- 2% HA-conjugate was mixed with 2% soluble HA at a 4:1 ratio
  - Effective HA-conjugate concentration is 1.6%

SEQUENCE LISTING

```
<160> NUMBER OF SEQ ID NOS: 60

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: Amidated C-terminus

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: Amidated C-terminus

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 29
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15
```

Arg Arg Ala Gln Asp Phe Val Gln Trp Leu Met Asn Thr
            20                  25

<210> SEQ ID NO 4
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 4

His Ser Gln Gly Thr Phe Thr Ser Asp Leu Ser Lys Gln Leu Asp Glu
1               5                   10                  15

Gln Arg Ala Lys Glu Phe Ile Glu Trp Leu Ile Ala Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 5

His Ser Gln Gly Thr Phe Thr Ser Asp Leu Ser Lys Gln Leu Asp Glu
1               5                   10                  15

Gln Arg Ala Lys Glu Phe Ile Glu Trp Leu Ile Ala Gly Gly Pro Val
            20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 6

His Xaa Gln Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Ser
            20                  25                  30

Ser Gly Ala Pro Pro Pro Ser
        35

<210> SEQ ID NO 7
<211> LENGTH: 39

```
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 7

His Xaa Gln Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Val
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 8

His Xaa His Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 9

His Xaa Gln Gly Thr Phe Thr Ser Asp Leu Ser Lys Gln Leu Asp Glu
1               5                   10                  15

Gln Arg Ala Gln Asp Phe Ile Glu Trp Leu Ile Ala Gly Gly Pro Ser
            20                  25                  30

Ser Gly Ala Pro Pro Pro Ser
        35
```

```
<210> SEQ ID NO 10
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 10

His Xaa Gln Gly Thr Phe Thr Ser Asp Leu Ser Lys Gln Leu Asp Glu
 1               5                  10                  15

Gln Arg Ala Lys Asp Phe Ile Glu Trp Leu Ile Ser Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 11

His Xaa Gln Gly Thr Phe Thr Ser Asp Leu Ser Lys Gln Leu Asp Glu
 1               5                  10                  15

Gln Arg Ala Lys Asp Phe Ile Glu Trp Leu Ile Ala Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 12

His Xaa Gln Gly Thr Phe Thr Ser Asp Leu Ser Lys Gln Leu Asp Glu
 1               5                  10                  15

Gln Arg Ala His Asp Phe Ile Glu Trp Leu Ile Ala Gly Gly Pro Ser
            20                  25                  30

Ser Gly Ala Pro Pro Pro Ser
        35
```

```
<210> SEQ ID NO 13
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 13

His Xaa Gln Gly Thr Phe Thr Ser Asp Leu Ser Lys Gln Leu Asp Glu
1               5                   10                  15

Gln Arg Ala Lys Glu Phe Ile Glu Trp Leu Ile Ala Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 14

His Xaa Gln Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Val
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 15

His Xaa Gln Gly Thr Phe Thr Ser Asp Leu Ser Lys Gln Leu Asp Glu
1               5                   10                  15

Gln Arg Ala Gln Asp Phe Ile Glu Trp Leu Ile Ser Gly Gly Pro Ser
            20                  25                  30
```

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 16

His Ser His Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Val
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 17

His Xaa Gln Gly Thr Phe Thr Ser Asp Leu Ser Lys Gln Leu Asp Glu
1               5                   10                  15

Gln Arg Ala Lys Glu Phe Ile Glu Trp Leu Ile Ala Gly Gly Pro Val
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 18

His Xaa His Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Val
            20                  25                  30

Ser Gly Ala Pro Pro Pro Ser
        35

```
<210> SEQ ID NO 19
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 19

His Ser Gln Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Val
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 20

His Xaa Gln Gly Thr Phe Thr Ser Asp Leu Ser Lys Gln Leu Asp Glu
1               5                   10                  15

Gln Arg Ala Lys Glu Phe Ile Glu Trp Leu Ile Ser Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 21

His Xaa His Gly Thr Phe Thr Ser Asp Leu Ser Lys Gln Leu Asp Glu
1               5                   10                  15

Gln Arg Ala Lys Asp Phe Ile Glu Trp Leu Ile Ala Gly Gly Pro Ser
            20                  25                  30

Ser Gly Ala Pro Pro Pro Ser
        35
```

```
<210> SEQ ID NO 22
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 22

His Xaa Gln Gly Thr Phe Thr Ser Asp Leu Ser Lys Gln Leu Asp Glu
1               5                   10                  15

Gln Lys Ala Lys Asp Phe Ile Glu Trp Leu Ile Ala Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 23

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Ala Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 24

His Xaa His Gly Thr Phe Thr Ser Asp Leu Ser Lys Gln Leu Asp Glu
1               5                   10                  15

Gln Leu Ala His Asp Phe Ile Glu Trp Leu Ile Ala Gly Gly Pro Ser
            20                  25                  30

Ser Gly Ala Pro Pro Pro Ser
        35
```

```
<210> SEQ ID NO 25
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 25

His Xaa Gln Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 26

His Xaa His Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 27

His Ser His Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35
```

-continued

<210> SEQ ID NO 28
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 28

His Ser Gln Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 29

His Xaa His Gly Thr Phe Thr Ser Asp Leu Ser Lys Gln Leu Asp Glu
1               5                   10                  15

Gln Leu Ala Lys Glu Phe Ile Glu Trp Leu Ile Ala Gly Gly Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 30

His Xaa His Gly Thr Phe Thr Ser Asp Leu Ser Lys Gln Leu Asp Glu
1               5                   10                  15

Gln Leu Ala Lys Asp Phe Ile Glu Trp Leu Ile Ser Gly Gly Pro Ser
            20                  25                  30

Ser Gly Ala Pro Pro Pro Ser
        35

<210> SEQ ID NO 31
<211> LENGTH: 39

```
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 31

His Xaa His Gly Thr Phe Thr Ser Asp Leu Ser Lys Gln Leu Asp Glu
1               5                   10                  15

Gln Leu Ala Lys Asp Phe Ile Glu Trp Leu Ile Lys Gly Gly Pro Ser
            20                  25                  30

Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 32

His Xaa His Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Val
            20                  25                  30

Ser Gly Ala Pro Pro Pro Ser
        35

<210> SEQ ID NO 33
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 33

His Xaa His Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35
```

```
<210> SEQ ID NO 34
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 34

His Ser His Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
            35

<210> SEQ ID NO 35
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 35

His Xaa Gln Gly Thr Phe Thr Ser Asp Leu Ser Lys Gln Leu Asp Glu
1               5                   10                  15

Gln Leu Ala Lys Glu Phe Ile Glu Trp Leu Ile Ala Gly Gly Pro Ser
            20                  25                  30

Ser Gly Ala Pro Pro Pro Ser
            35

<210> SEQ ID NO 36
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 36

His Xaa Gln Gly Thr Phe Thr Ser Asp Leu Ser Lys Gln Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
            35

<210> SEQ ID NO 37
<211> LENGTH: 39
```

```
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 37

His Xaa His Gly Thr Phe Thr Ser Asp Leu Ser Lys Gln Leu Asp Glu
 1               5                  10                  15

Gln His Ala Lys Asp Phe Ile Glu Trp Leu Ile Ala Gly Gly Pro Ser
            20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 38

His Xaa His Gly Thr Phe Thr Ser Asp Leu Ser Lys Gln Leu Asp Glu
 1               5                  10                  15

Gln Leu Ala Gln Asp Phe Ile Glu Trp Leu Ile Ala Gly Gly Pro Ser
            20                  25                  30

Ser Gly Ala Pro Pro Pro Ser
        35

<210> SEQ ID NO 39
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 39

His Xaa Gln Gly Thr Phe Thr Ser Asp Leu Ser Lys Gln Leu Asp Glu
 1               5                  10                  15

Gln Leu Ala Gln Glu Phe Ile Glu Trp Leu Ile Ala Gly Gly Pro Ser
            20                  25                  30

Ser Gly Ala Pro Pro Pro Ser
        35
```

```
<210> SEQ ID NO 40
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 40

His Xaa Gln Gly Thr Phe Thr Ser Asp Leu Ser Lys Leu Leu Asp Glu
1               5                   10                  15

Gln Arg Ala Lys Asp Phe Ile Glu Trp Leu Ile Ala Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Amidated C-terminus

<400> SEQUENCE: 41

His Xaa His Gly Thr Phe Thr Ser Asp Leu Ser Lys Leu Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 42

His Xaa Gln Gly Thr Phe Thr Ser Asp Leu Ser Lys Leu Leu Asp Glu
1               5                   10                  15

Gln Arg Ala Lys Asp Phe Ile Glu Trp Leu Ile Ala Gly Gly Pro Val
            20                  25                  30

Ser Gly Ala Pro Pro Pro Ser
        35
```

<210> SEQ ID NO 43
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (39)..(39)
<223> OTHER INFORMATION: Amidated C-terminus

<400> SEQUENCE: 43

His Xaa His Gly Thr Phe Thr Ser Asp Leu Ser Lys Leu Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (39)..(39)
<223> OTHER INFORMATION: Amidated C-terminus

<400> SEQUENCE: 44

His Ser His Gly Thr Phe Thr Ser Asp Leu Ser Lys Leu Leu Asp Glu
1               5                   10                  15

Gln Leu Ala Lys Asp Phe Ile Glu Trp Leu Ile Ala Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 45

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 46

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Gly Gly Pro Pro
            20                  25                  30

Ser Gly Ala Pro Pro Pro Ser
        35

<210> SEQ ID NO 47
<211> LENGTH: 41
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (41)..(41)
<223> OTHER INFORMATION: Amidated C-terminus

<400> SEQUENCE: 47

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Gly Gly Pro Pro
            20                  25                  30

Ser Gly Pro Pro Pro Pro Pro Pro
        35                  40

<210> SEQ ID NO 48
<211> LENGTH: 41
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)

```
<223> OTHER INFORMATION: bAla
<220> FEATURE:
<221> NAME/KEY: MOD_RES
<222> LOCATION: (29)..(29)
<223> OTHER INFORMATION: D-Ala
<220> FEATURE:
<221> NAME/KEY: MOD_RES
<222> LOCATION: (34)..(34)
<223> OTHER INFORMATION: D-Ala
<220> FEATURE:
<221> NAME/KEY: MOD_RES
<222> LOCATION: (41)..(41)
<223> OTHER INFORMATION: Amidated C-terminus

<400> SEQUENCE: 48

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Xaa Gly Pro Pro
            20                  25                  30

Ser Xaa Pro Pro Pro Pro Pro Pro
        35                  40

<210> SEQ ID NO 49
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 49

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Gly Gly Pro His
            20                  25                  30

Ser Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 50

His Xaa His Gly Thr Phe Thr Ser Asp Leu Ser Lys Gln Leu Asp Glu
```

```
1               5                   10                  15
Gln Leu Ala Arg Asp Phe Ile Glu Trp Leu Ile Xaa Pro Gly Pro Ser
            20                  25                  30

Ser Gly Ala Pro Pro Pro Ser
            35
```

<210> SEQ ID NO 51
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 51

```
His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Pro Gly Pro Pro
            20                  25                  30

Ser Gly Ala Pro Pro Pro Ser
            35
```

<210> SEQ ID NO 52
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 52

```
His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Pro Gly Pro His
            20                  25                  30

Ser Gly Ala Pro Pro Pro Ser
            35
```

<210> SEQ ID NO 53
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES

```
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 53

His Xaa His Gly Thr Phe Thr Ser Asp Leu Ser Lys Gln Leu Asp Glu
 1               5                  10                  15

Gln Leu Ala Arg Asp Phe Ile Glu Trp Leu Ile Xaa Gly Gly Pro Pro
             20                  25                  30

Ser Gly Lys Pro Pro Pro Ser
             35

<210> SEQ ID NO 54
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 54

His Xaa His Gly Thr Phe Thr Ser Asp Leu Ser Lys Gln Leu Asp Glu
 1               5                  10                  15

Gln Leu Ala Arg Asp Phe Ile Glu Trp Leu Ile Xaa Gly Gly His Pro
             20                  25                  30

Ser Gly Ala Pro Pro Pro Ser
             35

<210> SEQ ID NO 55
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 55

His Xaa His Gly Thr Phe Thr Ser Asp Leu Ser Lys Gln Leu Asp Glu
 1               5                  10                  15

Gln Leu Ala Arg Asp Phe Ile Glu Trp Leu Ile Xaa Gly Gly Trp Pro
```

-continued

```
                    20                  25                  30

Ser Gly Ala Pro Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 56

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Gly Gly His Pro
            20                  25                  30

Ser Gly Lys Pro Pro Pro Ser
        35

<210> SEQ ID NO 57
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 57

His Xaa His Gly Thr Phe Thr Ser Asp Leu Ser Lys Gln Leu Glu Glu
1               5                   10                  15

Gln Leu Ala Arg Asp Phe Ile Glu Trp Leu Ile Xaa Gly Gly Pro Pro
            20                  25                  30

Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
```

```
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (39)..(39)
<223> OTHER INFORMATION: Amidated C-terminus

<400> SEQUENCE: 58

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Gly Gly Pro Arg
            20                  25                  30

Ser Gly Ala Pro Pro Pro Ser
        35

<210> SEQ ID NO 59
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (29)..(29)
<223> OTHER INFORMATION: D-Ala
<220> FEATURE:
<221> NAME/KEY: MOD_RES
<222> LOCATION: (34)..(34)
<223> OTHER INFORMATION: D-Ala
<220> FEATURE:
<221> NAME/KEY: MOD_RES
<222> LOCATION: (39)..(39)
<223> OTHER INFORMATION: Amidated C-terminus

<400> SEQUENCE: 59

His Xaa His Gly Thr Phe Thr Ser Asp Leu Ser Lys Gln Leu Asp Glu
1               5                   10                  15

Gln Leu Ala Arg Asp Phe Ile Glu Trp Leu Ile Xaa Xaa Gly Pro Pro
            20                  25                  30

Ser Xaa Ala Pro Pro Pro Ser
        35

<210> SEQ ID NO 60
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (28)..(28)
<223> OTHER INFORMATION: bAla
<220> FEATURE:
<221> NAME/KEY: MOD_RES
<222> LOCATION: (29)..(29)
<223> OTHER INFORMATION: D-Ala
<220> FEATURE:
<221> NAME/KEY: MOD_RES
```

```
<222> LOCATION: (34)..(34)
<223> OTHER INFORMATION: D-Ala
<220> FEATURE:
<221> NAME/KEY: MOD_RES
<222> LOCATION: (39)..(39)
<223> OTHER INFORMATION: Amidated C-terminus

<400> SEQUENCE: 60

His Xaa Gln Gly Thr Phe Thr Ser Asp Leu Ser Lys Leu Leu Glu Glu
1               5                   10                  15

Gln Arg Ala Arg Glu Phe Ile Glu Trp Leu Ile Xaa Xaa Gly Pro Pro
            20                  25                  30

Ser Xaa Ala Pro Pro Pro Ser
        35
```

PRODRUGS COMPRISING AN GLP-1/GLUCAGON DUAL AGONIST LINKER HYALURONIC ACID CONJUGATE

RELATED APPLICATIONS

This application is a 35 U.S.C. § 371 filing of International Patent Application No. PCT/EP2016/062496, filed Jun. 2, 2016, which claims priority to European Patent Application No. 15305858.1, filed Jun. 5, 2015, the entire disclosures of which are hereby incorporated herein by reference in their entirety.

The present invention relates to GLP-1/Glucagon dual agonist prodrugs, pharmaceutical compositions comprising said prodrugs as well as their use as a medicament for treating or preventing diseases or disorders which can be treated by a GLP-1/Glucagon dual agonist, for example in the treatment of disorders of the metabolic syndrome, including diabetes and obesity, as well as for reduction of excess food intake.

BACKGROUND OF THE INVENTION

GLP-1 Agonists

Exendin-4 is a 39-amino acid peptide, isolated from the salivary secretions of the venomous Gila monster (*Heloderma suspectum*). It has some sequence similarity to several members of the glucagon-like peptide family, with the highest homology of 53% being to glucagon-like peptide-1 [7-36]-amide (GLP-1). Exendin-4 acts as a agonist on the GLP-1 receptor and bears GLP-1-like insulin sectretagogue action in isolated rat islets. Exendin-4 is a high potency agonist and truncated GLP-1 agonist-(9-39)-amide is an antagonist at the glucagon-like peptide 1-(7-36)-amide receptor of insulin-secreting beta-cells. (see e.g. J. Biol. Chem. 268(26):19650-19655). Exendin-4 ("exenatide") was approved recently in the US and EU for improving glycemic control in patients with type 2 diabetes taking metformin and/or a sulfonylurea but have not achieved adequate glycemic control.

The amino acid sequence of exendin-4 is shown as SEQ ID NO: 1

HGEGTFTSDLSKQMEEEAVRLFIEWLKNGGPSSGAPPPS-NH$_2$

The amino acid sequence of GLP-1(7-36)-amide is shown as SEQ ID NO 2

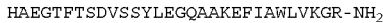

HAEGTFTSDVSSYLEGQAAKEFIAWLVKGR-NH$_2$

Glucagon is a 29-amino acid peptide which is released into the bloodstream when circulating glucose is low. Glucagon's amino acid sequence is shown in SEQ ID NO 3.

HSQGTFTSDYSKYLDSRRAQDFVQWLMNT-OH

During hypoglycemia, when blood glucose levels drop below normal, glucagon signals the liver to break down glycogen and release glucose, causing an increase of blood glucose levels to reach a normal level. Hypoglycemia is a common side effect of insulin treated patients with hyperglycemia (elevated blood glucose levels) due to diabetes. Thus, glucagon's most predominant role in glucose regulation is to counteract insulin action and maintain blood glucose levels.

Hoist (Hoist, J. J. Physiol. Rev. 2007, 87, 1409) and Meier (Meier, J. J. Nat. Rev. Endocrinol. 2012, 8, 728) describe that GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

GLP-1/Glucagon (Glc) Agonists

Pocai et al (Obesity. 2012; 20:1566-1571; Diabetes 2009, 58, 2258) and Day et al. (Nat Chem Biol 2009; 5:749) describe that dual activation of the GLP-1 and glucagon receptors, e.g., by combining the actions of GLP-1 and glucagon in one molecule leads to a therapeutic principle with anti-diabetic action and a pronounced weight lowering effect.

Peptides which bind and activate both the glucagon and the GLP-1 receptor (Hjort et al. Journal of Biological Chemistry, 269, 30121-30124, 1994; Day J W et al, Nature Chem Biol, 5: 749-757, 2009) and suppress body weight gain and reduce food intake are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO2011/117415, WO2011/117416, and WO 2006/134340, the contents of which are herein incorporated by reference.

In addition, triple co-agonist peptides which not only activate the GLP-1 and the glucagon receptor, but also the GIP receptor (Gastric inhibitory polypeptide) are described in WO 2012/088116 and by VA Gault et al (Biochem Pharmacol, 85, 16655-16662, 2013; Diabetologia, 56, 1417-1424, 2013).

Bloom et al. (WO 2006/134340) disclose that peptides which bind and activate both the glucagon and the GLP-1 receptor can be constructed as hybrid molecules from glucagon and exendin-4, where the N-terminal part (e.g. residues 1-14 or 1-24) originate from glucagon and the C-terminal part (e.g. residues 15-39 or 25-39) originate from exendin-4.

Otzen et al (Biochemistry, 45, 14503-14512, 2006) disclose that N- and C-terminal hydrophobic patches are involved in fibrillation of glucagon, due to the hydrophobicity and/or high β-sheet propensity of the underlying residues.

WO2014/056872 discloses peptides which bind and activate both the glucagon and the GLP-1 receptor that are derived from exendin-4 wherein at least the aminoacid at position 14 bear a side chain for a prolonged halflife.

Peptides used in this invention are exendin-4 peptide analogues comprising leucine in position 10 and glutamine in position 13 and are described in WO2015/086731, WO2015/086732, WO2015/086733.

Peptides also used in this invention are exendin-4 peptide analogues comprising beta-alanine in position 28 and are described in EP15305899.5.

Further a peptide is used in this invention which is a exendin-4 peptide analogue comprising glutamine at position 3, beta-alanine in position 28 and D-alanines in position 29 and 34.

Peptides used in this invention preferably are soluble not only at neutral pH, but also at pH 4.5. Also the chemical stability at pH values of 4.5 to 5 is an important criterion for the long acting prodrug product. The prodrug is preferably formulated in this pH range in order to obtain a shelflife from at least 6 month at 4° C.

Longacting GLP-1/Glucagon Agonists

Ideally, the peptide is formulated in a fashion that provides for a sustained plasma level in human for at least one week after application to a human body resulting in a once-weekly or longer injection frequency.

Current therapy with a long acting GLP-1 agonists is Bydureon® which is exendin-4 in a depot suspension for a once weekly injection based on poly(glycol-co lactic acid) using a 23 gauge needle.

WO2012/173422 describes a GLP-1/Glucagon agonist conjugated to the Fc region of an immunoglobulin for weekly administration wherein the peptide is derived from oxyntomodulin.

Carrier Linked Prodrugs

To enhance physicochemical or pharmacokinetic properties of a drug in vivo, such as its half-live, such drug can be conjugated with a carrier. If the drug is transiently bound to a carrier and/or a linker, such systems are commonly assigned as carrier-linked prodrugs. According to the definitions provided by IUPAC (as given under http://www-.chem.qmul.ac.uk/iupac.medchem, accessed on Jul. 22, 2009), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers employed in such carrier-linked prodrugs may be transient, meaning that they are non-enzymatically hydrolytically degradable (cleavable) under physiological conditions (aqueous buffer at pH 7.4, 37° C.) with half-lives ranging from, for example, one hour to three months. Suitable carriers are polymers and can either be directly conjugated to the linker or via a non-cleavable spacer.

Transient polymer conjugation through traceless prodrug linkers combines the advantages of prolonged residence time due to polymer attachment and the recovery of the original pharmacology of the native peptide after release from the polymer conjugate.

Using polymer-linker peptide conjugates, native unchanged peptide is slowly released after application to a patient, governed only by release kinetics of the linker and pharmacokinetics of the polymer carrier. Ideally, release kinetics would be independent from the presence of enzymes like proteases or esterases in body fluids to guarantee a consistent and homogenous release pattern.

WO2008/148839, WO2009/095479 and WO2012/035139 refer to prodrugs comprising drug linker conjugates, where the linker is covalently attached via a cleavable bond to a biologically active moiety, such as the GLP 1-agonist exendin-4. The biologically active moiety is released from the prodrug upon cyclization-activation by cyclic imide formation. The release kinetic is dependent on the pH value and is minimum for storage of the prodrug at pH values from 4.5 to 5 and reach its intended release rate at physiological pH of around 7.4 to 7.5. An GLP-1 agonist-prodrug is described in which the linker is based on L-alanine and the polymeric carrier is a PEG-lysine based hydrogel. Not described are dual GLP-1/Glucagon agonist-prodrugs.

Hyaluronic Acid (HA)

Dhal et al (Journal of Biomedical Nanotechnology, vol 9, 2013, 1-13) report hyaluronic acid as a suitable carrier for drug conjugates. Kong et al. (Biomaterials 31 (2010), 4121-4128) report an exendin-4-hyaluronic acid conjugate which showed an glucose lowering effect over 3 days in mice. The used HA was a linear polymer with a drug load ranging from about 2.4 to 12.%.

In the present invention hydrogels of crosslinked hyaluronic acid are chosen due to their longer residence time as a local depot at the application site than soluble HA. Important criteria for the use of hyaluronic acid (HA) as a carrier polymer is the achievable drug load in the final drug product which is determined by the drug load on the polymer itself and the concentration of the final solution/suspension. Giving the fact that the injection volume for subcutaneous drug depots is practically limited to equal/less than 1 mL, preferably equal/less than 0.6 mL.

The more concentrated the polymer solutions/suspensions of HA is, the more viscous is the formulation which has a negative impact on the syringability of the prodrug formulation. Viscous solutions need injection needles of a larger diameter to limit the force on the plunger of which the syringe is pressed. Also the time for injection is longer.

It is an object of the present invention to provide a GLP-1/Glucagon agonist prodrug for administering as a subcutaneous depot which releases a GLP-1/Glucagon agonist in an active form over the time period of at least 6 days between administrations and which can be injected through 26 gauge needles or even needles of smaller inner diameter for good patient compliance.

An object of the invention is a prodrug or a pharmaceutically acceptable salt thereof comprising a drug linker conjugate of formula (I)

$$Z-L^1-L^2-L-Y-R^{20} \quad (I)$$

wherein Y is a peptide moiety having the formula (II)

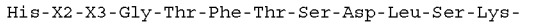
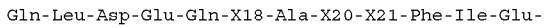
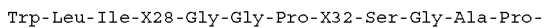

His-X2-X3-Gly-Thr-Phe-Thr-Ser-Asp-Leu-Ser-Lys-

Gln-Leu-Asp-Glu-Gln-X18-Ala-X20-X21-Phe-Ile-Glu-

Trp-Leu-Ile-X28-Gly-Gly-Pro-X32-Ser-Gly-Ala-Pro-

Pro-Pro-Ser

X2 represents an amino acid residue selected from Ser, D-Ser and Aib,

X3 represents an amino acid residue selected from Gln and His,

X18 represents an amino acid residue selected from Arg and Lys

X20 represents an amino acid residue selected from Lys, Gln and His,

X21 represents an amino acid residue selected from Asp and Glu,

X28 represents an amino acid residue selected from Ser and Ala,

X32 represents an amino acid residue selected from Ser and Val, or wherein Y is a peptide moiety having the formula (III)

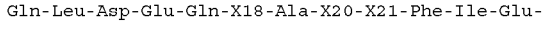
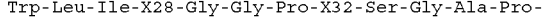

His-X2-X3-Gly-Thr-Phe-Thr-Ser-Asp-Leu-Ser-Lys-

Gln-Leu-Asp-Glu-Gln-X18-Ala-X20-X21-Phe-Ile-Glu-

Trp-Leu-Ile-X28-Gly-Gly-Pro-X32-Ser-Gly-Ala-Pro-

Pro-Pro-Ser

X2 represents an amino acid residue selected from Ser, D-Ser and Aib,

X3 represents an amino acid residue selected from Gln and His,

X18 represents an amino acid residue selected from Leu and His

X20 represents an amino acid residue selected from His, Arg, Lys, and Gln,

X21 represents an amino acid residue selected from Asp and Glu,

X28 represents an amino acid residue selected from Lys, Ser and Ala,

X32 represents an amino acid residue selected from Ser and Val, or wherein Y is a peptide moiety having the formula (IV)

```
His-X2-X3-Gly-Thr-Phe-Thr-Ser-Asp-Leu-Ser-Lys-    (IV)
Leu-Leu-Asp-Glu-Gln-X18-Ala-Lys-Asp-Phe-Ile-Glu-
Trp-Leu-Ile-Ala-Gly-Gly-Pro-X32-Ser-Gly-Ala-Pro-
Pro-Pro-Ser
```

X2 represents an amino acid residue selected from Ser, D-Ser and Aib,

X3 represents an amino acid residue selected from Gln and His,

X18 represents an amino acid residue selected from Arg and Leu,

X32 represents an amino acid residue selected from Ser and Val, or wherein Y is a peptide moiety having the formula (IVa)

```
                                                    (IVa)
H2N-His-Aib-His-Gly-Thr-Phe-Thr-Ser-Asp-Leu-Ser-
Lys-Gln-Leu-X15-Glu-Gln-Leu-Ala-Arg-Asp-Phe-Ile-
Glu-Trp-Leu-Ile-Bal-X29-Gly-X31-X32-Ser-X34-X35-
Pro-Pro-Pro-X39-R20
```

X15 represents an amino acid residue selected from Asp and Glu, (pref. Asp)

X29 represents an amino acid residue selected from Gly, D-Ala and Pro, (pref) Gly, D-Ala X31 represents an amino acid residue selected from Pro, His and Trp, (pref. Pro)

X32 represents an amino acid residue selected from Ser, His, Pro and Arg, (pref. Ser, His, Pro), X34 represents an amino acid residue selected from Gly and D-Ala, X35 represents an amino acid residue selected from Ala, Pro and Lys, (pref. Ala, Pro)

X39 represents Ser or Pro-Pro-Pro, or wherein Y is a peptide moiety having the formula (IVb)

```
H2N-His-Aib-Gln-Gly-Thr-Phe-Thr-Ser-Asp-Leu-Ser-
Lys-Leu-Leu-Glu-Glu-Gln-Arg-Ala-Arg-Glu-Phe-Ile-
Glu-Trp-Leu-Ile-Bal-D-Ala-Gly-Pro-Pro-Ser-D-Ala-
Ala-Pro-Pro-Pro-Ser-R20;
``` or a salt or solvate thereof;

$R^{20}$ is OH or $NH_2$;

L is a linker of formula (Ia),

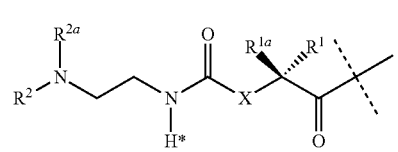

wherein the dashed line indicates the attachment to the N-Terminus of Y by forming an amide bond;

X is $C(R^4R^{4a})$; $N(R^4)$;

$R^1$, $R^{1a}$, are independently selected from the group consisting of H; and $C_{1-4}$ alkyl;

$R^2$, $R^{2a}$, are independently selected from the group consisting of H; and $C_{1-4}$ alkyl;

$R^4$, $R^{4a}$, are independently selected from the group consisting of H; and $C_{1-4}$ alkyl;

wherein $R^2$, $R^{2a}$, $R^4$ or $R^{4a}$ is substituted with one group $L^2$-$L^1$-Z; wherein $R^{2a}$, $L^2$ is a single chemical bond or is a $C_{1-20}$ alkyl chain, which is optionally interrupted by one or more groups independently selected from —O— and $C(O)N(R^{3aa})$ and is optionally substituted with one or more groups independently selected from OH and $C(O)N(R^{3aa}R^{3aaa})$, wherein $R^{3aa}$ and $R^{3aaa}$ are independently selected from the group consisting of H and $C_{1-4}$ alkyl; and $L^2$ is attached to $L^1$ via a terminal group selected from the group consisting of

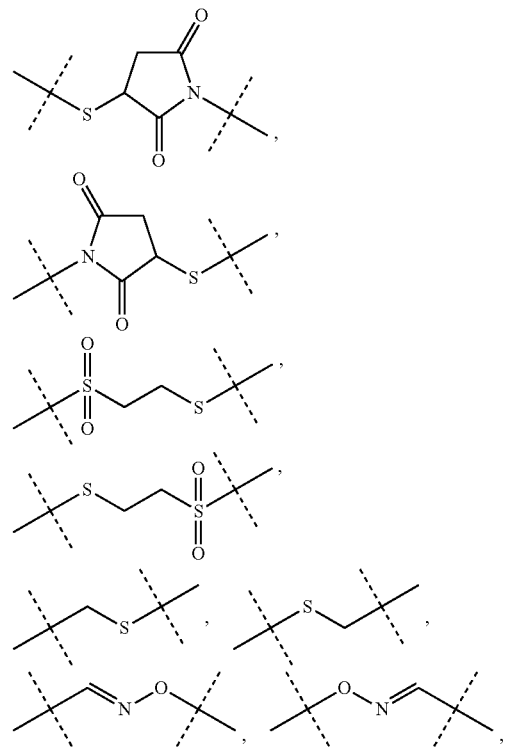

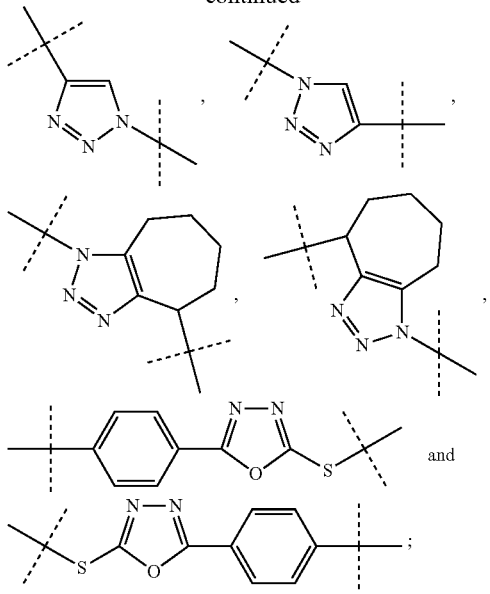

and wherein L² is attached to the one position indicated with the dashed line and L¹ is attached to the position indicated with the other dashed line; and L¹ is a $C_{1-20}$ alkyl chain, which is optionally interrupted by one or more groups independently selected from —O— and $C(O)N(R^{5aa})$ and is optionally substituted with one or more groups independently selected from OH and $C(O)N(R^{5aa}R^{5aaa})$, wherein $R^{5aa}$ and $R^{5aaa}$ are independently selected from the group consisting of H and $C_{1-4}$ alkyl; and L¹ is attached to Z via a terminal amino group forming an amide bond with the carboxy group of the beta-1,3-D-glucuronic acid of the hyaluronic acid of Z;

Z is a crosslinked hyaluronic acid hydrogel, in which 0.05 to 20% of the monomeric disaccharide units are crosslinked by a crosslinker; and 0.2 to 8.5% of the monomeric disaccharide units bear $L'$-$L^2$-L-Y—$R^{20}$.groups.

The present invention relates to a prodrug which provides a GLP-1/Glucagon agonist release from a subcutaneous depot in an active form over the time period of at least 6 days between administrations This helps patients to reduce the frequency of injections, while being able to maintain optimal control the plasma levels of GLP-1/Glucagon agonist and consequently blood glucose.

Further advantages of the crosslinked hyaluronic acid carrier of the invention are the good injectability through a 26 gauge needle or even a needle of a smaller inner diameter.

LEGENDS TO THE FIGURES

FIG. 1a, FIG. 1b, FIG. 1c show various crosslinking chemistries to synthesize hyaluronic acid hydrogels.

FIG. 2a. Magnetic Resonance (MR) images of the HA hydrogel at the injection site, taken at different time points.

FIG. 2b. Magnetic Resonance (MR) images of the polymer suspension containing 1:1 (w/w) HA hydrogel-800 kDa soluble HA at the injection site, taken at different time points.

FIG. 3. In vitro release kinetics of Exendin-4 Seq ID No. 26 dual agonist with weekly linker from the HA hydrogel (example 18). The half-life is 5 days.

FIG. 4 In vivo Effect of HA Hydrogel-Dual Agonist (Seq ID No. 26) Conjugate on Non-fasting Blood Glucose in db/db Mice: shown is the difference level of blood glucose in mmol/L versus the treatment time of the animals for different doses.

FIG. 4b In vivo Effect of HA Hydrogel-Dual Agonist (Seq ID No. 26) Conjugate on Non-fasting Blood Glucose in db/db Mice: shown is the difference level of blood glucose in mmol/L versus the treatment time of the animals for different hydrogel constructs: soluble and crosslinked hyaluronic acid.

FIG. 4c In vivo Effect of HA Hydrogel-Dual agonists (Seq ID No. 45, 46 and 48) Conjugates on Non-fasting Blood Glucose in db/db Mice: shown is the level of blood glucose in mmol/L versus the treatment time of the animals.

FIG. 4d In vivo Effect of HA Hydrogel-Dual Agonist (Seq ID No. 49) Conjugate on Non-fasting Blood Glucose in db/db Mice: shown is the level of blood glucose in mmol/L versus the treatment time of the animals.

FIG. 5 Injectability study: Extrusion Force on syringe plunger for HA hydrogels of different peptide loading.

DETAILED DESCRIPTION

The amino acid sequences of the present invention contain the conventional one letter and three letter codes for naturally occurring amino acids, as well as generally accepted three letter codes for other amino acids, such as Aib (α-aminoisobutyric acid). Furthermore, the following code was used for the amino acid shown in the table below.

| Name | Structure | code |
|---|---|---|
| beta alanine | $H_2N$~~~OH, O | Bal |
| D-alanine | | D-Ala |

GLP-1/Glucagon agonist bound to linker is referred to as "GLP-1/Glucagon agonist moiety".

"Protective groups" refers to a moiety which temporarily protects a chemical functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

"Protected functional groups" means a chemical functional group protected by a protective group.

"Acylating agent" means a moiety of the structure R—(C=O)—, providing the acyl group in an acylation reaction, optionally connected to a leaving group, such as acid chloride, N-hydroxy succinimide, pentafluorphenol and para-nitrophenol.

"Alkyl" means a straight-chain or branched carbon chain. Each hydrogen of an alkyl carbon may be replaced by a substituent.

"Aryl" refers to any substituent derived from a monocyclic or polycyclic or fused aromatic ring, including heterocyclic rings, e.g. phenyl, thiophene, indolyl, napthyl, pyridyl, which may optionally be further substituted.

"Acyl" means a chemical functional group of the structure R—(C=O)—, wherein R is an alkyl or aryl.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent.

Accordingly, "$C_{1-18}$ alkyl" means an alkyl chain having 1 to 18 carbon atoms and "$C_{8-18}$ alkyl" means an alkyl chain having 8 to 18 carbon atoms. Accordingly, "$C_{1-50}$ alkyl" means an alkyl chain having 1 to 50 carbon atoms.

"Halogen" means fluoro, chloro, bromo or iodo. It is generally preferred that halogen is fluoro or chloro.

"Hyaluronic acid" means a polymer of a disaccharide composed of beta-1,3-D-glucuronic acid and beta-1,4-N-acetyl-D-glucosamine and their respective sodium salts. These polymers are linear.

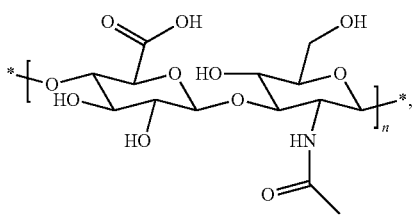

"Disaccharide unit" means the disaccharide composed of beta-1,3-D-glucuronic acid and beta-1,4-N-acetyl-D-glucosamine and their respective sodium salts and is the monomeric building block for HA.

"Crosslinked hyaluronic acid" means a polymer of hyaluronic acid" wherein different chains of HA are covalently connected by a crosslinker, forming a 3-dimensional polymer network. The degree of crosslinking refers the molar ratio of disaccharide units to crosslinker units in the polymer network.

Crosslinked hyaluronic acid" may be derived by different methods. Reaction of HA with the crosslinker, reaction of modified (activated) HA with the crosslinker, reaction of two different modified HA with the crosslinker. Examples may be described in Oh et al, Journal of Controlled Release 141 (2010), 2-12. Example 11 describes the crosslinking of unmodified HA with divinylsulfone. Further methods for preparing crosslinked HA are also depicted in FIG. 1a, FIG. 1b and FIG. 1c: aldehyde (diol oxidation) and subsequent amine reductive amination, hydroxyl mediated alkylation, amide formation reaction, Michael Addition Crosslinking (Thiol-maleimide), diol-epoxide chemistry and others.

"Crosslinker" may be a linear or branched molecule or chemical group, preferably is a linear molecule with at least chemical functional groups on each distal ends "functionalized hyaluronic acid" means a polymer of hyaluronic acid" wherein HA is chemically modified with a group $L^1$ which bears a chemical functional chemical group at its distal end. The degree of functionalization refers the molar ratio of disaccharide units to $L^1$ units in the polymer.

The term "chemical functional group" refers to but not limited to carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine.

If a chemical functional group is coupled to another chemical functional group, the resulting chemical structure is referred to as "linkage". For example, the reaction of an amine group with a carboxyl group results in an amide linkage.

"Reactive functional groups" are chemical functional groups of the backbone moiety, which are connected to the hyperbranched moiety.

"Functional group" is the collective term used for "reactive functional group", "degradable interconnected functional group", or "conjugate functional group".

The terms "blocking group" or "capping group" are used synonymously and refer to moieties which are irreversibly connected to reactive functional groups to render them incapable of reacting with for example chemical functional groups.

The terms "protecting group" or "protective group" refers to a moiety which is reversibly connected to reactive functional groups to render them incapable of reacting with for example other chemical functional groups under specific conditions.

The term "derivatives" refers to chemical functional groups suitably substituted with protecting and/or activation groups or to activated forms of a corresponding chemical functional group which are known to the person skilled in the art. For example, activated forms of carboxyl groups include but are not limited to active esters, such as succinimidyl ester, benzotriazyl ester, nitrophenyl ester, pentafluorophenyl ester, azabenzotriazyl ester, acyl halogenides, mixed or symmetrical anhydrides, acyl imidazole.

The term "non-enzymatically cleavable linker" refers to linkers that are hydrolytically degradable under physiological conditions without enzymatic activity.

The terms "spacer", "spacer group", "spacer molecule", and "spacer moiety" are used interchangeably and if used to describe a moiety present in the hydrogel carrier of the invention, refer to any moiety suitable for connecting two moieties, such as $C_{1-50}$ alkyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—.

The terms "terminal", "terminus" or "distal end" refer to the position of a functional group or linkage within a molecule or moiety, whereby such functional group may be a chemical functional group and the linkage may be a degradable or permanent linkage, characterized by being located adjacent to or within a linkage between two moieties or at the end of an oligomeric or polymeric chain.

The phrases "in bound form" or "moiety" refer to substructures which are part of a larger molecule. The phrase "in bound form" is used to simplify reference to moieties by naming or listing reagents, starting materials or hypothetical starting materials well known in the art, and whereby "in bound form" means that for example one or more hydrogen radicals (—H), or one or more activating or protecting groups present in the reagents or starting materials are not present in the moiety.

It is understood that all reagents and moieties comprising polymeric moieties refer to macromolecular entities known to exhibit variabilities with respect to molecular weight, chain lengths or degree of polymerization, or the number of functional groups. Structures shown for crosslinking reagents, and crosslinked moieties are thus only representative examples.

A reagent or moiety may be linear or branched. If the reagent or moiety has two terminal groups, it is referred to as a linear reagent or moiety. If the reagent or moiety has more than two terminal groups, it is considered to be a branched or multi-functional reagent or moiety.

The linkers employed in such carrier-linked prodrugs are transient, meaning that they are non-enzymatically hydrolytically degradable (cleavable) under physiological conditions (aqueous buffer at pH 7.4, 37° C.) with half-lives ranging from, for example, one hour to three months.

The term "GLP-1/Glucagon agonist hydrogel prodrug" refers to carrier-linked prodrugs of GLP-1/Glucagon agonist, wherein the carrier is a hydrogel. The terms "hydrogel prodrug" and "hydrogel-linked prodrug" refer to prodrugs of biologically active agents transiently linked to a hydrogel and are used synonymously.

A "hydrogel" may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

"Free form" of a drug refers to a drug, specifically to GLP-1/Glucagon agonist, in its unmodified, pharmacologically active form, such as after being released from a polymer conjugate.

The terms "drug", "biologically active molecule", "biologically active moiety", "biologically active agent", "active agent", are used synonymously and refer to GLP-1/Glucagon agonist, either in its bound or free form.

A "therapeutically effective amount" of GLP-1/Glucagon agonist as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which are all within the ordinary skills of a trained physician.

"Stable" and "stability" means that within the indicated storage time the hydrogel conjugates remain conjugated and do not hydrolyze to a substantial extent and exhibit an acceptable impurity profile relating to GLP-1/Glucagon agonist. To be considered stable, the composition contains less than 5% of the drug in its free form.

The term "pharmaceutically acceptable" means approved by a regulatory agency such as the EMEA (Europe) and/or the FDA (US) and/or any other national regulatory agencies for use in animals, preferably in humans.

"Pharmaceutical composition" or "composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient (pharmaceutically acceptable carrier).

"Dry composition" means that the GLP-1/Glucagon agonist hydrogel prodrug composition is provided in a dry form in a container. Suitable methods for drying are for example spray-drying and lyophilization (freeze-drying). Such dry composition of GLP-1/Glucagon agonist hydrogel prodrug has a residual water content of a maximum of 10%, preferably less than 5% and more preferably less than 2% (determined according to Karl Fischer method). The preferred method of drying is lyophilization. "Lyophilized composition" means that the GLP-1/Glucagon agonist hydrogel polymer prodrug composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the addition of a liquid to a dry composition to bring it into the form of a liquid or suspension composition. It is understood that the term "reconstitution" is not limited to the addition of water, but refers to the addition of any liquid, including for example buffers or other aqueous solutions.

"Reconstitution solution" refers to the liquid used to reconstitute the dry composition of an GLP-1/Glucagon agonist hydrogel prodrug prior to administration to a patient in need thereof.

"Container" means any container in which the GLP-1/Glucagon agonist hydrogel prodrug composition is comprised and can be stored until reconstitution.

"Buffer" or "buffering agent" refers to chemical compounds that maintain the pH in a desired range. Physiologically tolerated buffers are, for example, sodium phosphate, succinate, histidine, bicarbonate, citrate and acetate, pyruvate. Antacids such as $Mg(OH)_2$ or $ZnCO_3$ may be also used. Buffering capacity may be adjusted to match the conditions most sensitive to pH stability.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as arginine, glycine, glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the polymer prodrug. Stabilisation is achieved by strengthening of the protein-stabilising forces, by destabilisation of the denatured state, or by direct binding of excipients to the protein.

"Anti-adsorption agents" refers to mainly ionic or non-ionic surfactants or other proteins or soluble polymers used to coat or adsorb competitively to the inner surface of the composition's container. Chosen concentration and type of excipient depends on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin E, chelating agents such aus citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"Sealing a container" means that the container is closed in such way that it is airtight, allowing no gas exchange between the outside and the inside and keeping the content sterile.

The term "reagent" or "precursor" refers to an intermediate or starting material used in the assembly process leading to a prodrug of the present invention.

An object of the invention is a prodrug or a pharmaceutically acceptable salt thereof comprising a drug linker conjugate of formula (I)

$$Z-L^1-L^2-L-Y-R^{20} \quad (I)$$

wherein Y is a peptide moiety having the formula (II)

(II)
His-X2-X3-Gly-Thr-Phe-Thr-Ser-Asp-Leu-Ser-Lys-

Gln-Leu-Asp-Glu-Gln-X18-Ala-X20-X21-Phe-Ile-Glu-

Trp-Leu-Ile-X28-Gly-Gly-Pro-X32-Ser-Gly-Ala-Pro-

Pro-Pro-Ser

X2 represents an amino acid residue selected from Ser, D-Ser and Aib,
X3 represents an amino acid residue selected from Gln and His,
X18 represents an amino acid residue selected from Arg and Lys
X20 represents an amino acid residue selected from Lys, Gln and His,
X21 represents an amino acid residue selected from Asp and Glu,
X28 represents an amino acid residue selected from Ser and Ala, X32 represents an amino acid residue selected from Ser and Val, or wherein Y is a peptide moiety having the formula (III)

(III)
His-X2-X3-Gly-Thr-Phe-Thr-Ser-Asp-Leu-Ser-Lys-

Gln-Leu-Asp-Glu-Gln-X18-Ala-X20-X21-Phe-Ile-Glu-

Trp-Leu-Ile-X28-Gly-Gly-Pro-X32-Ser-Gly-Ala-Pro-

Pro-Pro-Ser

X2 represents an amino acid residue selected from Ser, D-Ser and Aib,
X3 represents an amino acid residue selected from Gln and His,
X18 represents an amino acid residue selected from Leu and His
X20 represents an amino acid residue selected from His, Arg, Lys, and Gln,
X21 represents an amino acid residue selected from Asp and Glu,
X28 represents an amino acid residue selected from Lys, Ser and Ala,
X32 represents an amino acid residue selected from Ser and Val, or
wherein Y is a peptide moiety having the formula (IV)

(IV)
His-X2-X3-Gly-Thr-Phe-Thr-Ser-Asp-Leu-Ser-Lys-Leu-

Leu-Asp-Glu-Gln-X18-Ala-Lys-Asp-Phe-Ile-Glu-Trp-

Leu-Ile-Ala-Gly-Gly-Pro-X32-Ser-Gly-Ala-Pro-Pro-

Pro-Ser

X2 represents an amino acid residue selected from Ser, D-Ser and Aib,
X3 represents an amino acid residue selected from Gln and His,
X18 represents an amino acid residue selected from Arg and Leu,
X32 represents an amino acid residue selected from Ser and Val,
or a salt or solvate thereof;
or a salt or solvate thereof;
$R^{20}$ is OH or $NH_2$;
L is a linker of formula (Ia),

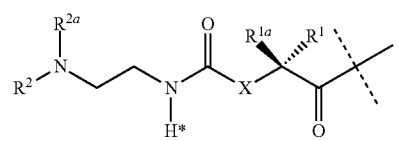

wherein the dashed line indicates the attachment to the N-Terminus of Y by forming an amide bond;
X is $C(R^4R^{4a})$; $N(R^4)$;
$R^1$, $R^{1a}$, are independently selected from the group consisting of H; and $C_{1-4}$ alkyl;
$R^2$, $R^{2a}$, are independently selected from the group consisting of H; and $C_{1-4}$ alkyl;

$R^4$, $R^{4a}$, are independently selected from the group consisting of H; and $C_{1-4}$ alkyl;
wherein $R^2$, $R^{2a}$, $R^4$ or $R^{4a}$ is substituted with one group $L^2$-$L^1$-Z; wherein
$L^2$ is a single chemical bond or is a $C_{1-20}$ alkyl chain, which is optionally interrupted by one or more groups independently selected from —O— and $C(O)N(R^{3aa})$ and is optionally substituted with one or more groups independently selected from OH and $C(O)N(R^{3aa}R^{3aaa})$, wherein $R^{3aa}$ and $R^{3aaa}$ are independently selected from the group consisting of H and $C_{1-4}$ alkyl; and
$L^2$ is attached to $L^1$ via a terminal group selected from the group consisting of

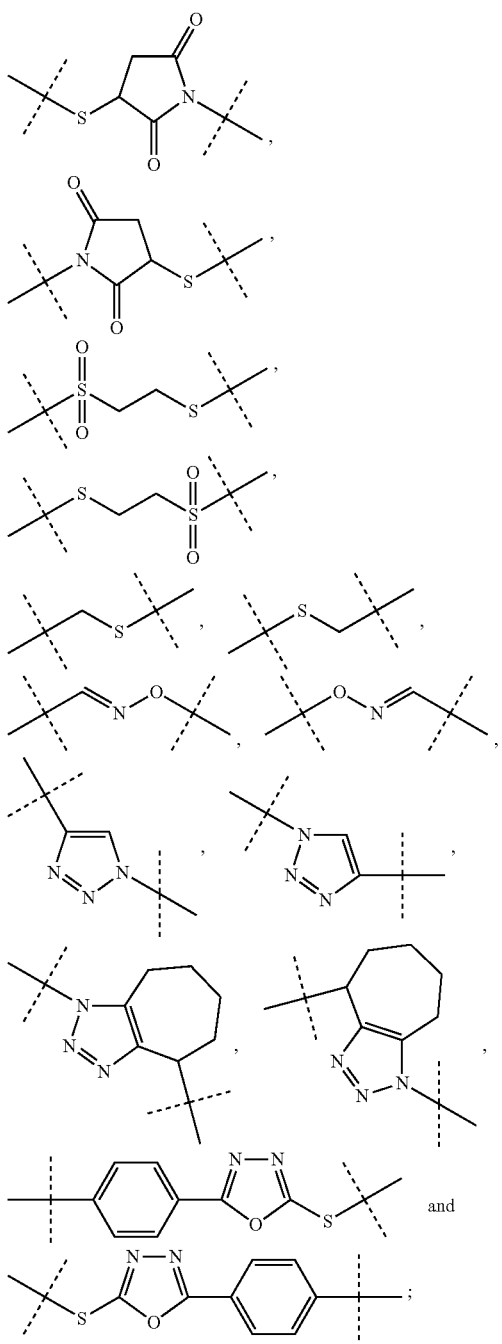

and wherein $L^2$ is attached to the one position indicated with the dashed line and $L^1$ is attached to the position indicated with the other dashed line; and
$L^1$ is a $C_{1-20}$ alkyl chain, which is optionally interrupted by one or more groups independently selected from —O— and $C(O)N(R^{5aa})$ and is optionally substituted with one or more groups independently selected from OH and $C(O)N(R^{5aa}R^{5aaa})$, wherein $R^{5aa}$ and $R^{5aaa}$ are independently selected from the group consisting of H and $C_{1-4}$ alkyl; and
$L^1$ is attached to Z via a terminal amino group forming an amide bond with the carboxy group of the beta-1,3-D-glucuronic acid of the hyaluronic acid of Z;
Z is a crosslinked hyaluronic acid hydrogel, in which
0.05 to 20% of the monomeric disaccharide units are crosslinked by a crosslinker; and
0.2 to 8.5% of the monomeric disaccharide units bear $L^1$-$L^2$-L-Y—$R^{20}$.groups.
Further embodiments of L, $L^1$, $L^2$, Z and Y.
In another embodiment
L is a linker moiety of formula (Ib),

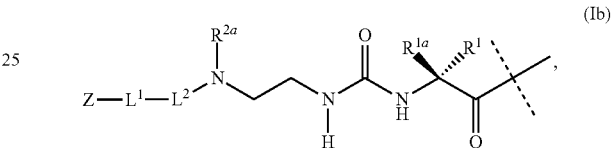

(Ib)

wherein the dashed line indicates attachment to Y by forming an amide bond;
$R^1$, $R^{1a}$, $R^{2a}$ are selected independently from the group consisting of H and $C_{1-4}$ alkyl;
$L^2$-$L^1$-Z is defined as described above.
In another embodiment
L is a linker moiety of formula (Ib), wherein
$R^1$ is $CH_3$;
$R^{1a}$ is H;
$R^{2a}$ is H; and
$L^2$-$L^1$-Z is defined as described above.
In another embodiment
L is a linker moiety of formula (Ib), wherein
$R^1$ is H;
$R^{1a}$ is $CH_3$;
$R^{2a}$ is H; and
$L^2$-$L^1$-Z is defined as described above.
In another embodiment
L is a linker moiety of formula (Ib), wherein
$R^1$ is $CH_3$;
$R^{1a}$ is $CH_3$;
$R^{2a}$ is H; and
$L^2$-$L^1$-Z is defined as described above.
In another embodiment
L is a linker moiety -L of formula (Ic),

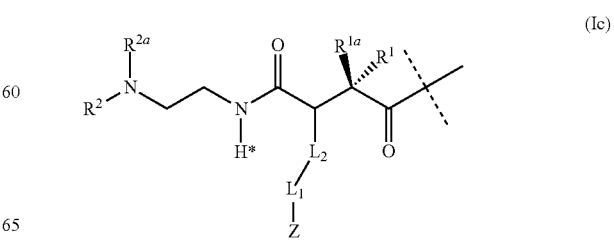

(Ic)

wherein the dashed line indicates attachment to Y by forming an amide bond;
R¹ is selected from H or $C_{1-4}$ alkyl, preferably H;
$R^{1a}$ is selected from H or $C_{1-4}$ alkyl, preferably H;
$R^2$, $R^{2a}$ are independently selected from the group consisting of H and $C_{1-4}$ alkyl;
wherein $L^2$-$L^1$-Z is defined as described above.

In another embodiment
L is a linker moiety -L of formula (Ic),

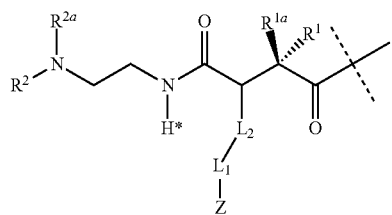

(Ic)

wherein the dashed line indicates attachment to Y by forming an amide bond;
R¹ and $R^{1a}$ are H;
$R^2$, $R^{2a}$ are independently selected from the group consisting of H and $CH_3$;
wherein $L^2$-$L^1$-Z is defined as described above.

In another embodiment
L is a linker moiety -L of formula (Ic), wherein
R¹ and $R^{1a}$ are H;
$R^2$ is H and $R^{2a}$ is $CH_3$;
wherein $L^2$-$L^1$-Z is defined as described above.

In another embodiment
$L^2$ is a $C_{1-10}$ alkyl chain, which is optionally interrupted by one or two groups independently selected from —O— and $C(O)N(R^{3aa})$ and, wherein $R^{3aa}$ is independently selected from the group consisting of H and $C_{1-4}$ alkyl; and
$L^2$ is attached to $L^1$ via a terminal group selected from the group consisting of

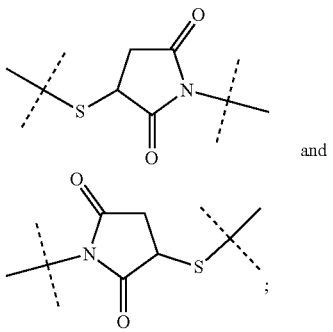

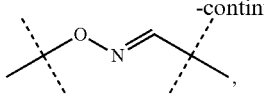

wherein $L^2$ is attached to the one position indicated with the dashed line and
$L^1$ is attached to the position indicated with the other dashed line; and In another embodiment
$L^2$ is a $C_{1-6}$ alkyl chain, which is optionally interrupted by one group selected from —O— and $C(O)N(R^{3aa})$ and, wherein $R^{3aa}$ is independently selected from the group consisting of H and $C_{1-4}$ alkyl; and
$L^2$ is attached to $L^1$ via a terminal group selected from the group consisting of

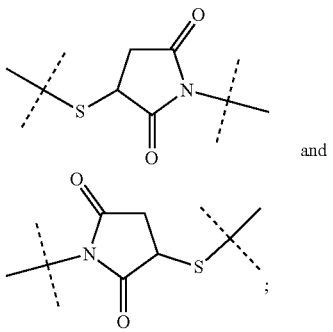

and wherein $L^2$ is attached to the one position indicated with the dashed line and $L^1$ is attached to the position indicated with the other dashed line.

In another embodiment
$L^2$ is —$CH_2$—$CH_2$—$CH_2$—$CH_2$—$CH_2$—C(O)NH— or —$CH_2$—$CH_2$—$CH_2$—$CH_2$—$CH_2$—$CH_2$— and is attached to $L^1$ via the terminal group

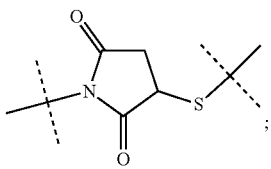

wherein $L^2$ is attached to the Sulfur atom indicated with the dashed line and $L^1$ is attached to nitrogen atom indicated with the dashed line.

In another embodiment
$L^1$ is a $C_{1-10}$ alkyl chain, with an amino group on one distal end, which is optionally interrupted by one or two groups independently selected from —O— and $C(O)N(R^{5aa})$ and, wherein $R^{5aa}$ is independently selected from the group consisting of H and $C_{1-4}$ alkyl.

A further embodiment relates to prodrugs, wherein
Z is a crosslinked hyaluronic acid hydrogel, in which 0.05 to 15% of the monomeric disaccharide units are crosslinked by a crosslinker.

A further embodiment relates to prodrugs, wherein
Z is a crosslinked hyaluronic acid hydrogel, in which 1 to 10% of the monomeric disaccharide units are crosslinked by a crosslinker.

A further embodiment relates to prodrugs, wherein Z is a crosslinked hyaluronic acid hydrogel, in which 0.2 to 8.5% of the monomeric disaccharide units bear $L^1$-$L^2$-L-Y—$R^{20}$.groups.

A further embodiment relates to prodrugs, wherein Z is a crosslinked hyaluronic acid hydrogel, in which 0.2 to 6% of the monomeric disaccharide units bear $L^1$-$L^2$-L-Y—$R^{20}$.groups.

A further embodiment relates to prodrugs, wherein Z is a crosslinked hyaluronic acid hydrogel, in which 0.2 to 5% of the monomeric disaccharide units bear $L^1$-$L^2$-L-Y—$R^{20}$.groups.

A further embodiment relates to prodrugs, wherein Z is a crosslinked hyaluronic acid hydrogel, in which 0.4 to 4% of the monomeric disaccharide units bear $L^1$-$L^2$-L-Y—$R^{20}$.groups.

In another embodiment the GLP-1/Glucagon agonist prodrug has a structure as represented by formula (V)

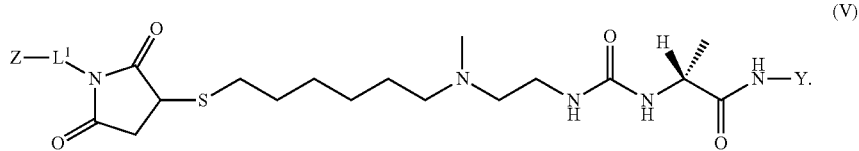

(V)

In another embodiment the GLP-1/Glucagon agonist prodrug has a structure as represented by formula (VI) (Aib-linker)

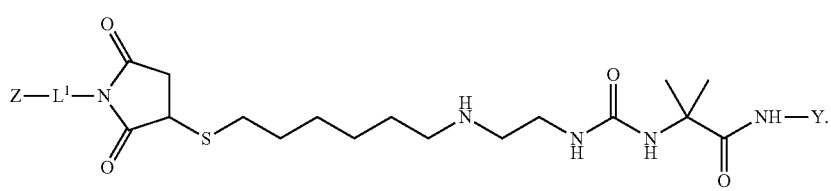

(VI)

In another embodiment the GLP-1/Glucagon agonist prodrug has a structure as represented by formula (VII)

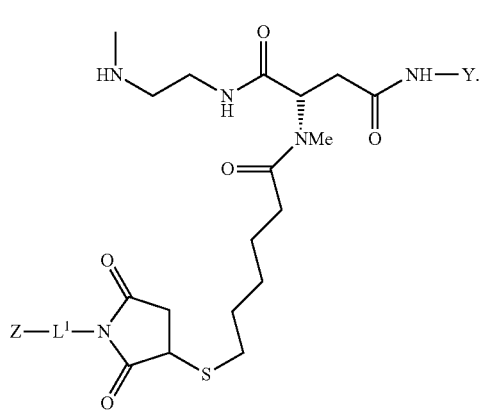

(VII)

A further embodiment relates to a group of prodrugs having a peptide moiety Y of formula (II), wherein
X2 represents an amino acid residue selected from Ser, D-Ser and Aib,
X3 represents an amino acid residue selected from Gln and His,
X18 represents Arg
X20 represents an amino acid residue selected from Lys, Gln and His,
X21 represents an amino acid residue selected from Asp and Glu,
X28 represents an amino acid residue selected from Ser and Ala,
X32 represents an amino acid residue selected from Ser and Val.

A further embodiment relates to a group of prodrugs having a peptide moiety Y of formula (II), wherein
X2 represents an D-Ser
X3 represents His,
X18 represents Arg
X20 represents Lys,
X21 represents an amino acid residue selected from Asp and Glu,
X28 represents an amino acid residue selected from Ser and Ala,
X32 represents an amino acid residue selected from Ser and Val.

A further embodiment relates to a group of prodrugs having a peptide moiety Y of formula (II), wherein
X2 represents D-Ser,
X3 represents an amino acid residue selected from Gln and His,
X18 represents Arg,
X20 represents Lys,
X21 represents an amino acid residue selected from Asp and Glu,
X28 represents Ala,
X32 represents an amino acid residue selected from Ser and Val.

A further embodiment relates to a group of prodrugs having a peptide moiety Y of formula (II), wherein
X2 represents an amino acid residue selected from Ser, D-Ser and Aib,
X3 represents His,
X18 represents Arg,
X20 represents Lys,
X21 represents Asp, X28 represents Ala,
X32 represents an amino acid residue selected from Ser and Val.

A further embodiment relates to a group of prodrugs having a peptide moiety Y of formula (II), wherein
X2 represents an amino acid residue selected from Ser, D-Ser and Aib,
X3 represents an amino acid residue selected from Gln and His,
X18 represents an amino acid residue selected from Arg and Lys,
X20 represents Lys,
X21 represents an amino acid residue selected from Asp and Glu,
X28 represents an amino acid residue selected from Ser and Ala,
X32 represents an amino acid residue selected from Ser and Val.

A further embodiment relates to a group of prodrugs having a peptide moiety Y of formula (II), wherein
X2 represents an amino acid residue selected from Ser, D-Ser and Aib,
X3 represents an amino acid residue selected from Gln and His,
X18 represents an amino acid selected from Arg and Lys,
X20 represents an amino acid residue selected from Lys, Gln and His,
X21 represents Asp,
X28 represents an amino acid residue selected from Ser and Ala,
X32 represents an amino acid residue selected from Ser and Val.

A further embodiment relates to a group of prodrugs having a peptide moiety Y of formula (II), wherein
X2 represents an amino acid residue selected from Ser, D-Ser and Aib,
X3 represents an amino acid residue selected from Gln and His,
X18 represents an amino acid selected from Arg and Lys,
X20 represents an amino acid residue selected from Lys, Gln and His,
X21 represents an amino acid residue selected from Asp and Glu,
X28 represents an amino acid residue selected from Ser and Ala,
X32 represents Ser.

A further embodiment relates to a group of prodrugs having a peptide moiety Y of formula (II), wherein
X2 represents an amino acid residue selected from Ser, D-Ser and Aib,
X3 represents an amino acid residue selected from Gln and His,
X18 represents Arg
X20 represents Lys,
X21 represents an amino acid residue selected from Asp and Glu,
X28 represents Ala,
X32 represents Val.

A further embodiment relates to a group of prodrugs having a peptide moiety Y of formula (III), wherein
X2 represents an amino acid residue selected from Ser, D-Ser and Aib,
X3 represents an amino acid residue selected from Gln and His,
X18 represents Leu
X20 represents an amino acid residue selected from His, Arg, Lys and Gln,
X21 represents an amino acid residue selected from Asp and Glu,
X28 represents an amino acid residue selected from Lys, Ser and Ala,
X32 represents an amino acid residue selected from Ser and Val.

A further embodiment relates to a group of prodrugs having a peptide moiety Y of formula (III), wherein
X2 represents Aib,
X3 represents an amino acid residue selected from Gln and His,
X18 represents an amino acid residue selected from His and Leu;
X20 represents an amino acid residue selected from His, Arg, Lys and Gln,
X21 represents an amino acid residue selected from Asp and Glu,
X28 represents an amino acid residue selected from Lys, Ser and Ala,
X32 represents an amino acid residue selected from Ser and Val.

A further embodiment relates to a group of prodrugs having a peptide moiety Y of formula (III), wherein
X2 represents Aib,
X3 represents His,
X18 represents Leu,
X20 represents Lys,
X21 represents an amino acid residue selected from Asp and Glu,
X28 represents an amino acid residue selected from Ser and Ala,
X32 represents an amino acid residue selected from Ser and Val.

A further embodiment relates to a group of prodrugs having a peptide moiety Y of formula (III), wherein
X2 represents an amino acid residue selected from Ser, D-Ser and Aib,
X3 represents His,
X18 represents an amino acid residue selected from His and Leu,
X20 represents an amino acid residue selected from His, Arg, Lys and Gln,
X21 represents an amino acid residue selected from Asp and Glu,
X28 represents an amino acid residue selected from Lys, Ser and Ala,
X32 represents an amino acid residue selected from Ser and Val.

A further embodiment relates to a group of prodrugs having a peptide moiety Y of formula (III), wherein
X2 represents an amino acid residue selected from Ser, D-Ser and Aib,
X3 represents Gln,
X18 represents Leu,
X20 represents Lys,
X21 represents an amino acid residue selected from Asp and Glu,
X28 represents Ala,
X32 represents Ser.

A further embodiment relates to a group of prodrugs having a peptide moiety Y of formula (III), wherein
X2 represents an amino acid residue selected from Ser, D-Ser and Aib,
X3 represents an amino acid residue selected from Gln and His,
X18 represents an amino acid residue selected from His and Leu, X20 represents Lys,
X21 represents an amino acid residue selected from Asp and Glu,
X28 represents an amino acid residue selected from Lys, Ser and Ala,
X32 represents an amino acid residue selected from Ser and Val.

A further embodiment relates to a group of prodrugs having a peptide moiety Y of formula (III), wherein
X2 represents an amino acid residue selected from Ser, D-Ser and Aib,
X3 represents an amino acid residue selected from Gln and His,
X18 represents an amino acid residue selected from His and Leu,
X20 represents an amino acid residue selected from His, Arg, Lys and Gln,
X21 represents Asp,
X28 represents an amino acid residue selected from Lys, Ser and Ala,
X32 represents an amino acid residue selected from Ser and Val.

A further embodiment relates to a group of prodrugs having a peptide moiety Y of formula (III), wherein
X2 represents Aib,
X3 represents an amino acid residue selected from Gln and His,
X18 represents Leu,
X20 represents an amino acid residue selected from Lys and Gln,
X21 represents Glu,
X28 represents Ala,
X32 represents Ser.

A further embodiment relates to a group of prodrugs having a peptide moiety Y of formula (III), wherein
X2 represents an amino acid residue selected from Ser, D-Ser and Aib,
X3 represents an amino acid residue selected from Gln and His,
X18 represents an amino acid residue selected from His and Leu,
X20 represents an amino acid residue selected from His, Arg, Lys and Gln,
X21 represents an amino acid residue selected from Asp and Glu,
X28 represents Ala,
X32 represents an amino acid residue selected from Ser and Val.

A further embodiment relates to a group of prodrugs having a peptide moiety Y of formula (III), wherein
X2 represents an amino acid residue selected from Ser, D-Ser and Aib,
X3 represents an amino acid residue selected from Gln and His,
X18 represents an amino acid residue selected from His and Leu,
X20 represents an amino acid residue selected from His, Arg, Lys and Gln,
X21 represents an amino acid residue selected from Asp and Glu,
X28 represents an amino acid residue selected from Lys, Ser and Ala,
X32 represents an amino acid residue selected from Ser and Val.

A further embodiment relates to a group of prodrugs having a peptide moiety Y of formula (II) or (III), wherein
X2 represents an amino acid residue selected from Aib and D-Ser,
X3 represents His,
X18 represents an amino acid residue selected from Asp and Glu,
X28 represents an amino acid residue selected from Leu and Arg,
X20 represents Lys,
X21 represents an amino acid residue selected from Asp and Glu,
X28 represents an amino acid residue selected from Ser and Ala,
X32 represents an amino acid residue selected from Ser and Val.

A further embodiment relates to a group of prodrugs having a peptide moiety of formula (IV), wherein
X2 represents D-Ser,
X3 represents an amino acid residue selected from Gln and His,
X18 represents an amino acid residue selected from Arg and Leu,
X32 represents an amino acid residue selected from Ser and Val.

A further embodiment relates to a group of prodrugs having a peptide moiety of formula (IV), wherein
X2 represents an amino acid residue selected from Ser, D-Ser and Aib,
X3 represents His,
X18 represents an amino acid residue selected from Arg and Leu, particularly Leu,
X32 represents an amino acid residue selected from Ser and Val.

A further embodiment relates to a group of prodrugs having a peptide moiety of formula (IV), wherein
X2 represents D-Ser,
X3 represents Gln,
X18 represents Arg,
X32 represents an amino acid residue selected from Ser and Val.

A further embodiment relates to a group of prodrugs having a peptide moiety of formula (IV), wherein
X2 represents an amino acid residue selected from Ser, D-Ser and Aib,
X3 represents an amino acid residue selected from Gln and His,
X18 represents an amino acid residue selected from Arg and Leu,
X32 represents Ser.

A further embodiment relates to a group of prodrugs having a peptide moiety of formula (IVa)

$$
\text{H}_2\text{N-His-Aib-His-Gly-Thr-Phe-Thr-Ser-Asp-Leu-Ser-Lys-Gln-Leu-X15-Glu-Gln-Leu-Ala-Arg-Asp-Phe-Ile-Glu-Trp-Leu-Ile-Bal-X29-Gly-X31-X32-Ser-X34-X35-Pro-Pro-Pro-X39-R}^{20} \tag{IVa}
$$

wherein
X15 represents an amino acid residue selected from Asp and Glu, (pref. Asp)
X29 represents an amino acid residue selected from Gly, D-Ala and Pro, (pref) Gly, D-Ala
X31 represents an amino acid residue selected from Pro, His and Trp, (pref. Pro)

X32 represents an amino acid residue selected from Ser,
  His, Pro and Arg, (pref. Ser, His, Pro),
X34 represents an amino acid residue selected from Gly
  and D-Ala,
X35 represents an amino acid residue selected from Ala,
  Pro and Lys, (pref. Ala, Pro)
X39 represents Ser or Pro-Pro-Pro,
or a salt or solvate thereof.

A further embodiment relates to a group of prodrugs having a peptide moiety of formula (IVa), wherein
  X15 represents Asp,
  X29 represents an amino acid residue selected from Gly, D-Ala and Pro,
  X31 represents an amino acid residue selected from Pro, His and Trp,
  X32 represents an amino acid residue selected from Ser, His, Pro and Arg,
  X34 represents an amino acid residue selected from Gly and D-Ala,
  X35 represents an amino acid residue selected from Ala, Pro and Lys,
  X39 represents Ser.

A further embodiment relates to a group of prodrugs having a peptide moiety of formula (IVa), wherein
  X15 represents an amino acid residue selected from Asp and Glu,
  X29 represents Gly,
  X31 represents an amino acid residue selected from Pro, His and Trp,
  X32 represents an amino acid residue selected from Ser, His, Pro and Arg,
  X34 represents an amino acid residue selected from Gly and D-Ala,
  X35 represents an amino acid residue selected from Ala, Pro and Lys,
  X39 represents Ser or Pro-Pro-Pro.

A further embodiment relates to a group of prodrugs having a peptide moiety of formula (IVa), wherein
  X15 represents an amino acid residue selected from Asp and Glu,
  X29 represents Gly,
  X31 represents Pro,
  X32 represents an amino acid residue selected from Ser, His and Pro,
  X34 represents Gly,
  X35 represents Ala,
  X39 represents Ser.

A further embodiment relates to a group of prodrugs having a peptide moiety of formula (IVa), wherein
  X15 represents Asp,
  X29 represents D-Ala,
  X31 represents Pro,
  X32 represents Pro,
  X34 represents D-Ala,
  X35 represents an amino acid residue selected from Ala and Pro,
  X39 represents Ser or Pro-Pro-Pro.

A further embodiment relates to a group of prodrugs having a peptide moiety of formula (IVa), wherein
  X15 represents an amino acid residue selected from Asp and Glu,
  X29 represents an amino acid residue selected from Gly, D-Ala and Pro,
  X31 represents Pro,
  X32 represents an amino acid residue selected from Ser, His, Pro and Arg,
  X34 represents an amino acid residue selected from Gly and D-Ala,
  X35 represents an amino acid residue selected from Ala, Pro and Lys,
  X39 represents Ser or Pro-Pro-Pro.

A further embodiment relates to a group of prodrugs having a peptide moiety of formula (IVa), wherein
  X15 represents Asp,
  X29 represents Gly,
  X31 represents His,
  X32 represents Pro,
  X34 represents Gly,
  X35 represents an amino acid residue selected from Ala and Lys,
  X39 represents Ser.

A further embodiment relates to a group of prodrugs having a peptide moiety of formula (IVa), wherein
  X15 represents Asp,
  X29 represents an amino acid residue selected from Gly and Pro,
  X31 represents Pro,
  X32 represents Ser,
  X34 represents Gly,
  X35 represents Ala,
  X39 represents Ser.

A further embodiment relates to a group of prodrugs having a peptide moiety of formula (IVa), wherein
  X15 represents an amino acid residue selected from Asp and Glu,
  X29 represents an amino acid residue selected from Gly, D-Ala and Pro,
  X31 represents an amino acid residue selected from Pro, His and Trp,
  X32 represents Pro,
  X34 represents an amino acid residue selected from Gly and D-Ala,
  X35 represents an amino acid residue selected from Ala, Pro and Lys,
  X39 represents Ser or Pro-Pro-Pro.

A further embodiment relates to a group of prodrugs having a peptide moiety of formula (IVa), wherein
  X15 represents Asp,
  X29 represents an amino acid residue selected from Gly and Pro,
  X31 represents Pro,
  X32 represents His,
  X34 represents Gly,
  X35 represents Ala,
  X39 represents Ser.

A further embodiment relates to a group of prodrugs having a peptide moiety of formula (IVa), wherein
  X15 represents an amino acid residue selected from Asp and Glu,
  X29 represents an amino acid residue selected from Gly, D-Ala and Pro,
  X31 represents an amino acid residue selected from Pro, His and Trp,
  X32 represents an amino acid residue selected from Ser, His, Pro and Arg,
  X34 represents Gly,
  X35 represents an amino acid residue selected from Ala, Pro and Lys,
  X39 represents Ser or Pro-Pro-Pro.

A further embodiment relates to a group of prodrugs having a peptide moiety of formula (IVa), wherein
  X15 represents Asp,
  X29 represents D-Ala, X31 represents Pro,
X32 represents an amino acid residue selected from Ser and Pro,
X34 represents D-Ala,
X35 represents an amino acid residue selected from Ala and Pro,
X39 represents Ser or Pro-Pro-Pro.

A further embodiment relates to a group of prodrugs having a peptide moiety of formula (IVa), wherein
X15 represents an amino acid residue selected from Asp and Glu,
X29 represents an amino acid residue selected from Gly, D-Ala and Pro,
X31 represents an amino acid residue selected from Pro, His and Trp,
X32 represents an amino acid residue selected from Ser, His, Pro and Arg,
X34 represents an amino acid residue selected from Gly and D-Ala,
X35 represents Ala,
X39 represents Ser.

A further embodiment relates to a group of prodrugs having a peptide moiety of formula (IVa), wherein
X15 represents Asp,
X29 represents Gly,
X31 represents an amino acid residue selected from Pro and His,
X32 represents Pro,
X34 represents Gly,
X35 represents Lys,
X39 represents Ser.

A further embodiment relates to a group of prodrugs having a peptide moiety of formula (IVa), wherein
X15 represents Asp,
X29 represents an amino acid residue selected from Gly and D-Ala,
X31 represents Pro,
X32 represents Pro,
X34 represents an amino acid residue selected from Gly and D-Ala,
X35 represents Pro,
X39 represents Pro-Pro-Pro.

A further embodiment relates to a group of prodrugs having a peptide moiety of formula (IVa), wherein
X15 represents an amino acid residue selected from Asp and Glu,
X29 represents an amino acid residue selected from Gly, D-Ala and Pro,
X31 represents an amino acid residue selected from Pro, His and Trp,
X32 represents an amino acid residue selected from Ser, His, Pro and Arg,
X34 represents an amino acid residue selected from Gly and D-Ala,
X35 represents an amino acid residue selected from Ala, Pro and Lys,
X39 represents Ser.

In one embodiment Y refers to an GLP-1/Glucagon agonist of Seq. ID No 60.

In one embodiment Y refers to an GLP-1/Glucagon agonist selected from sequences Seq. ID No 4 to 60.

In one embodiment Y refers to an GLP-1/Glucagon agonist selected from sequences Seq. ID No 4 to 44.

In one embodiment Y refers to an GLP-1/Glucagon agonist selected from sequences Seq. ID No 4 to 22.

In one embodiment Y refers to an GLP-1/Glucagon agonist selected from sequences Seq. ID No 23 to 39.

In one embodiment Y refers to an GLP-1/Glucagon agonist selected from sequences Seq. ID No 40 to 44.

In one embodiment Y refers to an GLP-1/Glucagon agonist selected from sequences Seq. ID No 45 to 59.

In one embodiment Y refers to an GLP-1/Glucagon agonist selected from sequences Seq. ID No 18, 21 and 26.

In one embodiment Y refers to an GLP-1/Glucagon agonist selected from sequences Seq. ID No 18, 21, 26, 45, 48, 49 and 60.

TABLE 1

| SEQ ID | sequence |
|---|---|
| 1 | H-G-E-G-T-F-T-S-D-L-S-K-Q-M-E-E-A-V-R-L-F-I-E-W-L-K-N-G-G-P-S-S-G-A-P-P-P-S-NH2 |
| 2 | H-A-E-G-T-F-T-S-D-V-S-S-Y-L-E-G-Q-A-A-K-E-F-I-A-W-L-V-K-G-R-NH2 |
| 3 | H-S-Q-G-T-F-T-S-D-Y-S-K-Y-L-D-S-R-R-A-Q-D-F-V-Q-W-L-M-N-T |
| 4 | H-S-Q-G-T-F-T-S-D-L-S-K-Q-L-D-E-Q-R-A-K-E-F-I-E-W-L-I-A-G-G-P-S-S-G-A-P-P-P-S-NH2 |
| 5 | H-S-Q-G-T-F-T-S-D-L-S-K-Q-L-D-E-Q-R-A-K-E-F-I-E-W-L-I-A-G-G-P-V-S-G-A-P-P-P-S-NH2 |
| 6 | H-dSer-Q-G-T-F-T-S-D-L-S-K-Q-L-D-E-Q-R-A-K-D-F-I-E-W-L-I-A-G-G-P-S-S-G-A-P-P-P-S-NH2 |
| 7 | H-dSer-Q-G-T-F-T-S-D-L-S-K-Q-L-D-E-Q-R-A-K-D-F-I-E-W-L-I-A-G-G-P-V-S-G-A-P-P-P-S-NH2 |
| 8 | H-Aib-H-G-T-F-T-S-D-L-S-K-Q-L-D-E-Q-R-A-K-D-F-I-E-W-L-I-A-G-G-P-S-S-G-A-P-P-P-S-NH2 |
| 9 | H-Aib-Q-G-T-F-T-S-D-L-S-K-Q-L-D-E-Q-R-A-Q-D-F-I-E-W-L-I-A-G-G-P-S-S-G-A-P-P-P-S-NH2 |
| 10 | H-Aib-Q-G-T-F-T-S-D-L-S-K-Q-L-D-E-Q-R-A-K-D-F-I-E-W-L-I-S-G-G-P-S-S-G-A-P-P-P-S-NH2 |

TABLE 1 -continued

| SEQ ID | sequence |
|---|---|
| 11 | H-Aib-Q-G-T-F-T-S-D-L-S-K-Q-L-D-E-Q-R-A-K-D-F-I-E-W-L-I-A-G-G-P-S-S-G-A-P-P-P-S-NH2 |
| 12 | H-Aib-Q-G-T-F-T-S-D-L-S-K-Q-L-D-E-Q-R-A-H-D-F-I-E-W-L-I-A-G-G-P-S-S-G-A-P-P-P-S-NH2 |
| 13 | H-Aib-Q-G-T-F-T-S-D-L-S-K-Q-L-D-E-Q-R-A-K-E-F-I-E-W-L-I-A-G-G-P-S-S-G-A-P-P-P-S-NH2 |
| 14 | H-Aib-Q-G-T-F-T-S-D-L-S-K-Q-L-D-E-Q-R-A-K-D-F-I-E-W-L-I-A-G-G-P-V-S-G-A-P-P-P-S-NH2 |
| 15 | H-Aib-Q-G-T-F-T-S-D-L-S-K-Q-L-D-E-Q-R-A-Q-D-F-I-E-W-L-I-S-G-G-P-S-S-G-A-P-P-P-S-NH2 |
| 16 | H-S-H-G-T-F-T-S-D-L-S-K-Q-L-D-E-Q-R-A-K-D-F-I-E-W-L-I-A-G-G-P-V-S-G-A-P-P-P-S-NH2 |
| 17 | H-dSer-Q-G-T-F-T-S-D-L-S-K-Q-L-D-E-Q-R-A-K-E-F-I-E-W-L-I-A-G-G-P-V-S-G-A-P-P-P-S-NH2 |
| 18 | H-dSer-H-G-T-F-T-S-D-L-S-K-Q-L-D-E-Q-R-A-K-D-F-I-E-W-L-I-A-G-G-P-V-S-G-A-P-P-P-S-NH2 |
| 19 | H-S-Q-G-T-F-T-S-D-L-S-K-Q-L-D-E-Q-R-A-K-D-F-I-E-W-L-I-A-G-G-P-V-S-G-A-P-P-P-S-NH2 |
| 20 | H-Aib-Q-G-T-F-T-S-D-L-S-K-Q-L-D-E-Q-R-A-K-E-F-I-E-W-L-I-S-G-G-P-S-S-G-A-P-P-P-S-NH2 |
| 21 | H-dSer-H-G-T-F-T-S-D-L-S-K-Q-L-D-E-Q-R-A-K-D-F-I-E-W-L-I-A-G-G-P-S-S-G-A-P-P-P-S-NH2 |
| 22 | H-dSer-Q-G-T-F-T-S-D-L-S-K-Q-L-D-E-Q-K-A-K-D-F-I-E-W-L-I-A-G-G-P-S-S-G-A-P-P-P-S- |
| 23 | H-Aib-H-G-T-F-T-S-D-L-S-K-Q-L-D-E-Q-L-A-R-D-F-I-E-W-L-I-A-G-G-P-S-S-G-A-P-P-P-S-NH2 |
| 24 | H-Aib-H-G-T-F-T-S-D-L-S-K-Q-L-D-E-Q-L-A-H-D-F-I-E-W-L-I-A-G-G-P-S-S-G-A-P-P-P-S-NH2 |
| 25 | H-dSer-Q-G-T-F-T-S-D-L-S-K-Q-L-D-E-Q-L-A-K-D-F-I-E-W-L-I-A-G-G-P-S-S-G-A-P-P-P-S-NH2 |
| 26 | H-Aib-H-G-T-F-T-S-D-L-S-K-Q-L-D-E-Q-L-A-K-D-F-I-E-W-L-I-A-G-G-P-S-S-G-A-P-P-P-S-NH2 |
| 27 | H-S-H-G-T-F-T-S-D-L-S-K-Q-L-D-E-Q-L-A-K-D-F-I-E-W-L-I-A-G-G-P-S-S-G-A-P-P-P-S-NH2 |
| 28 | H-S-Q-G-T-F-T-S-D-L-S-K-Q-L-D-E-Q-L-A-K-D-F-I-E-W-L-I-A-G-G-P-S-S-G-A-P-P-P-S-NH2 |
| 29 | H-Aib-H-G-T-F-T-S-D-L-S-K-Q-L-D-E-Q-L-A-K-E-F-I-E-W-L-I-A-G-G-P-S-S-G-A-P-P-P-S-NH2 |
| 30 | H-Aib-H-G-T-F-T-S-D-L-S-K-Q-L-D-E-Q-L-A-K-D-F-I-E-W-L-I-S-G-G-P-S-S-G-A-P-P-P-S-NH2 |
| 31 | H-Aib-H-G-T-F-T-S-D-L-S-K-Q-L-D-E-Q-L-A-K-D-F-I-E-W-L-I-K-G-G-P-S-S-G-A-P-P-P-S-NH2 |
| 32 | H-Aib-H-G-T-F-T-S-D-L-S-K-Q-L-D-E-Q-L-A-K-D-F-I-E-W-L-I-A-G-G-P-V-S-G-A-P-P-P-S-NH2 |
| 33 | H-dSer-H-G-T-F-T-S-D-L-S-K-Q-L-D-E-Q-L-A-K-D-F-I-E-W-L-I-A-G-G-P-S-S-G-A-P-P-P-S-NH2 |
| 34 | H-S-H-G-T-F-T-S-D-L-S-K-Q-L-D-E-Q-L-A-K-D-F-I-E-W-L-I-A-G-G-P-S-S-G-A-P-P-P-S-NH2 |
| 35 | H-Aib-Q-G-T-F-T-S-D-L-S-K-Q-L-D-E-Q-L-A-K-E-F-I-E-W-L-I-A-G-G-P-S-S-G-A-P-P-P-S-NH2 |

TABLE 1 -continued

| SEQ ID | sequence |
|---|---|
| 36 | H-Aib-Q-G-T-F-T-S-D-L-S-K-Q-L-D-E-Q-L-A-K-D-F-I-E-W-L-I-A-G-G-P-S-S-G-A-P-P-P-S-NH2 |
| 37 | H-Aib-H-G-T-F-T-S-D-L-S-K-Q-L-D-E-Q-H-A-K-D-F-I-E-W-L-I-A-G-G-P-S-S-G-A-P-P-P-S-NH2 |
| 38 | H-Aib-H-G-T-F-T-S-D-L-S-K-Q-L-D-E-Q-L-A-Q-D-F-I-E-W-L-I-A-G-G-P-S-S-G-A-P-P-P-S-NH2 |
| 39 | H-Aib-Q-G-T-F-T-S-D-L-S-K-Q-L-D-E-Q-L-A-Q-E-F-I-E-W-L-I-A-G-G-P-S-S-G-A-P-P-P-S-NH2 |
| 40 | H-dSer-Q-G-T-F-T-S-D-L-S-K-L-L-D-E-Q-R-A-K-D-F-I-E-W-L-I-A-G-G-P-S-S-G-A-P-P-P-S-NH2 |
| 41 | H-Aib-H-G-T-F-T-S-D-L-S-K-L-L-D-E-Q-L-A-K-D-F-I-E-W-L-I-A-G-G-P-S-S-G-A-P-P-P-S-NH2 |
| 42 | H-dSer-Q-G-T-F-T-S-D-L-S-K-L-L-D-E-Q-R-A-K-D-F-I-E-W-L-I-A-G-G-P-V-S-G-A-P-P-P-S-NH2 |
| 43 | H-dSer-H-G-T-F-T-S-D-L-S-K-L-L-D-E-Q-L-A-K-D-F-I-E-W-L-I-A-G-G-P-S-S-G-A-P-P-P-S-NH2 |
| 44 | H-S-H-G-T-F-T-S-D-L-S-K-L-L-D-E-Q-L-A-K-D-F-I-E-W-L-I-A-G-G-P-S-S-G-A-P-P-P-S-NH2 |
| 45 | H-Aib-H-G-T-F-T-S-D-L-S-K-Q-L-D-E-Q-L-A-R-D-F-I-E-W-L-I-Bal-G-G-P-S-S-G-A-P-P-P-S-NH2 |
| 46 | H-Aib-H-G-T-F-T-S-D-L-S-K-Q-L-D-E-Q-L-A-R-D-F-I-E-W-L-I-Bal-G-G-P-P-S-G-A-P-P-P-S-NH2 |
| 47 | H-Aib-H-G-T-F-T-S-D-L-S-K-Q-L-D-E-Q-L-A-R-D-F-I-E-W-L-I-Bal-G-G-P-P-S-G-P-P-P-P-P-P-NH2 |
| 48 | H-Aib-H-G-T-F-T-S-D-L-S-K-Q-L-D-E-Q-L-A-R-D-F-I-E-W-L-I-Bal-dAla-G-P-P-S-dAla-P-P-P-P-P-P-NH2 |
| 49 | H-Aib-H-G-T-F-T-S-D-L-S-K-Q-L-D-E-Q-L-A-R-D-F-I-E-W-L-I-Bal-G-G-P-H-S-G-A-P-P-P-S-NH2 |
| 50 | H-Aib-H-G-T-F-T-S-D-L-S-K-Q-L-D-E-Q-L-A-R-D-F-I-E-W-L-I-Bal-P-G-P-S-S-G-A-P-P-P-S-NH2 |
| 51 | H-Aib-H-G-T-F-T-S-D-L-S-K-Q-L-D-E-Q-L-A-R-D-F-I-E-W-L-I-Bal-P-G-P-P-S-G-A-P-P-P-S-NH2 |
| 52 | H-Aib-H-G-T-F-T-S-D-L-S-K-Q-L-D-E-Q-L-A-R-D-F-I-E-W-L-I-Bal-P-G-P-H-S-G-A-P-P-P-S-NH2 |
| 53 | H-Aib-H-G-T-F-T-S-D-L-S-K-Q-L-D-E-Q-L-A-R-D-F-I-E-W-L-I-Bal-G-G-P-P-S-G-K-P-P-P-S-NH2 |
| 54 | H-Aib-H-G-T-F-T-S-D-L-S-K-Q-L-D-E-Q-L-A-R-D-F-I-E-W-L-I-Bal-G-G-H-P-S-G-A-P-P-P-S-NH2 |
| 55 | H-Aib-H-G-T-F-T-S-D-L-S-K-Q-L-D-E-Q-L-A-R-D-F-I-E-W-L-I-Bal-G-G-W-P-S-G-A-P-P-P-S-NH2 |
| 56 | H-Aib-H-G-T-F-T-S-D-L-S-K-Q-L-D-E-Q-L-A-R-D-F-I-E-W-L-I-Bal-G-G-H-P-S-G-K-P-P-P-S-NH2 |
| 57 | H-Aib-H-G-T-F-T-S-D-L-S-K-Q-L-E-E-Q-L-A-R-D-F-I-E-W-L-I-Bal-G-G-P-P-S-G-A-P-P-P-S-NH2 |
| 58 | H-Aib-H-G-T-F-T-S-D-L-S-K-Q-L-D-E-Q-L-A-R-D-F-I-E-W-L-I-Bal-G-G-P-R-S-G-A-P-P-P-S-NH2 |
| 59 | H-Aib-H-G-T-F-T-S-D-L-S-K-Q-L-D-E-Q-L-A-R-D-F-I-E-W-L-I-Bal-dAla-G-P-P-S-dAla-A-P-P-P-S-NH2 |
| 60 | H-Aib-Q-G-T-F-T-S-D-L-S-K-L-L-E-E-Q-R-A-R-E-F-I-E-W-L-I-Bal-dAla-G-P-P-S-dAla-A-P-P-P-S-NH2 |

Another embodiment is the peptide of Seq. ID No. 60 and its use as pharmaceutical.

In case the GLP-1/Glucagon agonist prodrugs comprising the compounds according to formula (I) contain one or more acidic or basic groups, the invention also comprises their corresponding pharmaceutically or toxicologically acceptable salts, in particular their pharmaceutically utilizable salts. Thus, the GLP-1/Glucagon agonist prodrugs comprising the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. GLP-1/Glucagon agonist prodrugs comprising the compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the GLP-1/Glucagon agonist prodrugs comprising the compounds of the formula (I) simultaneously contain acidic and basic groups in the molecule, the invention also includes, in addition to the salt forms mentioned, inner salts or betaines (zwitterions). The respective salts according to GLP-1/Glucagon agonist prodrugs comprising the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the GLP-1/Glucagon agonist prodrugs comprising the compounds of the formula (I) which, owing to low physiological compatibility, are not directly suitable for use in pharmaceuticals but which can be used, for example, as intermediates for chemical reactions or for the preparation of pharmaceutically acceptable salts.

Process of Making

The peptides Y may be prepared by convenient methods known in the art.

The linkers L are prepared by methods as described in the examples and as disclosed in WO2009/095479, WO2011/012718 and WO2012/035139.

The hydrogel-linked GLP-1/Glucagon agonist prodrug of the present invention can be prepared by synthesizing the building blocks activated hyaluronic acid hydrogel Z-L$^{1*}$ and activated peptide linker conjugate L$^{2*}$-L-Y.

Activated groups L$^{1*}$ and L$^{2*}$ are used to conjugate peptide to the polymers.

Scheme 1 shows different types of linking chemistries which can be used to conjugate the peptide with self-immolative linkers to the polymer. Thus, besides thiol-maleimide chemistry, other biorthogonal chemistries can be used. In scheme 1 the dashed lines indicates the positions where L$^1$ and L$^2$ are attached.

After loading the GLP-1/Glucagon agonist-linker conjugate to the functionalized hyaluronic acid hydrogel, all remaining functional groups are optionally capped with a suitable blocking reagent to prevent undesired side-reactions.

In the case of a functionalized maleimido group-containing HA-hydrogel, a thiol containing compound such as mercaptoethanol is a suitable blocking agent.

Scheme 1

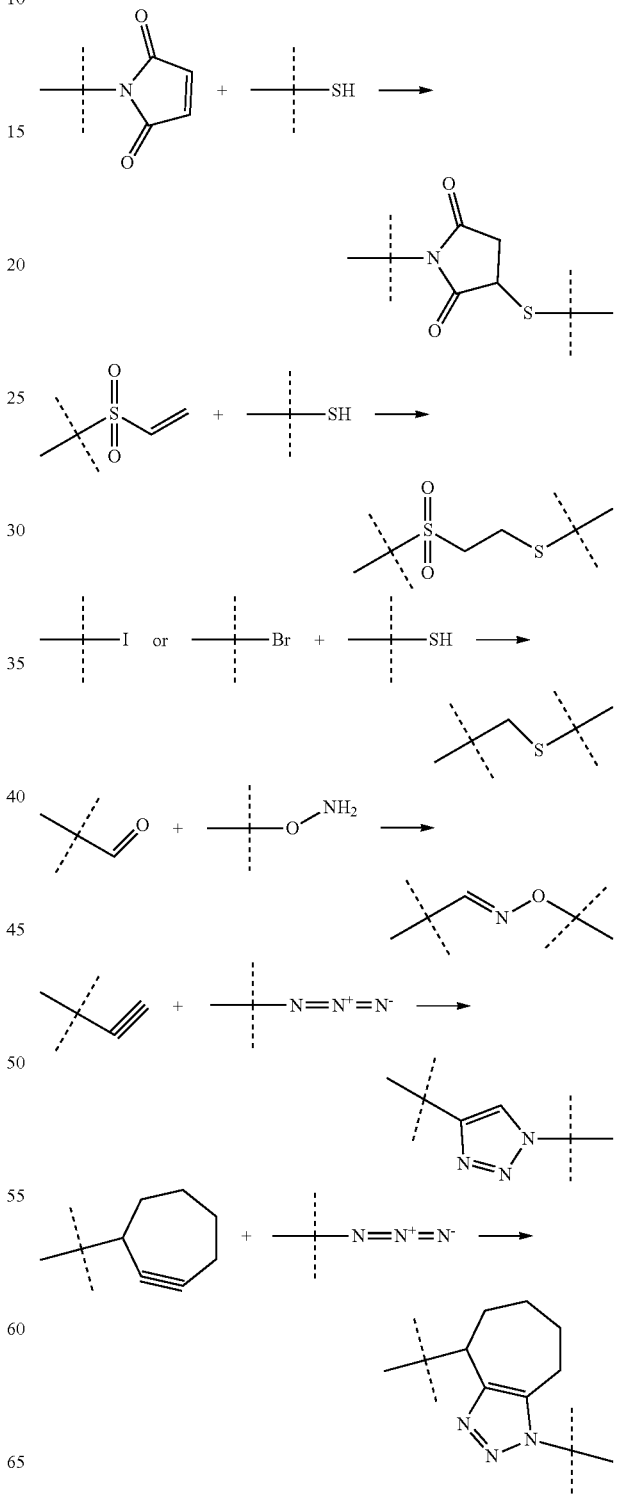

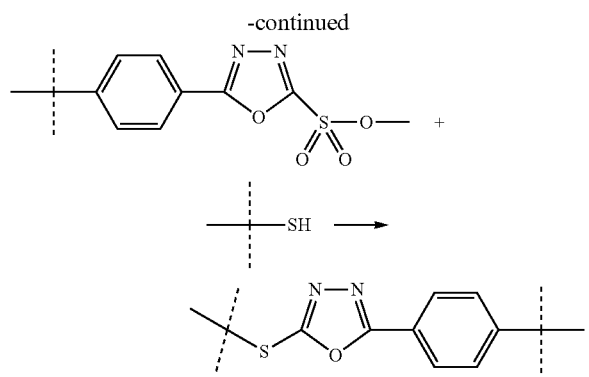

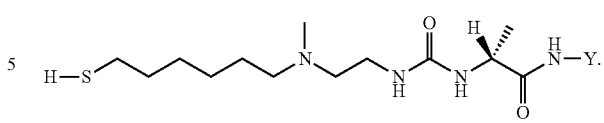

Another aspect of the present invention are functionalized intermediates comprising a GLP-1/Glucagon agonist-linker conjugate $L^{2*}$-L-Y.

One embodiment of a GLP-1/Glucagon agonist-linker conjugate $L^{2*}$-L-Y comprises a thiol functionalization, resulting in the formula

HS-$L^2$-L-Y wherein $L^2$, L and Y have the meanings as described above.

One embodiment of thiol functionalized a GLP-1/Glucagon agonist-linker conjugate $L^{2*}$-L-Y is a GLP-1/Glucagon agonist-linker conjugate of formula (VIII)

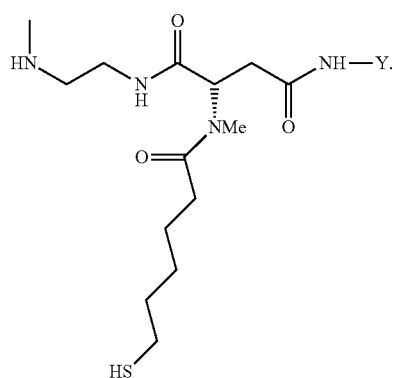

One embodiment of thiol functionalized GLP-1/Glucagon agonist-linker conjugate $L^{2*}$-L-Y is a GLP-1/Glucagon agonist-linker conjugate of formula (IX)

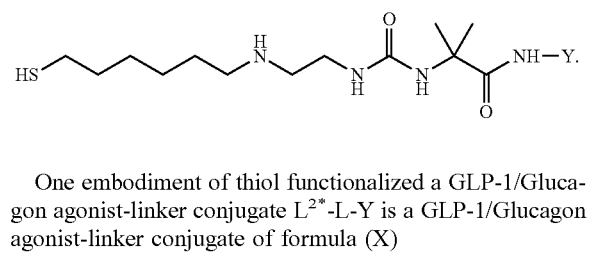

One embodiment of thiol functionalized a GLP-1/Glucagon agonist-linker conjugate $L^{2*}$-L-Y is a GLP-1/Glucagon agonist-linker conjugate of formula (X)

Pharmaceutical Composition

Another aspect of the present invention is a pharmaceutical composition comprising a prodrug of the present invention or a pharmaceutically acceptable salt thereof together with a pharmaceutically acceptable excipient. The pharmaceutical composition is further described in the following paragraphs.

The composition of GLP-1/Glucagon agonist-hydrogel prodrug may be provided as a suspension composition or as a dry composition. In one embodiment the pharmaceutical composition of GLP-1/Glucagon agonist-hydrogel prodrug is a dry composition. Suitable methods of drying are, for example, spray-drying and lyophilization (freeze-drying). Preferably, the pharmaceutical composition of GLP-1/Glucagon agonist-hydrogel prodrug is dried by lyophilization.

In another embodiment the pharmaceutical composition of GLP-1/Glucagon agonist-hydrogel prodrug is a ready to use suspension.

In another embodiment the pharmaceutical composition of GLP-1/Glucagon agonist-hydrogel prodrug is a ready to use suspension wherein the prodrug is swollen in water/buffer to a concentration of 0.5 to 8% (w/v).

In another embodiment the pharmaceutical composition of GLP-1/Glucagon agonist-hydrogel prodrug is a ready to use suspension wherein the prodrug is swollen in water/buffer to a concentration of 1 to 4% (w/v).

In another embodiment the pharmaceutical composition of GLP-1/Glucagon agonist-hydrogel prodrug is a ready to use suspension wherein the prodrug is swollen in water/buffer to a concentration of 1.5 to 3% (w/v).

Preferably, the GLP-1/Glucagon agonist hydrogel prodrug is sufficiently dosed in the composition to provide therapeutically effective amount of GLP-1/Glucagon agonist for at least three days in one application. More preferably, one application of the GLP-1/Glucagon agonist hydrogel prodrug is sufficient for one week.

The pharmaceutical composition of GLP-1/Glucagon agonist-hydrogel prodrug according to the present invention contains one or more excipients.

Excipients used in parenteral compositions may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The compositions of GLP-1/Glucagon agonist-hydrogel prodrugs according to the present invention contain one or more than one excipient, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability (ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum (iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride (iv) Stabilizers: Stabilisation is achieved by strengthening of the protein-stabilising forces, by destabilisation of the denatured stater, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used (v) Anti-adsorption agents: Mainly ionic or inon-ionic surfactants or other proteins or soluble polymers are used to coat or adsorb competitively to the inner surface of the composition's or composition's container. E.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value (vi) Lyo- and/or cryoprotectants: During freeze- or spray drying, excipients may counteract the destabilising effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, methionine, glutathione, monothioglycerol, morin, polyethylenimine (PEI), propyl gallate, vitamin E, chelating agents such as citric acid, EDTA, hexaphosphate, thioglycolic acid (viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Spreading or diffusing agent: modifies the permeability of connective tissue through the hydrolysis of components of the extracellular matrix in the interstitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture In one embodiment the composition of GLP-1/Glucagon agonist-hydrogel prodrug contains one or more than one viscosifier and/or viscosity modifying agent.

In another embodiment the composition of GLP-1/Glucagon agonist-hydrogel prodrug contains hyaluronic acid as viscosifier and/or viscosity modifying agent.

In another embodiment the composition of GLP-1/Glucagon agonist-hydrogel prodrug comprises hyaluronic acid as viscosifier and/or viscosity modifying agent in a concentration of 5 to 30 wt %.

In another embodiment the composition of GLP-1/Glucagon agonist-hydrogel prodrug comprises hyaluronic acid as viscosifier and/or viscosity modifying agent of a molecular weight of 200 kDa to 6 million kDa.

In another embodiment the composition of GLP-1/Glucagon agonist-hydrogel prodrug comprises hyaluronic acid as viscosifier and/or viscosity modifying agent of a molecular weight of 500 kDa to 3 million kDa.

The term "excipient" preferably refers to a diluent, adjuvant, or vehicle with which the therapeutic is administered. Such pharmaceutical excipient can be sterile liquids. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. Such compositions will contain a therapeutically effective amount of the therapeutic, preferably in purified form, together with a suitable amount of excipient so as to provide the form for proper administration to the patient. The formulation should suit the mode of administration.

In a general embodiment a pharmaceutical composition of the present invention whether in dry form or as a suspension or in another form may be provided as single or multiple dose composition.

In one embodiment of the present invention, the dry composition of GLP-1/Glucagon agonist-hydrogel prodrug is provided as a single dose, meaning that the container in which it is supplied contains one pharmaceutical dose.

Thus, in another aspect of the present invention the composition is provided as a single dose composition.

In another aspect of the present invention the composition is comprised in a container. In one embodiment the container is a dual-chamber syringe. Especially the dry composition according to the present invention is provided in a first chamber of the dual-chamber syringe and reconstitution solution is provided in a second chamber of the dual-chamber syringe.

Prior to applying the dry composition of GLP-1/Glucagon agonist-hydrogel prodrug to a patient in need thereof, the dry composition is reconstituted. Reconstitution can take place in the container in which the dry composition of GLP-1/Glucagon agonist-hydrogel prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials. If the GLP-1/Glucagon agonist-hydrogel prodrug composition is provided as single dose, the reconstituion solution may contain one or more preservative and/or antimicrobial. Preferably, the reconstitution solution is sterile water.

An additional aspect of the present invention relates to the method of administration of a reconstituted GLP-1/Glucagon agonist hydrogel prodrug composition. The GLP-1/Glucagon agonist hydrogel prodrug composition can be administered by methods of injection or infusion, including intradermal, subcutaneous, intramuscular, intravenous, intraosseous, and intraperitoneal.

A further aspect is a method of preparing a reconstituted composition comprising a therapeutically effective amount of an GLP-1/Glucagon agonist hydrogel prodrug, and optionally one or more pharmaceutically acceptable excipients, wherein the GLP-1/Glucagon agonist is transiently linked to a hydrogel, the method comprising the step of
  contacting the composition of the present invention with a reconstitution solution.

Another aspect is a reconstituted composition comprising a therapeutically effective amount of a GLP-1/Glucagon agonist hydrogel prodrug, and optionally one or more pharmaceutically acceptable excipients, wherein the GLP-1/Glucagon agonist is transiently linked to a hydrogel obtainable by the method above.

Another aspect of the present invention is the method of manufacturing a dry composition of GLP-1/Glucagon agonist-hydrogel prodrug. In one embodiment, such suspension composition is made by
  (i) admixing the GLP-1/Glucagon agonist-hydrogel prodrug with one or more excipients,
  (ii) transferring amounts equivalent to single or multiple doses into a suitable container,
  (iii) drying the composition in said container, and
  (iv) sealing the container.

Suitable containers are vials, syringes, dual-chamber syringes, ampoules, and cartridges.

Another aspect is a kit of parts. When the administration device is simply a hypodermic syringe then the kit may comprise the syringe, a needle and a container comprising the dry GLP-1/Glucagon agonist-hydrogel prodrug composition for use with the syringe and a second container comprising the reconstitution solution. In more preferred embodiments, the injection device is other than a simple hypodermic syringe and so the separate container with reconstituted GLP-1/Glucagon agonist-hydrogel prodrug is adapted to engage with the injection device such that in use the liquid composition in the container is in fluid connection with the outlet of the injection device. Examples of administration devices include but are not limited to hypodermic syringes and pen injector devices. Particularly preferred injection devices are the pen injectors in which case the container is a cartridge, preferably a disposable cartridge.

A preferred kit of parts comprises a needle and a container containing the composition according to the present invention and optionally further containing a reconstitution solution, the container being adapted for use with the needle. Preferably, the container is a dual-chamber syringe.

In another aspect, the invention provides a cartridge containing a composition of GLP-1/Glucagon agonist-hydrogel prodrug as hereinbefore described for use with a pen injector device. The cartridge may contain a single dose or multiplicity of doses of GLP-1/Glucagon agonist.

In one embodiment of the present invention the suspension composition of GLP-1/Glucagon agonist-hydrogel prodrug does not only comprise an GLP-1/Glucagon agonist-hydrogel prodrug and one or more than one excipients, but also other biologically active agents, either in their free form or as prodrugs. Preferably, such additional one or more biologically active agent is a prodrug, more preferably a hydrogel prodrug. Such biologically active agents include, but are not limited to, compounds of the following classes:

Injectability

Preferably, the formulation can be administered by injection through a needle smaller than 0.26 mm inner diameter (26 Gauge), even more preferably through a needle smaller than 0.18 mm inner diameter (28 Gauge), and most preferably through a needle small than 0.16 mm inner diameter (30 Gauge).

It is understood that the terms "can be administered by injection", "injectable" or "injectability" refer to a combination of factors such as a certain force applied to a plunger of a syringe containing the biodegradable HA hydrogel according to the invention swollen in a liquid at a certain concentration (w/v) and at a certain temperature, a needle of a given inner diameter connected to the outlet of such syringe, and the time required to extrude a certain volume of the biodegradable hydrogel according to the invention from the syringe through the needle.

In order to provide for injectability, a volume of 1 mL of the GLP-1/glucagon agonist prodrugs according to the invention swollen in water and contained in a syringe (holding a plunger of a diameter of 4.7 mm) can be extruded at room temperature within 10 seconds by applying a force of equal/less than 20 Newton through a needle of 26 gauge.

A preferred injectability is a volume of 1 mL of the GLP-1/glucagon agonist prodrugs according to the invention swollen in water and contained in a syringe (holding a plunger of a diameter of 4.7 mm) which can be extruded at room temperature within 10 seconds by applying a force of equal/less than 20 Newton through a needle of 30 gauge.

Suprisingly it was found that the HA carrier of the invention needs lesser force for injection the higher the peptide loading on the polymer is (FIG. 5).

In order to provide for injectability, a volume of 1 mL of the GLP-1/glucagon agonist prodrugs according to the invention swollen in water/buffer to a concentration of at least 1.5% (w/v) and contained in a syringe holding a plunger of a diameter of 4.7 mm can be extruded at room temperature within 10 seconds by applying a force of less than 30 Newton through a needle of 30 gauge.

More preferably injectability is achieved for a GLP-1/glucagon agonist prodrug according to the invention swollen in water/buffer to a concentration of at least 2% (w/v) by applying a force of less than 30 Newton through a needle of 30 gauge.

Most preferably injectability is achieved for a GLP-1/glucagon agonist prodrug according to the invention swollen in water/buffer to a concentration of at least 2% (w/v) by applying a force of less than 20 Newton through a needle of 30 gauge.

An important characteristic of the prodrug is the forming of a stable depot which stays its application site. The degradation of the polymer should start after release of the drug.

Combination Therapy

The prodrugs of the present invention, dual agonists for the GLP-1 and glucagon receptors, can be widely combined with other pharmacologically active compounds, such as all drugs mentioned in the Rote Liste 2015, e.g. with all weight-reducing agents or appetite suppressants mentioned in the Rote Liste 2015, chapter 1, all lipid-lowering agents mentioned in the Rote Liste 2015, chapter 58, all antihypertensives and nephroprotectives, mentioned in the Rote Liste 2015, or all diuretics mentioned in the Rote Liste 2015, chapter 36.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Most of the active ingredients mentioned hereinafter are disclosed in the USP Dictionary of USAN and International Drug Names, US Pharmacopeia, Rockville 2011.

Other active substances which are suitable for such combinations include in particular those which for example potentiate the therapeutic effect of one or more active substances with respect to one of the indications mentioned and/or which allow the dosage of one or more active substances to be reduced.

Therapeutic agents which are suitable for combinations include, for example, antidiabetic agents such as:

Insulin and Insulin derivatives, for example: Glargine/Lantus®, 270-330 U/mL of insulin glargine (EP 2387989 A), 300 U/mL of insulin glargine (EP 2387989 A), Glulisin/Apidra®, Detemir/Levemir®, Lispro/Humalog®/Liprolog®, Degludec/DegludecPlus, Aspart, basal insulin and analogues (e.g. LY-2605541, LY2963016, NN1436), PEGylated insulin Lispro, Humulin®, Linjeta, SuliXen®, NN1045, Insulin plus Symlin, PE0139, fast-acting and short-acting insulins (e.g. Linjeta, PH20, NN1218, HinsBet), (APC-002)hydrogel, oral, inhalable, transdermal and sublingual insulins (e.g. Exubera®, Nasulin®, Afrezza, Tregopil, TPM 02, Capsulin, Oral-Lyn®, Cobalamin® oral insulin, ORMD-0801, NN1953, NN1954, NN1956, VIAtab, Oshadi oral insulin). Additionally included are also those insulin derivatives which are bonded to albumin or another protein by a bifunctional linker.

GLP-1, GLP-1 analogues and GLP-1 receptor agonists, for example: Lixisenatide/AVE0010/ZP10/Lyxumia, Exenatide/Exendin-4/Byetta/Bydureon/ITCA 650/AC-2993, Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

DPP-4 inhibitors, for example: Alogliptin/Nesina, Trajenta/Linagliptin/BI-1356/Ondero/Trajenta/Tradjenta/Trayenta/Tradzenta, Saxagliptin/Onglyza, Sitagliptin/Januvia/Xelevia/Tesave/Janumet/Velmetia, Galvus/Vildagliptin, Anagliptin, Gemigliptin, Teneligliptin, Melogliptin, Trelagliptin, DA-1229, Omarigliptin/MK-3102, KM-223, Evogliptin, ARI-2243, PBL-1427, Pinoxacin.

SGLT2 inhibitors, for example: Invokana/Canaglifozin, Forxiga/Dapagliflozin, Remoglifozin, Sergliflozin, Empagliflozin, Ipragliflozin, Tofogliflozin, Luseogliflozin, LX-4211, Ertuglifozin/PF-04971729, RO-4998452, EGT-0001442, KGA-3235/DSP-3235, LIK066, SBM-TFC-039, Biguanides (e.g. Metformin, Buformin, Phenformin), Thiazolidinediones (e.g. Pioglitazone, Rivoglitazone, Rosiglitazone, Troglitazone), dual PPAR agonists (e.g. Aleglitazar, Muraglitazar, Tesaglitazar), Sulfonylureas (e.g. Tolbutamide, Glibenclamide, Glimepiride/Amaryl, Glipizide), Meglitinides (e.g. Nateglinide, Repaglinide, Mitiglinide), Alpha-glucosidase inhibitors (e.g. Acarbose, Miglitol, Voglibose), Amylin and Amylin analogues (e.g. Pramlintide, Symlin).

GPR119 agonists (e.g. GSK-263A, PSN-821, MBX-2982, APD-597, ZYG-19, DS-8500), GPR40 agonists (e.g. Fasiglifam/TAK-875, TUG-424, P-1736, JTT-851, GW9508).

Other suitable combination partners are: Cycloset, inhibitors of 11-beta-HSD (e.g. LY2523199, BMS770767, RG-4929, BMS816336, AZD-8329, HSD-016, BI-135585), activators of glucokinase (e.g. TTP-399, AMG-151, TAK-329, GKM-001), inhibitors of DGAT (e.g. LCQ-908), inhibitors of protein tyrosinephosphatase 1 (e.g. Trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha2-antagonists, CCR-2 antagonists, SGLT-1 inhibitors (e.g. LX-2761).

One or more lipid lowering agents are also suitable as combination partners, such as for example: HMG-CoAreductase inhibitors (e.g. Simvastatin, Atorvastatin), fibrates (e.g. Bezafibrate, Fenofibrate), nicotinic acid and the derivatives thereof (e.g. Niacin), PPAR-(alpha, gamma or alpha/gamma) agonists or modulators (e.g. Aleglitazar), PPAR-delta agonists, ACAT inhibitors (e.g. Avasimibe), cholesterol absorption inhibitors (e.g. Ezetimibe), Bile acid-binding substances (e.g. cholestyramine, colesevelam), ileal bile acid transport inhibitors, MTP inhibitors, or modulators of PCSK9.

HDL-raising compounds such as: CETP inhibitors (e.g. Torcetrapib, Anacetrapid, Dalcetrapid, Evacetrapid, JTT-302, DRL-17822, TA-8995) or ABC1 regulators.

Other suitable combination partners are one or more active substances for the treatment of obesity, such as for example: Sibutramine, Tesofensine, Orlistat, antagonists of the cannabinoid-1 receptor, MCH-1 receptor antagonists, MC4 receptor agonists, NPY5 or NPY2 antagonists (e.g. Velneperit), beta-3-agonists, leptin or leptin mimetics, agonists of the 5HT2c receptor (e.g. Lorcaserin), or the combinations of bupropione/naltrexone, bupropione/zonisamide, bupropione/phentermine or pramlintide/metreleptin.

Other Suitable Combination Partners are:

Further gastrointestinal peptides such as Peptide YY 3-36 (PYY3-36) or analogues thereof, pancreatic polypeptide (PP) or analogues thereof.

Glucagon receptor agonists or antagonists, GIP receptor agonists or antagonists, ghrelin antagonists or inverse agonists, Xenin and analogues thereof.

Moreover, combinations with drugs for influencing high blood pressure, chronic heart failure or atherosclerosis, such as e.g.: Angiotensin II receptor antagonists (e.g. telmisartan, candesartan, valsartan, losartan, eprosartan, irbesartan, olmesartan, tasosartan, azilsartan), ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

Use

In another aspect, this invention relates to the use of a prodrug according to the invention or a physiologically acceptable salt thereof combined with at least one of the active substances described above as a combination partner, for preparing a medicament which is suitable for the treatment or prevention of diseases or conditions which can be affected by binding to the receptors for GLP-1 and glucagon and by modulating their activity.

Said compositions are for use in a method of treating or preventing diseases or disorders known for GLP-1/Glucagon agonist and GLP-1/Glucagon agonist agonists, for example, for treatment and prevention of hyperglycemia and for treatment and prevention of diabetes mellitus of any type, e.g. insulin-dependent diabetes mellitus, non insulin dependent diabetes mellitus, prediabetes or gestational diabetes mellitus, for prevention and treatment of metabolic syndrome and/or obesity and/or eating disorders, insulin resistance syndrome, lowering plasma lipid level, reducing the cardiac risk, reducing the appetite, reducing the body weight, etc.

The compounds of the invention are useful in the treatment or prevention of hepatosteatosis, preferably non-alcoholic liver-disease (NAFLD) and non-alcoholic steatohepatitis (NASH).

The use of the prodrugs according to the invention, or a physiologically acceptable salt thereof, in combination with one or more active substances may take place simultaneously, separately or sequentially.

The use of the prodrug according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises a prodrug according to the invention or a physiologically acceptable salt of such a compound and at least one of the active substances described above as combination partners, optionally together with one or more inert carriers and/or diluents.

The compound according to the invention, or physiologically acceptable salt or solvate thereof, and the additional active substance to be combined therewith may both be present together in one formulation, for example a suspension, or separately in two identical or different formulations, for example as so-called kit-of-parts.

Yet another aspect of the present invention is a method of treating, controlling, delaying or preventing in a mammalian patient, preferably in a human, in need of the treatment of one or more conditions comprising administering to said patient a therapeutically effective amount of a prodrug of the present invention or a pharmaceutical composition of the present invention or a pharmaceutically acceptable salt thereof.

EXAMPLES

Materials and Methods
Abbreviations employed are as follows:
AA amino acid
AcOH acetic acid
AcOEt ethyl acetate
cAMP cyclic adenosine monophosphate
Bn benzyl
Boc tert-butyloxycarbonyl
BOP (benzotriazol-1-yloxy)tris(dimethylamino)phosphonium hexafluorophosphate
BSA bovine serum albumin
tBu tertiary butyl
DBU 1,3-diazabicyclo[5.4.0]undecene
DCC N,N-dicyclohexylcarbodiimid
DCM dichloromethane
Dde 1-(4,4-dimethyl-2,6-dioxocyclohexylidene)-ethyl
ivDde 1-(4,4-dimethyl-2,6-dioxocyclohexylidene)3-methyl-butyl
DIC N,N'-diisopropylcarbodiimide
DIPEA N,N-diisopropylethylamine
DMAP dimethylamino-pyridine
DMEM Dulbecco's modified Eagle's medium
DMF dimethyl formamide
DMSO dimethylsulfoxide
DTT DL dithiotreitol
EDC 1-Ethyl-3-(3-dimethylaminopropyl)carbodiimid
EDT ethanedithiol
EDTA ethylenediaminetetraacetic acid
eq stoichiometric equivalent
EtOH ethanol
FBS fetal bovine serum
Fmoc fluorenylmethyloxycarbonyl HATU O-(7-azabenzotriazol-1-yl)-N,N,N',N'-tetramethyl-uronium hexafluorophosphate
HBSS Hanks' Balanced Salt Solution
HBTU 2-(1H-benzotriazol-1-yl)-1,1,3,3-tetramethyl-uronium hexafluorophosphate
HEPES 2-[4-(2-hydroxyethyl)piperazin-1-yl]ethanesulfonic acid
HOBt 1-hydroxybenzotriazole
HOSu N-hydroxysuccinimide
s HPLC High Performance Liquid Chromatography
HTRF Homogenous Time Resolved Fluorescence
IBMX 3-isobutyl-1-methylxanthine
LC/MS Liquid Chromatography/Mass Spectrometry
Mal 3-maleimido propyl
Mal-PEG6-NHS N-(3-maleimidopropyl)-21-amino-4,7,10,13,16,19-hexaoxa-heneicosanoic acid NHS ester
Me methyl
MeOH methanol
Mmt 4-methoxytrityl
MS mass spectrum/mass spectrometry
MTBE methyl tert.-butyl ether
MW molecular mass
NHS N-hydroxy succinimide
Palm palmitoyl
iPrOH 2-propanol
PBS phosphate buffered saline
PEG polyethylene glycole
PK pharmacokinetic
PyBOP benzotriazole-1-yl-oxy-tris-pyrrolidino-phosphonium hexafluorophosphate
Phth phthalimido
RP-HPLC reversed-phase high performance liquid chromatography
rpm rounds per minute
RT room temperature
SEC size exclusion chromatography
TCEP tris(2-carboxyethyl)phosphine hydrochloride
TES triethylsilane
TFA trifluoroacetic acid
s THF tetrahydrofurane
TMEDA N,N,N'N'-tetramethylethylene diamine
Tris tris(hydroxymethyl)aminomethane
Trt trityl
UPLC Ultra Performance Liquid Chromatography
UV ultraviolet
V volume

Example 1

General Synthesis of Peptidic Compounds
Materials:
Different Rink-Amide resins (4-(2',4'-Dimethoxyphenyl-Fmoc-aminomethyl)-phenoxyacetamido-norleucylaminomethyl resin, Merck Biosciences; 4-[(2,4-Dimethoxyphenyl)(Fmoc-amino)methyl]phenoxy acetamido methyl resin, Agilent Technologies) were used for the synthesis of peptide amides with loadings in the range of 0.3-0.4 mmol/g.

Fmoc protected natural amino acids were purchased from Protein Technologies Inc., Senn Chemicals, Merck Biosciences, Novabiochem, Iris Biotech, Nagase or Bachem. The following standard amino acids were used throughout the syntheses: Fmoc-L-Ala-OH, Fmoc-L-Arg(Pbf)-OH, Fmoc-L-Asn(Trt)-OH, Fmoc-L-Asp(OtBu)-OH, Fmoc-L-Cys(Trt)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH.

In addition, the following special amino acids were purchased from the same suppliers as above: Fmoc-L-Lys(ivDde)-OH, Fmoc-Aib-OH, Fmoc-D-Ser(tBu)-OH, Fmoc-D-Ala-OH, Boc-L-His(Boc)-OH (available as toluene solvate) and Boc-L-His(Trt)-OH, Fmoc-L-Nle-OH, Fmoc-L-Met(O)—OH, Fmoc-L-Met(O2)-OH, Fmoc-(S)MeLys(Boc)-OH, Fmoc-(R)MeLys(Boc)-OH, Fmoc-(S)MeOrn(Boc)-OH and Boc-L-Tyr(tBu)-OH.

The solid phase peptide syntheses were performed for example on a Prelude Peptide Synthesizer (Protein Technologies Inc) or similar automated synthesizer using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF 2× for 20 min. Washes: 5×DMF.

All the peptides that had been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analyzed by analytical HPLC and checked by ESI mass spectrometry. Crude peptides were purified by a conventional preparative HPLC purification procedure.

Analytical HPLC/UPLC
Method A: detection at 215 nm
column: Aeris Peptide, 3.6 μm, XB-C18 (250×4.6 mm) at 60° C.
solvent: $H_2O+0.1\%$ TFA: ACN+0.1% TFA (flow 1.5 ml/min)
gradient: 90:10 (0 min) to 90:10 (3 min) to 10:90 (43 min) to 10:90 (48 min) to 90:10 (49 min) to 90:10 (50 min)
Method B: detection at 220 nm
column: Zorbax, 5 μm, C18 (250×4.6 mm) at 25° C.
solvent: $H_2O+0.1\%$ TFA: 90% ACN+10% $H_2O+0.1\%$ TFA (flow 1.0 ml/min)
gradient: 100:0 (0 min) to 98:2 (2 min) to 30:70 (15 min) to 5:95 (20 min) to 0:100 (25 min) to 0:100 (30 min) to 98:2 (32 min) to 98:2 (35 min)
Method C1: detection at 210-225 nm, optionally coupled to a mass analyser Waters LCT Premier, electrospray positive ion mode
column: Waters ACQUITY UPLC® BEH™ C18 1.7 μm (150×2.1 mm) at 50° C.
solvent: $H_2O+1\%$ FA: ACN+1% FA (flow 0.5 ml/min)
gradient: 95:5 (0 min) to 95:5 (1.80 min) to 80:20 (1.85 min) to 80:20 (3 min) to 60:40 (23 min) to 25:75 (23.1 min) to 25:75 (25 min) to 95:5 (25.1 min) to 95:5 (30 min)
Method C2: detection at 210-225 nm, optionally coupled to a mass analyser Waters LCT Premier, electrospray positive ion mode
column: Waters ACQUITY UPLC® BEH™ C18 1.7 μm (150×2.1 mm) at 50° C.
solvent: $H_2O+1\%$ FA: ACN+1% FA (flow 0.6 ml/min)
gradient: 95:5 (0 min) to 95:5 (1 min) to 65:35 (2 min) to 65:35 (3 min) to 45:55 (23 min) to 25:75 (23.1 min) to 25:75 (25 min) to 95:5 (25.1 min) to 95:5 (30 min)
Method C3: detection at 210-225 nm, optionally coupled to a mass analyser Waters LCT Premier, electrospray positive ion mode
column: Waters ACQUITY UPLC® BEH™ C18 1.7 μm (150×2.1 mm) at 50° C.
solvent: $H_2O+1\%$ FA: ACN+1% FA (flow 1 ml/min)

gradient: 95:5 (0 min) to 95:5 (1 min) to 65:35 (2 min) to 65:35 (3 min) to 45:55 (20 min) to 2:98 (20.1 min) to 2:98 (25 min) to 95:5 (25.1 min) to 95:5 (30 min)

Method C4:
detection at 210-225 nm, optionally coupled to a mass analyser Waters LCT Premier, electrospray positive ion mode
column: Waters ACQUITY UPLC® BEH™ C18 1.7 μm (150×2.1 mm) at 50° C.
solvent: $H_2O$+1% FA: ACN+1% FA (flow 1 ml/min)
gradient: 95:5 (0 min) to 95:5 (1.80 min) to 80:20 (1.85 min) to 80:20 (3 min) to 60:40 (23 min) to 2:98 (23.1 min) to 2:98 (25 min) to 95:5 (25.1 min) to 95:5 (30 min)

Method D: detection at 214 nm
column: Waters X-Bridge C18 3.5 μm 2.1×150 mm
solvent: $H_2O$+0.5% TFA: ACN (flow 0.55 ml/min)
gradient: 90:10 (0 min) to 40:60 (5 min) to 1:99 (15 min)

Method E: detection at 210-225 nm, optionally coupled to a mass analyser Waters LCT Premier, electrospray positive ion mode
column: Waters ACQUITY UPLC® BEH™ C18 1.7 μm (150×2.1 mm) at 50° C.
solvent: $H_2O$+1% FA: ACN+1% FA (flow 0.9 ml/min)
gradient: 95:5 (0 min) to 95:5 (2 min) to 35:65 (3 min) to 65:35 (23.5 min) to 5:95 (24 min) to 95:5 (26 min) to 95:5 (30 min)

General Preparative HPLC Purification Procedure:

The crude peptides were purified either on an Äkta Purifier System or on a Jasco semiprep HPLC System. Preparative RP-C18-HPLC columns of different sizes and with different flow rates were used depending on the amount of crude peptide to be purified. Acetonitrile+0.05 to 0.1% TFA (B) and water+0.05 to 0.1% TFA (A) were employed as eluents. Alternatively, a buffer system consisting of acetonitrile and water with minor amounts of acetic acid was used. Product-containing fractions were collected and lyophilized to obtain the purified product, typically as TFA or acetate salt.

Solubility and Stability-Testing of Exendin-4 Derivatives

Prior to the testing of solubility and stability of a peptide batch, its content was determined. Therefore, two parameters were investigated, its purity (HPLC-UV) and the amount of salt load of the batch (ion chromatography).

Example 2

For solubility testing, the target concentration was 1.0 mg/mL pure compound. Therefore, solutions from solid samples were prepared in different buffer systems with a concentration of 1.0 mg/mL compound based on the previously determined content. HPLC-UV was performed after 2 h of gentle agitation from the supernatant, which was obtained by 20 min of centrifugation at 4000 rpm.

The solubility was then determined by comparison with the UV peak areas obtained with a stock solution of the peptide at a concentration of 2 mg/mL in pure water or a variable amount of acetonitrile (optical control that all of the compound was dissolved). This analysis also served as starting point (t0) for the stability testing.

Example 3

For stability testing, an aliquot of the supernatant obtained for solubility was stored for 7 days at 25° C. or 40° C. After that time course, the sample was centrifuged for 20 min at 4000 rpm and the supernatant was analysed with HPLC-UV.

For determination of the amount of the remaining peptide, the peak areas of the target compound at t0 and t7 were compared, resulting in "% remaining peptide", following the equation % remaining peptide=[(peak area peptide $t7$)×100]/peak area peptide $t0$.

The amount of soluble degradation products was calculated from the comparison of the sum of the peak areas from all observed impurities reduced by the sum of peak areas observed at t0 (i.e. to determine the amount of newly formed peptide-related species). This value was given in percentual relation to the initial amount of peptide at t0, following the equation:

% soluble degradation products={[(peak area sum of impurities $t7$)−(peak area sum of impurities $t0$)]×100}/peak area peptide $t0$ The potential difference from the sum of "% remaining peptide" and "% soluble degradation products" to 100% reflects the amount of peptide which did not remain soluble upon stress conditions following the equation % precipitate=100−([% remaining peptide]+[% soluble degradation products])

This precipitate includes non-soluble degradation products, polymers and/or fibrils, which have been removed from analysis by centrifugation.

The chemical stability is expressed as "% remaining peptide".

Anion Chromatography

Instrument: Dionex ICS-2000, pre/column: Ion Pac AG-18 2×50 mm (Dionex)/AS18 2×250 mm (Dionex), eluent: aqueous sodium hydroxide, flow: 0.38 mL/min, gradient: 0-6 min: 22 mM KOH, 6-12 min: 22-28 mM KOH, 12-15 min: 28-50 mM KOH, 15-20 min: 22 mM KOH, suppressor: ASRS 300 2 mm, detection: conductivity.

As HPLC/UPLC method, method D or E has been used.

Example 4: In Vitro Data on GLP-1 and Glucagon Receptor

Potencies of peptidic compounds at the GLP-1 and glucagon receptors were determined by exposing cells expressing human glucagon receptor (hGlucagon R) or human GLP-1 receptor (hGLP-1 R) to the listed compounds at increasing concentrations and measuring the formed cAMP as described in example 27.

The results are shown in Table 2:

TABLE 2

| EC50 values of exendin-4 derivatives at GLP-1 and Glucagon receptors (indicated in pM) | | | | | |
|---|---|---|---|---|---|
| SEQ ID NO | EC50 hGLP-1R | EC50 hGlucagon-R | SEQ ID NO | EC50 hGLP-1R | EC50 hGlucagon-R |
| 4 | 1.7 | 6.2 | 24 | 1.2 | 11.1 |
| 5 | 2.7 | 5.0 | 25 | 4.6 | 259.0 |
| 6 | 4.9 | 24.3 | 26 | 0.9 | 33.8 |
| 7 | 8.5 | 20.6 | 27 | 1.0 | 44.8 |
| 8 | 1.2 | 5.3 | 28 | 1.1 | 57.7 |
| 9 | 1.5 | 35.6 | 29 | 0.4 | 21.3 |
| 10 | 1.6 | 47.5 | 30 | 0.5 | 10.9 |
| 11 | 0.9 | 68.0 | 31 | 0.6 | 24.6 |
| 12 | 1.0 | 35.6 | 32 | 1.2 | 29.8 |
| 13 | 1.4 | 44.9 | 33 | 2.5 | 94.1 |
| 14 | 1.6 | 77.5 | 34 | 1.1 | 41.5 |
| 15 | 1.0 | 18.3 | 35 | 1.0 | 555.0 |
| 16 | 3.7 | 8.2 | 36 | 1.0 | 581.0 |

TABLE 2-continued

EC50 values of exendin-4 derivatives at GLP-1 and Glucagon receptors (indicated in pM)

| SEQ ID NO | EC50 hGLP-1R | EC50 hGlucagon-R | SEQ ID NO | EC50 hGLP-1R | EC50 hGlucagon-R |
|---|---|---|---|---|---|
| 17 | 6.0 | 10.1 | 37 | 1.4 | 58.1 |
| 18 | 2.6 | 7.9 | 38 | 0.8 | 11.5 |
| 19 | 1.7 | 4.7 | 39 | 1.0 | 401.0 |
| 20 | 0.8 | 26.7 | 40 | 3.5 | 12.1 |
| 21 | 1.9 | 8.9 | 41 | 2.2 | 25.7 |
| 22 | 4.4 | 26.1 | 43 | 2.0 | 53.9 |
| 23 | 1.2 | 3.9 | 44 | 1.8 | 20.0 |
| 45 | 2.1 | 7.9 | 46 | 2.4 | 8.0 |
| 47 | 5.3 | 13.4 | 48 | 2.1 | 10.0 |
| 49 | 1.8 | 6.5 | 50 | 1.8 | 4.2 |
| 51 | 2.3 | 3.7 | 52 | 2.1 | 4.2 |
| 53 | 2.4 | 10.5 | 54 | 1.4 | 7.7 |
| 55 | 2.4 | 10.5 | 56 | 1.9 | 9.4 |
| 57 | 1.4 | 4.7 | 58 | 1.4 | 11.5 |
| 59 | n.a. | n.a. | 60 | 1.8 | 6.5 |

Linker Synthesis

Example 5

Synthesis of Linker Reagent 5c

Linker reagent 5c was synthesized according to the following scheme:

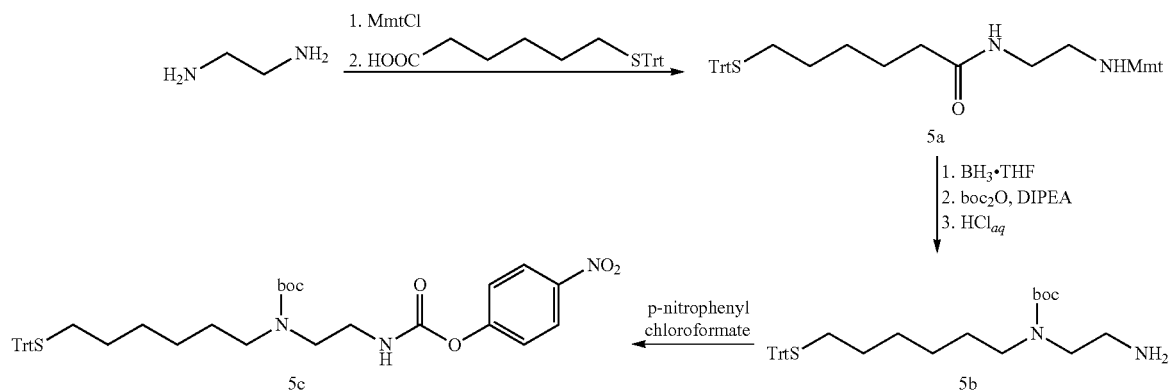

Synthesis of Linker Reagent Intermediate 5a m-Methoxytrityl chloride (3 g, 9.71 mmol) was dissolved in DCM (20 mL) and added dropwise to a solution of ethylenediamine (6.5 mL, 97.1 mmol) in DCM (20 mL). After two hours the solution was poured into diethyl ether (300 mL) and washed three times with 30/1 (v/v) brine/0.1 M NaOH solution (50 ml each) and once with brine (50 mL). The organic phase was dried over $Na_2SO_4$ and volatiles were removed under reduced pressure. Mmt-protected intermediate (3.18 g, 9.56 mmol) was used in the next step without further purification.

The Mmt-protected intermediate (3.18 g, 9.56 mmol) was dissolved in anhydrous DCM (30 mL). 6-(S-Tritylmercapto)hexanoic acid (4.48 g, 11.47 mmol), PyBOP (5.67 g, 11.47 mmol) and DIPEA (5.0 mL, 28.68 mmol) were added and the mixture was agitated for 30 min at RT. The solution was diluted with diethyl ether (250 mL) and washed three times with 30/1 (v/v) brine/0.1 M NaOH solution (50 mL each) and once with brine (50 mL). The organic phase was dried over $Na_2SO_4$ and volatiles were removed under reduced pressure. 5a was purified by flash chromatography.

Yield: 5.69 g (8.09 mmol).

MS: m/z 705.4=[M+H]+(MW calculated=705.0).

Synthesis of Linker Reagent Intermediate 5b

To a solution of 5a (3.19 g, 4.53 mmol) in anhydrous THF (50 mL) was added $BH_3$.THF (1 M solution, 8.5 mL, 8.5 mmol) and the solution was stirred for 16 h at RT. Further $BH_3$.THF (1 M solution, 14 mL, 14 mmol) was added and stirred for 16 h at RT. The reaction was quenched by addition of methanol (8.5 mL). N,N-dimethyl-ethylenediamine (3 mL, 27.2 mmol) was added and the solution was heated to reflux and stirred for three h. Reaction mixture was allowed to cool down to RT and was then diluted with ethyl acetate (300 mL), washed with saturated, aqueous $Na_2CO_3$ solution (2×100 mL) and saturated, aqueous $NaHCO_3$ solution (2×100 mL). The organic phase was dried over $Na_2SO_4$ and volatiles were removed under reduced pressure to obtain crude amine intermediate (3.22 g).

The amine intermediate (3.22 g) was dissolved in DCM (5 mL). $Boc_2O$ (2.97 g, 13.69 mmol) dissolved in DCM (5 mL) and DIPEA (3.95 mL, 22.65 mmol) were added and the mixture was agitated at RT for 30 min. The mixture was purified by flash chromatography to obtain the crude Boc- and Mmt-protected intermediate (3.00 g).

MS: m/z 791.4=[M+H]+, 519.3=[M-Mmt+H]+ (MW calculated=791.1).

0.4 M aqueous HCl (48 mL) was added to a solution of the Boc- and Mmt-protected intermediate in acetonitrile (45 mL). The mixture was diluted with acetonitrile (10 mL) and stirred for 1 h at RT. Subsequently, the pH value of the reaction mixture was adjusted to 5.5 by addition of 5 M NaOH solution. Acetonitrile was removed under reduced pressure and the aqueous solution was extracted with DCM (4×100 mL). The combined organic phases were dried over $Na_2SO_4$ and volatiles were removed under reduced pressure. Crude 5b was used in the next step without further purification.

Yield: 2.52 g (3.19 mmol).

MS: m/z 519.3=[M+H]+ (MW calculated=519.8 g/mol).

Synthesis of Linker Reagent 5c

Intermediate 5b (985 mg, 1.9 mmol) and p-nitrophenyl chloroformate (330 mg, 2.5 mmol) were dissolved in anhydrous THF (10 mL). DIPEA (0.653 mL, 3.7 mmol) was added and the mixture was stirred for 2 h at RT. The solution was acidified by addition of acetic acid (1 mL). 5c was purified by RP-HPLC.

Yield: 776 mg, (1.13 mmol).

MS m/z 706.3=[M+Na]$^+$ (MW calculated=706.3).

Synthesis of Peptide Linker Reagent a) Peptide Synthesis

The solid phase peptide syntheses were performed for example on a Prelude Peptide Synthesizer (Protein Technologies Inc) or similar automated synthesizer using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF 2× for 20 min. Washes: 5×DMF.

b) N-Terminal Elongation with D-Ala 0.9 mmol resin bound peptide (equivalent to 4 g resin) synthesized as described in step a with a free amino group at the N-terminus was split into five equal portions. Each portion was suspended in 15 ml DMF and subsequently 2.5 eq. Fmoc-D-Ala-OH, 2.5 eq. HATU, 2.5 eq. HOAt and 2.5 eq. DIPEA were added. The mixture was agitated for 16 h at ambient temperature. Then the reaction mixture was removed by filtration and the resin was washed 3 times with 18 ml DMF, 18 ml DCM, 18 ml iso-propanol, 18 ml diethyl ether. The remaining solvents were removed in vacuo.

c) Fmoc Deprotection, Linker Attachment and Cleavage

Then the resin was suspended in 10 ml DMF and 2.5 eq. of tert-butyl (2-(((4-nitrophenoxy)carbonyl)amino)ethyl)(6-(tritylthio)hexyl)carbamate 5c and 2.5 eq. DIPEA were added. The mixture was agitated for 16 h at ambient temperature. Then the reaction mixture was removed by filtration and the resin was washed 3 times with 15 ml DMF, 15 ml DCM, 15 ml iso-propanol, 15 ml diethyl ether. The remaining solvents were removed in vacuo. The reaction was tested for completion by a Kaisertest Then a mixture of TFA/DTT/TIS/H$_2$O/thioanisole/Bu$_4$NBr (100/3/2/3/1/0.05) was added and the mixture was agitated for 3.5 h. The mixture was filtrated and the resin was washed with 1 ml TFA. The combined filtrates were added to 100 ml cooled diethyl ether. The precipitate was isolated by centrifugation and it was washed 2 times with 100 ml diethyl ether.

The crude product was purified via preparative HPLC on a Waters column (XBridge, BEH130, Prep C18 5 µM) using an acetonitrile/water gradient (both buffers with 0.1% TFA). The purified intermediate was immediately lyophilized and stored in an Ar atmosphere or used directly for the next step.

Example 6

Synthesis of GLP-1/Glucagon Agonist Linker Reagent 6d (Ala Linker)

GLP-1/Glucagon agonist linker reagent 6d was synthesized according to the following scheme:

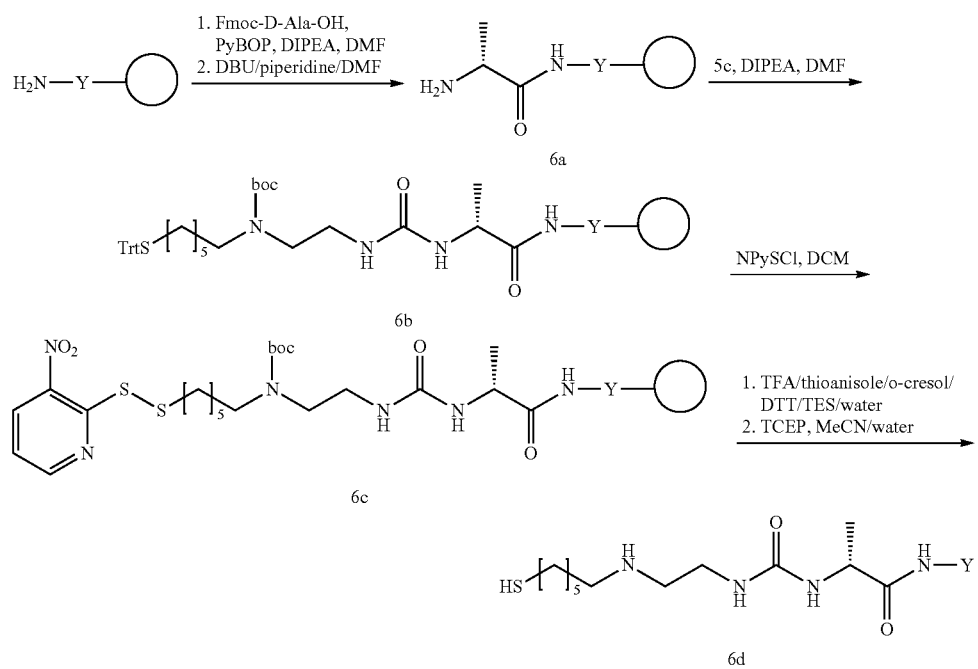

0.37 mmol resin bound peptide (equivalent to 1.6 g resin) synthesized as described in step b with a free amino group at the N-terminus was split into two equal portions. Each portion was suspended in 12 ml of a 20% solution of piperidine in DMF and agitated for 5 min. The solvent was removed and the procedure was repeated twice.

The resin bound peptide was washed 5 times with 12 ml DMF.

Synthesis of GLP-1/Glucagon agonist linker reagent intermediate 6a: Fully side chain protected GLP-1/Glucagon agonist with free N-terminus on resin (2.00 g, 0.2 mmol, loading approximately 0.1 mmol/g) was transferred into a 20 mL syringe equipped with a filter frit. 8 mL of anhydrous DMF was drawn into the syringe and the syringe was shaken (600 rpm) for 15 min in order to pre-swell the resin. The solvent was discarded, and a solution of Fmoc-D-alanine- OH (187 mg, 0.6 mol), PyBOP (312 mg, 0.6 mmol), and DIPEA (174 µL, 1.0 mmol) in anhydrous DMF (4 mL) was drawn into the syringe. The syringe was shaken at RT and 600 rpm for 60 min. The solution was discharged, and the resin was washed ten times with DMF.

Fmoc-deprotection was performed as described above.

Synthesis of GLP-1/Glucagon Agonist Linker Reagent Intermediate 6b

A solution of 5c (137 mg, 0.4 mmol) in anhydrous DMF (3 mL) was added to the resin 6a (0.2 mmol), followed by a solution of DIPEA (80 µL, 0.46 mmol) in anhydrous DMF (4.5 mL), and the reaction mixture was shaken (600 rpm) at 22° C. for 15 hours.

The resin was washed ten times with DMF and ten times with DCM and dried in vacuo.

Synthesis of GLP-1/Glucagon Agonist Linker Reagent Intermediate 6c

3-Nitro-2-pyridine-sulfenyl chloride (48 mg, 0.25 mmol) was given into a syringe containing 6b (0.05 mmol, 0.5 g). Anhydrous DCM (4 mL) was drawn into the syringe and the mixture was shaken (600 rpm) at RT. After 2 h the solution was discarded and the resin was washed 14 times with DCM and dried in vacuo.

Synthesis of GLP-1/Glucagon Agonist Linker Reagent Intermediate 6d

In a round bottom flask o-cresol (1.5 mL), thioanisole (1.5 mL), DTT (1.125 g), TES (1.125 mL), and water (1.5 mL) were dissolved in TFA (37.5 mL). 6c (0.15 mmol, 1.5 g) was added to the stirred (250-350 rpm) solution at RT in order to obtain a homogeneous suspension. Stirring was continued for 45 min. The solution was separated from the resin beads by filtration, the beads were washed with TFA twice (2 mL each) and the washing solutions were combined with the filtrate. TFA was removed from the combined solutions in a stream of nitrogen.

Crude 6d was precipitated from the concentrated solution (approx. 10 mL) by addition of diethyl ether (30 mL) and vigorous shaking. After centrifugation (2 min, 5000 rpm) the supernatant was discarded and the precipitate was washed with diethyl ether twice (20 mL each).

Dried precipitate was dissolved in a solution of TCEP (114 mg, 0.39 mmol) in 30 ml 1/19 (v/v) acetonitrile/water containing 0.01% TFA (v/v). Mixture was incubated for 15 hours at RT. 6d was purified by RP-HPLC as described in Materials and Methods using a 150×30 mm Waters XBridge™ BEH300 C18 10 µm column and a flow of 40 ml/min.

Up to 12 mL of the mixture were loaded on the column. The elution was performed using a linear gradient from 5% to 30% solvent B (5 min) followed by a linear gradient from 30% to 35% solvent B (40 min). Fractions containing product 6d were pooled and lyophilized. Purity: 86% (215 nm)

Yield: 85.2 mg (19.2 µmol, starting from 2.00 g resin).

MS m/z 1486.7=[M+3H]$^{3+}$, (MW calculated=4460.0 g/mol).

Example 7 (Asn Linker)

Synthesis of Linker Reagent 7f

Linker reagent 7f was synthesized according to the following scheme:

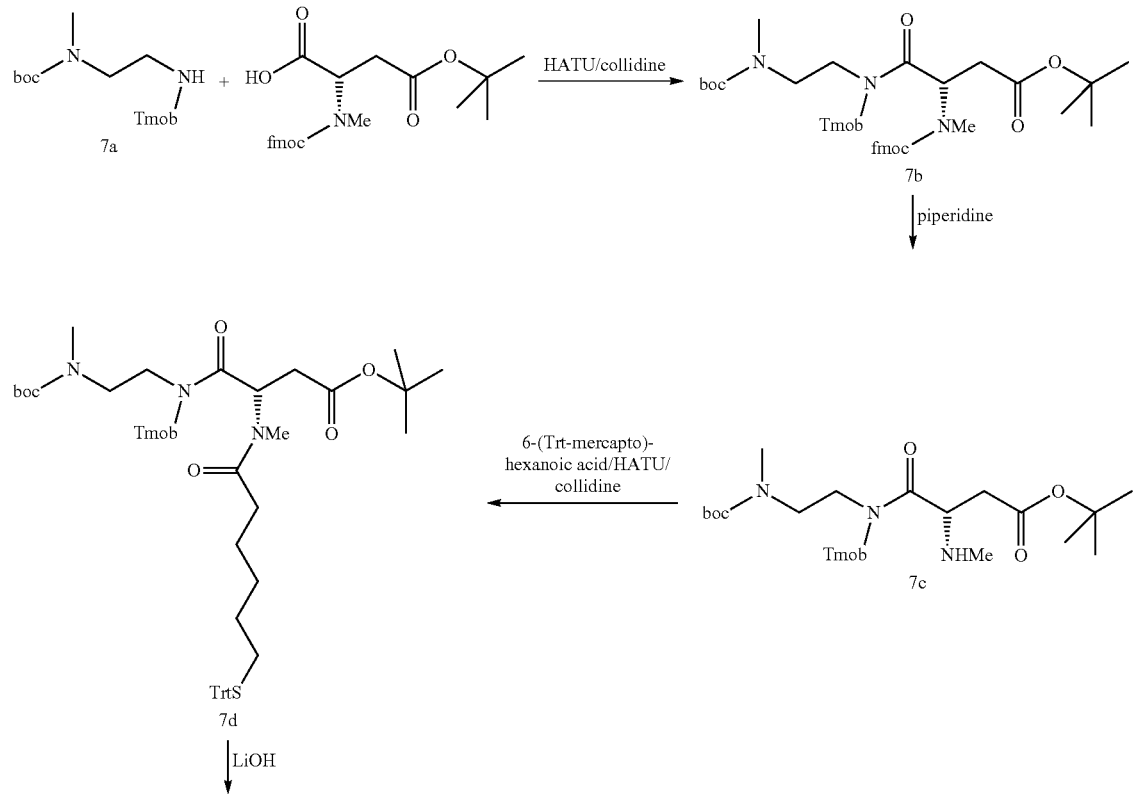

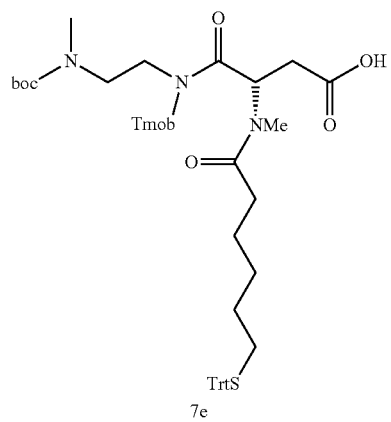
7e

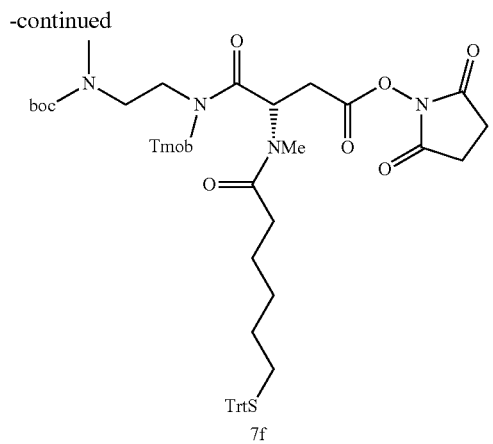
7f

To a cooled (0° C.) solution of N-Methyl-N-boc-ethylendiamine (0.5 mL, 2.79 mmol) and NaCNBH₃ (140 mg, 2.23 mmol) in MeOH (10 mL) and acetic acid (0.5 mL) was added a solution of 2,4,6-trimethoxybenzaldehyde (0.547 mg, 2.79 mmol) in EtOH (10 mL). The mixture was stirred at RT for 2 h, acidified with 2 M HCl (1 mL) and neutralized with saturated aqueous Na₂CO₃ (50 mL). Evaporation of all volatiles, DCM extraction of the resulting aqueous slurry and concentration of the organic fractions yielded N-Methyl-N-boc-N'-tmob-ethylendiamine (7a) as a crude oil which was purified by RP-HPLC.

Yield: 593 mg (1.52 mmol)

MS: m/z 377.35=[M+Na]⁺, (calculated=377.14).

N-Fmoc-N-Me-Asp(OtBu)-OH (225 mg, 0.529 mmol) was dissolved in DMF (3 mL) and 7a (300 mg, 0.847 mmol), HATU (201 mg, 0.529 mmol), and collidine (0.48 mL, 3.70 mmol) were added. The mixture was stirred at RT for 2 h to yield 7b. For fmoc deprotection, piperidine (0.22 mL, 2.16 mmol) was added and stirring was continued for 1 h. Acetic acid (1 mL) was added, and 7c was purified by RP-HLPC.

Yield: 285 mg (0.436 mmol as TFA salt)

MS: m/z 562.54=[M+Na]⁺, (calculated=562.67).

6-Tritylmercaptohexanoic acid (0.847 g, 2.17 mmol) was dissolved in anhydrous DMF (7 mL). HATU (0.825 g, 2.17 mmol), and collidine (0.8 mL, 6.1 mmol) and 7c (0.78 g, 1.44 mmol) were added. The reaction mixture was stirred for 60 min at RT, acidified with AcOH (1 mL) and purified by RP-HPLC. Product fractions were neutralized with saturated aqueous NaHCO₃ and concentrated. The remaining aqueous phase was extracted with DCM and 7d was isolated upon evaporation of the solvent.

Yield: 1.4 g (94%)

MS: m/z 934.7=[M+Na]⁺, (calculated=934.5).

To a solution of 7d (1.40 mg, 1.53 mmol) in MeOH (12 mL) and H₂O (2 mL) was added LiOH (250 mg, 10.4 mmol) and the reaction mixture was stirred for 14 h at 70° C. The mixture was acidified with AcOH (0.8 mL) and 7e was purified by RP-HPLC. Product fractions were neutralized with saturated aqueous NaHCO₃ and concentrated. The aqueous phase was extracted with DCM and 7e was isolated upon evaporation of the solvent.

Yield: 780 mg (60%)

MS: m/z 878.8=[M+Na]⁺, (calculated=878.40).

To a solution of 7e (170 mg, 0.198 mmol) in anhydrous DCM (4 mL) were added DCC (123 mg, 0.59 mmol) and N-hydroxy-succinimide (114 mg, 0.99 mmol), and the reaction mixture was stirred at RT for 1 h. The mixture was filtered, and the filtrate was acidified with 0.5 mL AcOH and 7f purified by RP-HPLC. Product fractions were neutralized with saturated aqueous NaHCO₃ and concentrated. The remaining aqueous phase was extracted with DCM and 7f was isolated upon evaporation of the solvent.

Yield: 154 mg (0.161 mmol)

MS: m/z 953.4=[M+H]⁺, (calculated=953.43).

Alternatively, linker reagent 7f was synthesized according to the following procedure: Alternative reaction scheme:

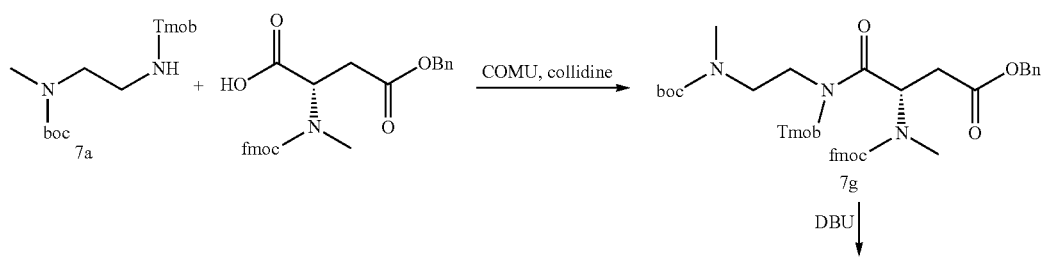

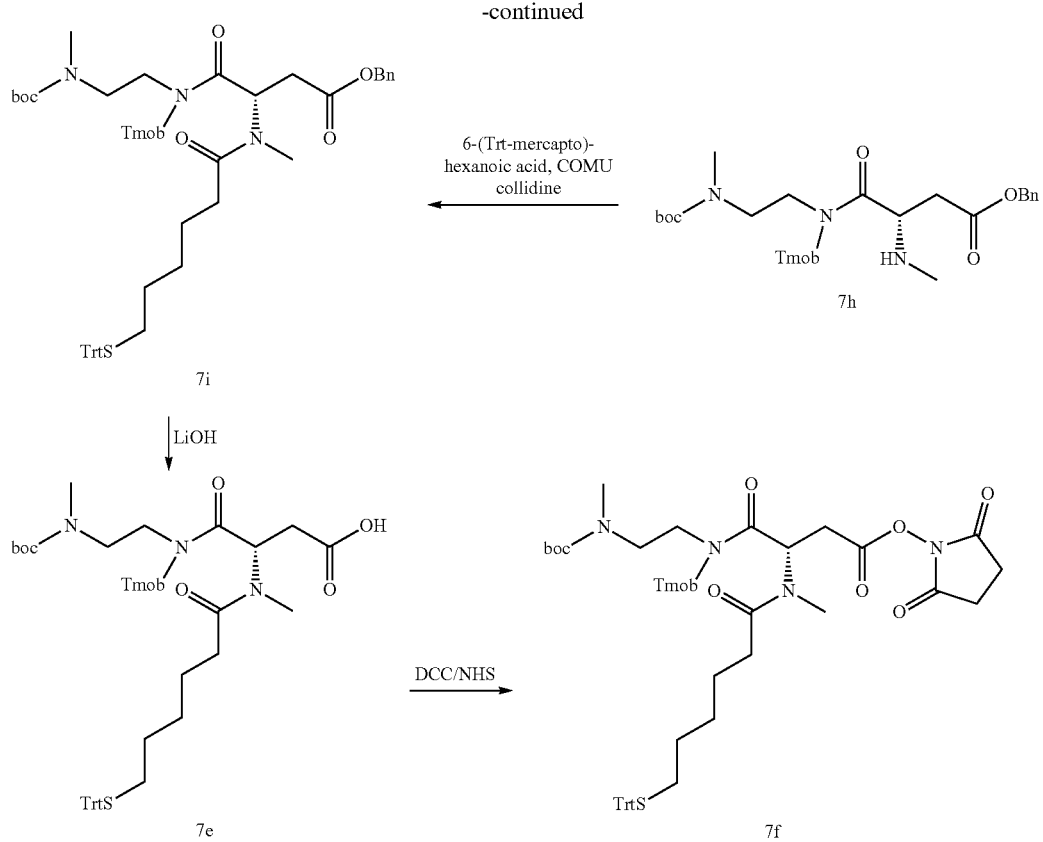

To a solution of N-Methyl-N-boc-ethylenediamine (2 g, 11.48 mmol) and NaCNBH₃ (819 mg, 12.63 mmol) in MeOH (20 mL) was added 2,4,6-trimethoxybenzaldehyde (2.08 mg, 10.61 mmol) portion wise. The mixture was stirred at RT for 90 min, acidified with 3 M HCl (4 mL) and stirred further 15 min. The reaction mixture was added to saturated NaHCO₃ solution (200 mL) and extracted 5× with CH₂Cl₂. The combined organic phases were dried over Na₂SO₄ and the solvents were evaporated in vacuo. The resulting N-Methyl-N-boc-N'-tmob-ethylenediamine (7a) was completely dried in high vacuum and used in the next reaction step without further purification.

Yield: 3.76 g (11.48 mmol, 89% purity, 7a: double Tmob protected product=8:1)

MS: m/z 355.22=[M+H]$^+$, (calculated=354.21).

To a solution of 7a (2 g, 5.65 mmol) in CH₂Cl₂ (24 ml) COMU (4.84 g, 11.3 mmol), N-Fmoc-N-Me-Asp(OBn)-OH (2.08 g, 4.52 mmol) and collidine (2.65 mL, 20.34 mmol) were added. The reaction mixture was stirred for 3 h at RT, diluted with CH₂Cl₂ (250 mL) and washed 3× with 0.1 M H₂SO₄ (100 ml) and 3× with brine (100 ml). The aqueous phases were re extracted with CH₂Cl₂ (100 ml). The combined organic phases were dried over Na₂SO₄, filtrated and the residue concentrated to a volume of 24 mL. 7 g was purified using flash chromatography.

Yield: 5.31 g (148%, 6.66 mmol)

MS: m/z 796.38=[M+H]$^+$, (calculated=795.37).

To a solution of 7 g [5.31 g, max. 4.51 mmol ref. to N-Fmoc-N-Me-Asp(OBn)-OH] in THF (60 mL) DBU (1.8 mL, 3% v/v) was added. The solution was stirred for 12 min at RT, diluted with CH₂Cl₂ (400 ml) and washed 3× with 0.1 M H₂SO₄ (150 ml) and 3× with brine (150 ml). The aqueous phases were re extracted with CH₂Cl₂ (100 ml). The combined organic phases were dried over Na₂SO₄ and filtrated. 7h was isolated upon evaporation of the solvent and used in the next reaction without further purification.

MS: m/z 574.31=[M+H]$^+$, (calculated=573.30).

7h (5.31 g, 4.51 mmol, crude) was dissolved in acetonitrile (26 mL) and COMU (3.87 g, 9.04 mmol), 6-Tritylmercaptohexanoic acid (2.12 g, 5.42 mmol) and collidine (2.35 mL, 18.08 mmol) were added. The reaction mixture was stirred for 4 h at RT, diluted with CH₂Cl₂ (400 ml) and washed 3× with 0.1 M H₂SO₄ (100 ml) and 3× with brine (100 ml). The aqueous phases were re extracted with CH₂Cl₂ (100 ml). The combined organic phases were dried over Na₂SO₄, filtrated and 7i was isolated upon evaporation of the solvent. Product 7i was purified using flash chromatography.

Yield: 2.63 g (62%, 94% purity)

MS: m/z 856.41=[M+H]$^+$, (calculated=855.41).

To a solution of 7i (2.63 g, 2.78 mmol) in i-PrOH (33 mL) and H₂O (11 mL) was added LiOH (267 mg, 11.12 mmol) and the reaction mixture was stirred for 70 min at RT. The mixture was diluted with CH₂Cl₂ (200 ml) and washed 3× with 0.1 M H₂SO₄ (50 ml) and 3× with brine (50 ml). The aqueous phases were re-extracted with CH₂Cl₂ (100 ml). The combined organic phases were dried over Na₂SO₄, filtrated and 7e was isolated upon evaporation of the solvent. 7j was purified using flash chromatography.

Yield: 2.1 g (88%)

MS: m/z 878.4=[M+Na]$^+$, (calculated=878.40).

To a solution of 7e (170 mg, 0.198 mmol) in anhydrous DCM (4 mL) were added DCC (123 mg, 0.59 mmol), and a catalytic amount of DMAP. After 5 min N-hydroxysuccinimide (114 mg, 0.99 mmol) was added and the reaction mixture was stirred at RT for 1 h. The reaction mixture was filtered, the solvent was removed in vacuo and the residue was taken up in 90% acetonitrile plus 0.1% TFA (3.4 ml). The crude mixture was purified by RP-HPLC. Product fractions were neutralized with 0.5 M pH 7.4 phosphate buffer and concentrated. The remaining aqueous phase was extracted with DCM and 7f was isolated upon evaporation of the solvent.

Yield: 154 mg (81%)

MS: m/z 953.4=[M+H]$^+$, (calculated=953.43).

Example 8

Synthesis of Linker Reagent 8e

Linker reagent 8e was synthesized according to the following scheme:

dried (Na$_2$SO$_4$) and solvent was removed under reduced pressure. Phthalimide 8c was purified on silica by using heptane (containing 0.02 NEt$_3$) and an ascending amount of ethyl acetate (containing 0.02% NEt$_3$) as eluents.

Yield: 0.82 g (1.46 mmol)

MS: m/z 563.3=[M+H]$^+$ (MW calculated=562.8).

Phthalimide 8c (819 mg 1.46 mmol) was dissolved in 35 mL ethanol and hydrazine hydrate (176 μl, 3.64 mmol) was added. Mixture was refluxed for 3 h. Precipitate was filtered off. Solvent was removed under reduced pressure and residue was treated with 15 mL dichloromethane. Precipitate was filtered off and dichloromethane was removed under reduced pressure. Residue was purified by RP HPLC. Pooled HPLC fractions were adjusted to pH 7 by adding NaHCO$_3$ and extracted several times with dichloromethane. Combined organics were dried (Na$_2$SO$_4$) and solvent was removed under reduced pressure to yield amine 8d.

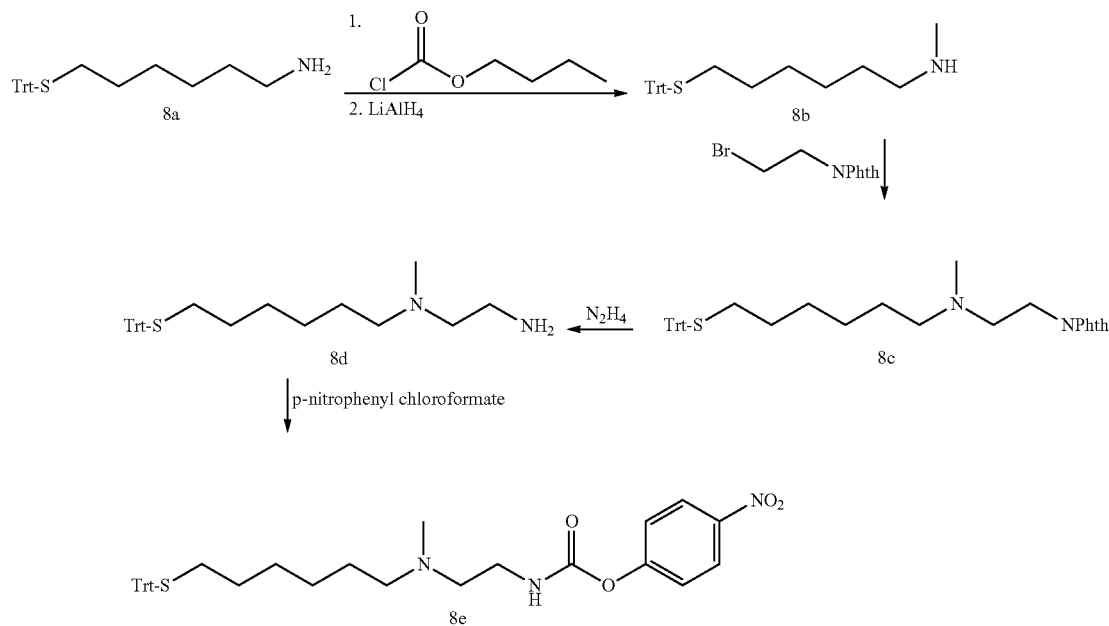

Synthesis of linker reagent intermediate 8b was performed under nitrogen atmosphere. A solution of amine 8a (1.69 g, 4.5 mmol, for preparation see WO-A 2009/133137) in 30 mL THF (dry, mol. sieve) was cooled to 0° C. Butyl chloroformate (630 μl, 4.95 mmol) in 3 mL THF (dry, mol. sieve) and DIPEA (980 μl, 5.63 mmol) were added. Mixture was stirred for 10 min at 0° C., cooling was removed and mixture stirred for further 20 min at RT. 1 M LiAlH$_4$ in THF (9 mL, 9 mmol) was added and mixture was refluxed for 1.5 h. Reaction was quenched by slowly adding methanol (11 mL) and 100 mL sat. Na/K tartrate solution. Mixture was extracted with ethyl acetate, organic layer was dried over Na$_2$SO$_4$ and solvent was evaporated under reduced pressure. Crude product 8b (1.97 g) was used in the next step without further purification.

MS: m/z 390.2=[M+H]$^+$ (MW calculated=389.6).

A solution of crude product 8b (1.97 g), N-(bromoethyl)-phthalimide (1.43 g, 5.63 mmol) and K$_2$CO$_3$ (1.24 g, 9.0 mmol) in 120 mL acetonitrile was refluxed for 6 h. 60 mL of a sat. NaHCO$_3$ solution was added and mixture was extracted 3× with ethyl acetate. Combined organics were Yield: 579 mg (1.34 mmol)

MS: m/z 433.3=[M+H]+(MW calculated=432.7).

Para-nitrophenyl chloroformate (483 mg, 2.40 mmol) was dissolved in 10 mL dichloromethane (dry, mol. sieve). A solution of amine 8d (1.00 g, 2.31 mmol) in 5 mL dichloromethane (dry, mol. sieve) and 1.8 mL of sym-collidine were added and mixture was stirred at room temperature for 40 min. Dichloromethane was removed under reduced pressure, residue was acidified with acetic acid and purified by RP-HPLC to yield para-nitrophenyl carbamate 8e.

Yield: 339 mg (0.57 mmol)

MS: m/z 598.3=[M+H]$^+$ (MW calculated=597.8).

Synthesis of Peptide-Linker—Polymer Conjugates

Example 9

Synthesis of GLP/Glucagon agonist thiol linker 1 was synthesized according to the following scheme:

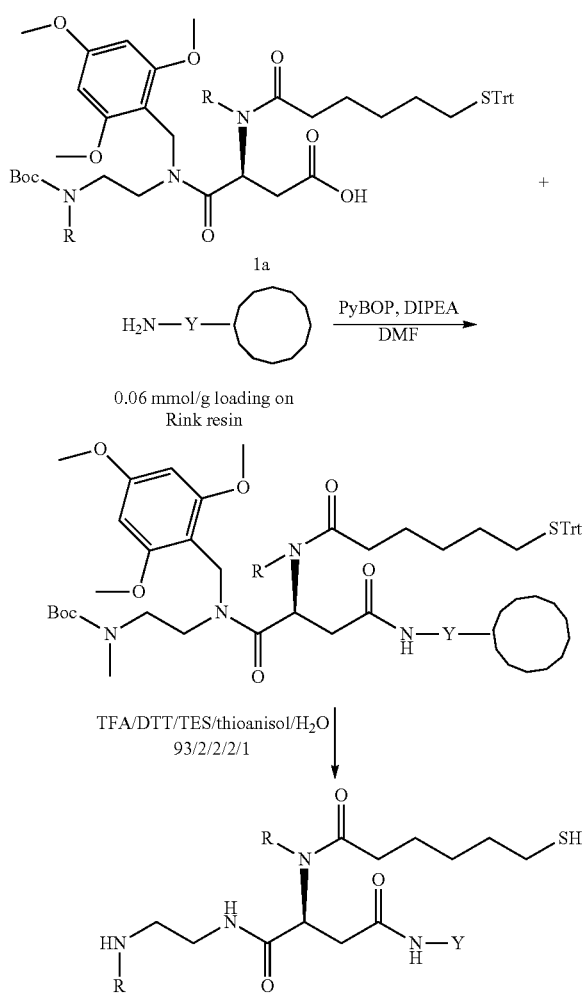

R = H, CH₃

To 400 mg of the resin bound Fmoc-protected Exendin-4 Seq. ID. 26 on rink resin in a peptide synthesis vessel was added 4 ml of 20% piperidine in DMF and the reaction mixture was stirred for 5 minutes. The process was repeated three times. The resin bound peptide was subsequently washed with 4 ml of DMF three times.

To 80 mg (2.5 eqv.) of the linker 1a and 60 mg (3.0 eqv.) of PyBOP was added 5 mL of anhydrous DMF. To this solution was added 16 µl (3.0 eqv.) of diisoproyldiethyamine (DIPEA). The resulting solution was added to above processed resin bound Exendin-4 Seq ID. 3126-resin. The mixture was allowed to proceed for 18 hr. at 25° C. At the end of this time, the resin filtered and washed with anhydrous DMF (5 ml×5), dichloromethane (5 ml×5), isopropanol (5 ml×5) and diethyl ether (5 ml×5).

The above resin bound peptide-linker conjugate was treated with 10 ml of a solution containing trifluoroacetic acid (TFA)/triethylsilane(TES)/dithiothreitol (DTT)/Thioanisole/water (100/2/3/1/2). The reaction mixture was shaken at 25° C. for 3 hr. At the end of reaction, the solvent was filtered off and the resin was washed with dichloromethane (5×10 ml). The filtrate was concentrated under reduced pressure. The residue was poured into 50 ml ice-cold ether. White solid precipitated out. The mixture was centrifuged and decanted. The solid was washed with diethyl ether (2×20 ml). The peptide-linker was purified by reverse phase HPLC (30×100 mm C18 column, 25-40% AcCN/H₂O w/0.1% TFA in 20 min.). The appropriate fractions were collected and evaporated to dryness yielding 16 mg of the desired product as a white solid. The product was identified my mass spectrometry (molecular ion peak, m/z 1469, z=3).

Example 10

GLP/Glucagon thiol linker 2 was synthesized according to the following scheme:

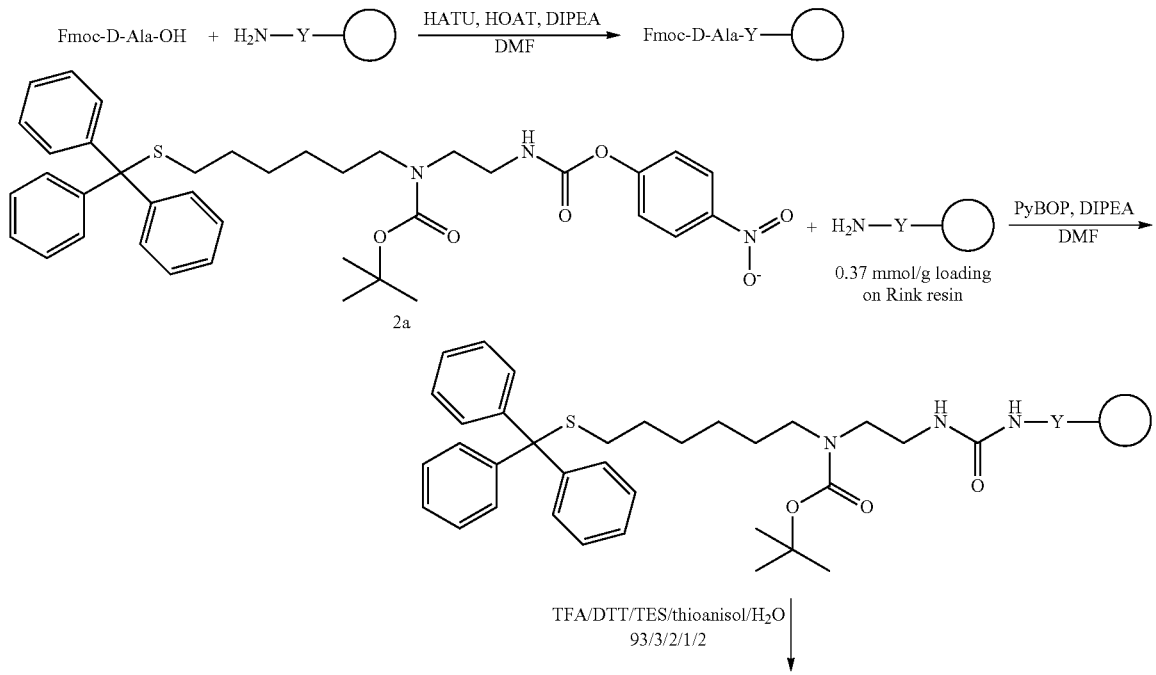

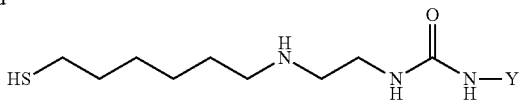

To 1.8 g of the resin bound Fmoc-protected Exendin-4 Seq ID. 26 on rink resin in a peptide synthesis vessel was added 20 ml of 20% piperidine in DMF and the reaction mixture was stirred for 5 minutes. The process was repeated three times. The resin bound peptide was subsequently washed with 20 ml of DMF three times.

To 163 mg (2.5 eqv.) Fmoc-D-Ala-OH, 199 mg (2.5 eqv.) of HATU and 71 mg (2.5 eqv.) of HOAt was added 15 ml of anhydrous DMF. To this solution was added 92 μl (2.5 eqv.) of diisoproyldiethyamine (DIPEA). The resulting solution was added to above processed resin bound Exendin-4 Seq ID. 26-resin. The mixture was allowed to proceed for 16 hr. at 25° C. At the end of this time, the resin filtered and washed with anhydrous DMF (20 ml×5), dichloromethane (20 ml×5), isopropanol (20 ml×5) and diethyl ether (20 ml×5).

To the above resin bound Fmoc-protected D-Ala-Exendin-4-Seq ID. 26 on rink resin in a peptide synthesis vessel was added 15 ml of 20% piperidine in DMF and the reaction mixture was stirred for 5 minutes. The process was repeated three times. The resin bound peptide was subsequently washed with 15 ml of DMF three times.

To 352 mg (2.5 eqv.) of the linker 2a was added 15 mL of anhydrous DMF. To this solution was added 92 μl (2.5 eqv.) of diisoproyldiethyamine (DIPEA). The resulting solution was added to above processed resin bound D-Ala-Exendin-4 Seq ID. 26-resin. The mixture was allowed to proceed for 16 hr. at 25° C. At the end of this time, the resin filtered and washed with anhydrous DMF (15 ml×5), dichloromethane (15 ml×5), isopropanol (15 ml×5) and diethyl ether (15 ml×5).

The above resin bound peptide-linker conjugate was treated with 40 ml of a solution containing trifluoroacetic acid (TFA)/triethylsilane(TES)/dithiothreitol (DTT)/Thioanisole/water (100/2/3/1/2). The reaction mixture was shaken at 25° C. for 1 hr. At the end of reaction, the solvent was filtered. The filtrate was poured into 400 ml ice-cold ether. White solid precipitated out. The mixture was centrifuged and decanted. The solid was washed with diethyl ether (2×200 ml). The peptide-linker was purified by reverse phase HPLC (30×100 mm C18 column, 25-40% AcCN/H$_2$O w/0.1% TFA in 20 min.). The appropriate fractions were collected and evaporated to dryness yielding 104 mg of the desired product as a white solid. The product was identified my mass spectrometry (molecular ion peak, m/z 1465.3, z=3 and m/z 1099.2, z=4).

Synthesis of Hyaloronic Acid Hydrogels

Example 11

Divinyl sulfone crosslinked hyaluronic acid was synthesized according to the following scheme:

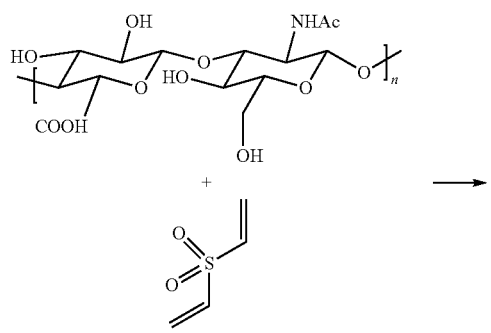

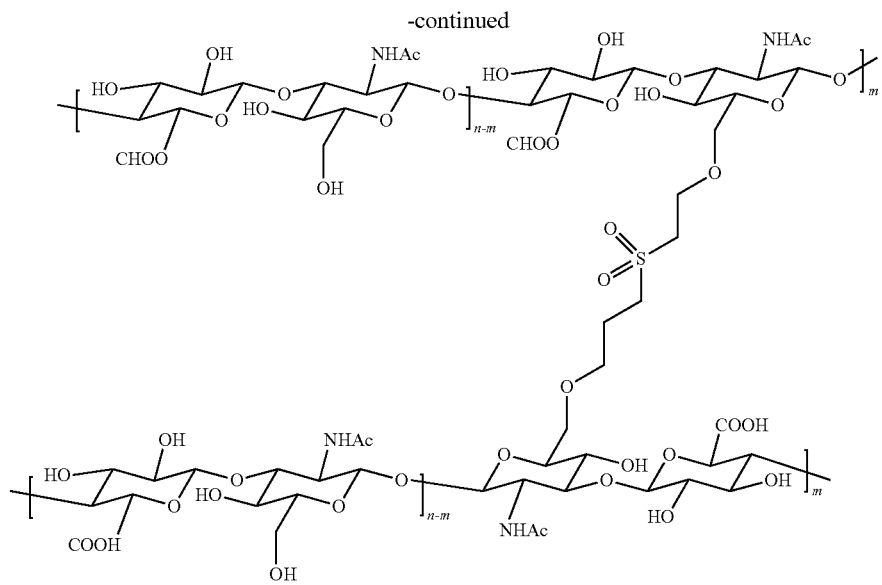

Example 11a

To 0.2M sodium hydroxide (168.9 g) was added sodium chloride (23.4 g) with stirring until dissolved. To the solution under rapid mechanical stirring was added sodium hyaluronate (25.4 g, 400-500 KDa) which continued for 2h. The resulting polymer solution has a concentration of ~12% w/w. A solution of divinylsulfone (0.41 mL, 0.48 g) in isopropanol (1.6 mL) was prepared and added (5×0.4 mL) over ~30 sec. The mixture was stirred for an additional 2 min and poured into a 23×28×6.5 cm glass tray and sealed with a plastic cover. After standing at RT for 4h the gel was transferred as a single piece to a solution of 1M hydrochloric acid (100.1 g) in 0.9% saline (3 kg). It was agitated gently at RT. After 24h the pH of the solution was 2.28. The solution discarded leaving a gel (416.2 g). To the gel was then added 0.9% saline (3 kg) and it was agitated gently at RT for 18h. To the mixture was added 1M sodium hydroxide (9.7 mL) at 0, 2, 4, 6 and 8h. The gel was gently agitated for a further 24h at RT at which time the pH of the gel was 6.65. The gel was stored at 2-8° C. for 120h and then 10 mM sodium phosphate solution pH 7.4 (2 L) was added. The gel was agitated for an additional 21 h and the wash discarded leaving a gel (1036.2 g) with a final polymer concentration of 2.4%.

Example 11b. Alternative Synthesis of Divinylsulphone Crosslinked Hyaluronic Acid To 35 g of sodium hyaluronate was added 946 mL of sterile water. The reaction mixture was kept at 2-8° C. for 7 days, during which time a clear solution has formed. To this solution was added 1M 111 mL of 1.0 M sodium hydroxide solution and the resulting reaction mixture was stirred vigorously for 5 min. The reaction mixture was kept at 2-8° C. for 90 min. Subsequently a suspension of 6.7 mL of divinylsulphone in 10 mL of sterile water was to the polymer solution and the resulting reaction mixture was stirred vigorously for 5 minutes. Subsequently, reaction mixture was stored at 2-8° C. for 150 minutes followed by for 90 minutes at 25° C. The polymer gel thus formed was washed with 0.9% sterile saline for four days. The pH of the suspension was adjusted to 7.0 with either 1.) M NaOH or 1.0 M HCl. The final concentration of the gel suspension was 0.58%.

Example 12

Synthesis of 1-(tert-butoxycarbonyl) amino 3-(3-maleimidopropyl) aminopropane

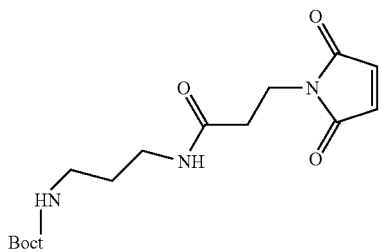

In 250 ml round bottomed flask were taken 3.0 g of 1-(tert-Butoxycarbonyl) amino 3-aminopropane) and 100 mL of anhydrous chloroform. The reaction mixture was stirred at 25° C. until a clear solution was formed. To this solution was added N-succinimidyl 3-maleimidopropionate (5.05 g) with stirring until dissolved followed 3.42 mL of diisoproylethylamine. The resulting reaction mixture was stirred at 25° C. for 18h. The solution was washed with 1M hydrochloric acid (50 mL), 10% brine (50 mL), saturated sodium bicarbonate (50 mL), semi-saturated brine (50 mL). The organic phase was isolated and was dried over anhydrous sodium sulfate. After removing the sodium sulfate by filtration, the solution was concentrated under reduced pressure and the residue was purified by silica gel column chromatography using ethyl acetate: hexanes gradient as the mobile phase. Removal of the solvent under reduced pressure followed by vacuum drying offered the desired product as an off white solid (4.03 g).

Example 13

Synthesis of 1-(tert-Butyloxycarbonyl)amino 8-(3-maleimidopropyl) amino-3,6-dioxaoctane In 100 ml round bottomed flask were taken 1-(tert-butyloxycarbonyl) amino 8-amino-3,6-dioxaoctane (1.007 g) and 25 mL of anhydrous acetonitrile (25 mL). The reaction mixture was stirred under nitrogen until dissolved. To this solution was added N-succinimidyl 3-maleimidopropionate (1.302 g) and the reaction mixture was stirred under nitrogen at 25° C. for 6h. At the end of this time, the solvent was removed under reduced pressure. The residue was purified silica gel column chromatography using dichloromethane containing 2-6% of methanol. After removing the solvent under reduced pressure and drying the residue under vacuum yielded 1.08 g of the desired product as an off white solid.

Example 14

Synthesis of 3-(3-maleimido-propyl) aminopropane Functionalized Hyaluronic Acid

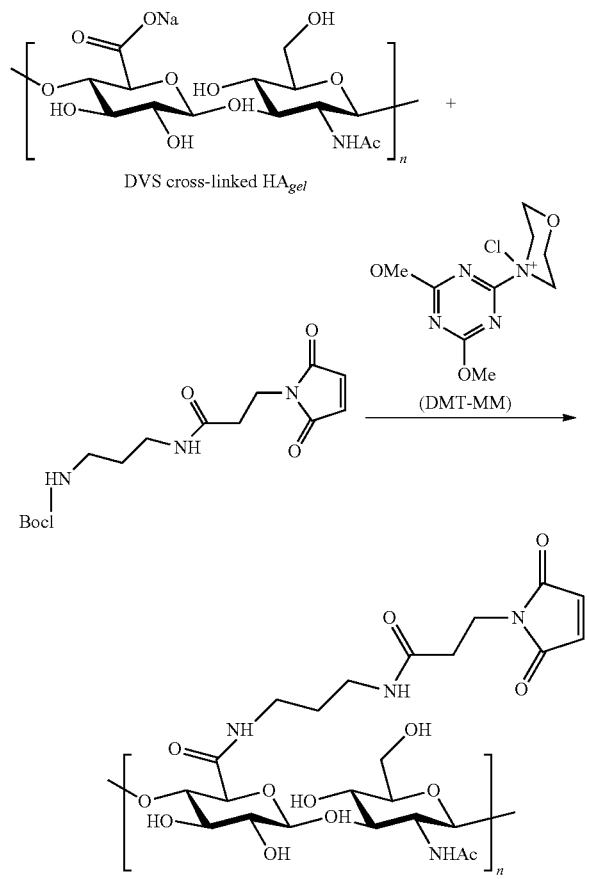

To 15 g of divinyl sulfone crosslinked suspension (Example 1) was added 45 ml of deionized (DI) water and the resulting suspension was stirred at 25° C. for 10 minutes. After adding 45 ml of ethanol to the suspension, it was stirred for additional 60 min. It was followed by addition of 60 mL of ethanol and 10 minute of stirring. To this suspension was added 0.24 g of 4-(4,6-dimethoxy-1,3,5-triazin-2-yl)-4-methyl-morpholinium chloride (DMT-MM) dissolved in 5 mL of ethanol. The resulting reaction mixture was stirred at 25° for 60 mins. To 70 mg of 1-(tert-Butoxycarbonyl) amino 3-(3-maleimidopropyl) aminopropane (example 2) dissolved in 2 mL of anhydrous dichloromethane was added 2 mL of trifluoroacetic acid. The resulting reaction was stirred at room temperature for 2h. The solution was concentrated under reduced pressure. The resulting residue was treated with 3 mL of methanol and evaporated to dryness. After repeating this process one more time the residue was dissolved in ethanol (5 mL) and the pH adjusted to 6-6.5 with 10% N-methylmorpholine in ethanol. The resulting solution was added to the above hyaluronic acid suspension. The vial was rinsed with ethanol (5 mL) and added to the slurry. After stirring for 18h at 25° C., saturated brine (2 mL) was added to the reaction mixture. The suspension was treated with ethanol (3×30 mL, 2×15 mL) to precipitate the polymer gel. The reaction mixture was centrifuged at 4000 rpm and the supernatant decanted. The residue was hydrated in DI water (20 mL) for ~20 min and was precipitated from ethanol (4×10 mL). Glucosamine assay method suggests the degree of substitution to be 19 mole %.

Example 15

Synthesis of 3-(3-maleimido-propyl) aminopropane Functionalized Hyaluronic Acid To 20 g of divinyl sulfone crosslinked suspension (Example 1) was added 60 ml of deionized (DI) water and the resulting suspension was stirred at 25° C. for 10 minutes. After adding 60 ml of ethanol to the suspension, it was stirred for additional 60 min. It was followed by addition of 60 mL of ethanol and 10 minute of stirring. To this suspension was added 0.325 g of DMT-MM dissolved in 10 mL of ethanol. The resulting reaction mixture was stirred at 25° for 60 mins. To 0.38 g of 1-(tert-Butoxycarbonyl) amino 3-(3-maleimidopropyl) aminopropane (example 2) dissolved in 2.5 mL of anhydrous dichloromethane was added 2.5 mL of trifluoroacetic acid. The resulting reaction was stirred at room temperature for 2h. The solution was concentrated under reduced pressure. The resulting residue was treated with 3 mL of methanol and evaporated to dryness. After repeating this process one more time, the residue was dissolved in ethanol (5 mL) and the pH adjusted to 6-6.5 with 10% N-methylmorpholine in ethanol. The resulting solution was added to the above hyaluronic acid suspension. The vial was rinsed with ethanol (5 mL) and added to the slurry. After stirring for 18h at 25° C., saturated brine (2 mL) was added to the reaction mixture. The suspension was treated with ethanol (3×30 mL, 2×15 mL) to precipitate the polymer gel. The reaction mixture was centrifuged at 4000 rpm and the supernatant decanted. The residue was hydrated in DI water (20 mL) for ~20 min and was precipitated from ethanol (4×10 mL). Glucosamine assay method suggests the degree of substitution to be 24 mole %.

Example 16a

General Method for the Synthesis of 3-(3-Maleimido-Propyl) Aminopropane Functionalized HA Hydrogel To appropriate amount divinylsulphone crosslinked HA suspension (Example 11b) was added sterile saline to obtain a gel concentration of ~1% w/v. The resulting suspension was stirred at 25° C. for 15-30 minutes. A water miscible organic solvent (preferably ethanol) was added to the suspension and the resulting suspension was stirred for additional 30-60 min. To this suspension was added appropriate amount of an ethanolic solution of 4-(4,6-dimethoxy-1,3,5-triazin-2-yl)-4-methyl-morpholinium chloride (DMT-MM). The container containing DMT-MM solution was rinsed twice with ethanol and the washings were added to the above suspension. The resulting reaction mixture was stirred at 25° C. for 90 minutes. Appropriate amount of 1-(tert-butoxycarbonyl) amino 3-(3-maleimidopropyl) aminopropane was dissolved in dichloromethane. To this solution was added trifluoroacetic acid to give a 1:1 (v/v) solution. After stirring at room temperature for 60-90 minutes, the reaction mixture was evaporated to dryness under reduced pressure. The residue was dissolved in ethanol and was added to the above suspension. The container containing maleimide derivative was rinsed twice with ethanol and the washings were added to the suspension. The pH of the suspension was adjusted to pH 6.4-6.6 using an organic or inorganic base (for example 10% N-methylmorpholine in ethanol). After stirring for 16-20h at 25° C., the suspension was treated with ethanol to a volume of 60-65% v/v. The solvent was removed from the reaction mixture either by centrifugation at 120G followed by decanting the supernatant or by applying a slight overpressure of $N_2$ gas to the system and filtering through a glass frit or filter membrane. The residue was subsequently treated with sterile 20 mM succinate saline (0.9%) at pH 3.8 for ~15-20 min and was precipitated by adding ethanol to a volume of 60-65% v/v. The solvent is removed from the reaction mixture by following the above procedure. This procedure was repeated one more time.

Example 16b

Synthesis of 3-(3-maleimido-propyl) aminopropane Functionalized HA Hydrogels at a Degree of Substitution of 20 Mole %

To 5.65 g of the HA hydrogel suspension (Example 11b) was added 7.5 mL of sterile saline and the resulting suspension was gently stirred for 15 minutes. To this suspension was added 3 mL of ethanol and the resulting reaction mixture was gently stirred for 60 min. To this suspension was added 94 mg of DMT-MM dissolved in 3 mL of ethanol. The vial containing the DMT-MM was washed with ethanol (2×1 mL) and the washings were added to the suspension. The reaction mixture was allowed to stir gently at ambient temperature for at 90 minutes. To 21.7 mg of 1-(tert-Butoxycarbonyl) amino 3-(3-maleimidopropyl)aminopropane was added 0.25 mL of dichloromethane and the reaction was gently mixed until a clear solution was formed. To this solution was added 0.25 mL of trifluoroacetic acid and was gently mixed at ambient temperature for 75 min. Subsequently, the solution was evaporated to dryness. The residue was dissolved in 3 mL of ethanol and the resulting solution added to the above hydrogel suspension. The vial containing the maleimide reagent was rinsed with ethanol (2×1 mL) and the washings were added to the reaction mixture. The pH of the reaction mixture was then adjusted to 6.41 using 10% v/v N-methylmorpholine in ethanol and the resulting reaction mixture was shaken gently for 18 hours at ambient temperature. At the end of this time, the pH of the reaction mixture adjusted to pH 3.89 by treating with 1.0 M HCl. The gel was precipitated by adding ethanol (4×3.5 mL). The suspension was centrifuged at 120G for 2 min at 20° C. and the supernatant was carefully removed using a pipette. The residue was rehydrated in 12 mL of 20.0 mM SBS buffer (pH 3.8) by gentle shaking/mixing for 15 minutes. The suspension was subjected to additional ethanol treatment (4×5 ml, 1×4 mL). After each ethanol treatment, the suspension was centrifuged at 120G for 2 min at 20° C. followed by careful removal of the supernatant. Finally, the vial was inverted, allowed to drain for 15 minutes and the supernatant was decanted yielding 0.8876 g of the wet gel.

Example 16c

Synthesis of 3-(3-maleimido-propyl) aminopropane Functionalized Hyaluronic Acid

To 10 g of divinyl sulfone crosslinked suspension (Example 11a) was added 40 ml of deionized (DI) water and the resulting suspension was stirred at 25° C. for 10 minutes. After adding 30 ml of ethanol to the suspension, it was stirred for additional 60 minutes. It was followed by addition of 60 mL of ethanol and 10 minute of stirring. To this suspension was added 0.162 g of DMT-MM dissolved in 7.5 mL of ethanol. The resulting reaction mixture was stirred at 25° C. for 60 mins. To 29 mg of 1-(tert-Butoxycarbonyl) amino 3-(3-maleimidopropyl) aminopropane (example 2) dissolved in 0.5 mL of anhydrous dichloromethane was added 0.5 mL of trifluoroacetic acid. The resulting reaction was stirred at room temperature for 2h. The solution was concentrated under reduced pressure. The resulting residue was treated with 2 mL of methanol and evaporated to dryness. After repeating this process one more time, the residue was dissolved in ethanol (7.5 mL) and 9.5 μL of N-methylmorpholine. The solution was added the above hyaluronic acid suspension and pH adjusted to 7.1 with using N-methylmorpholine. The vial was rinsed with ethanol (5 mL) and added to the slurry. After stirring for 21 h at 25° C., saturated brine (2 mL) was added and the gel was precipitated by adding ethanol (4×15 mL). The slurry was allowed to settle for 15 min and the supernatant was decanted. The hydrogel was hydrated in 20 mM PBS pH5 (35 mL) and was precipitated by adding ethanol (5×15 mL). The process was repeated, the sample centrifuged at 2500 rpm for 1.5 min, and the supernatant decanted. Glucosamine assay method suggests the degree of substitution to be 24 mole %.

Example 17

Synthesis of 8-(3-maleimidopropyl) amino-3,6-dioxaoctane Functionalized Hyaluronic Acid In a 250 mL round bottomed flask were taken 0.5 g of lyophilized HA (example 11a) and 50 mL of 0.9% saline solution. The reaction mixture was allowed to stir gently at 25° C. for one hr. To this suspension was added 40 mL of ethanol and the suspension was stirred for 5 min. In a 10 mL vial were taken 0.35 g of DMT-MM and 5 mL of ethanol.

The solution was added to the HA suspension. The vial was rinsed with 5 mL of ethanol and added to the suspension. The resulting reaction mixture was stirred at 25° C. for 1 hr. Subsequently, 86 mg of 1-(tert-Butyloxycarbonyl) amino 8-(3-maleimidopropyl) amino-3,6-dioxaoctane dissolved in 0.5 mL of anhydrous dichloromethane was treated with 0.5 mL of trifluoroacetic acid was added to the. The solution was stirred at room temperature from 1 h. The solution was concentrated under reduced pressure, dissolved in 2 mL of ethanol and evaporated to dryness under reduced pressure. The ethanol treatment was repeated twice. The residue was dissolved in 5 mL of ethanol/water (1:1) and the pH of the solution was adjusted to 6.5 using N-methylmorpholine (60 µL). The resulting solution was added to the above suspension. After stirring for 4h at 25° C., pH of suspension was adjusted to 3.75 with 0.1 M HCl and the gel was precipitated by adding ethanol (7×25 mL). The slurry was allowed to settle for 30 min and 80% of the supernatant removed decantation. The remaining suspension was centrifuged at 1500 rpm for 5 min. After removing the solvent, the residue was treated with 0.9% saline and precipitated from ethanol (7×15 mL). The residue was dried by lyophilization. The degree substitution, as determined by glucosamine assay was found to be 7.3 mol %.

Example 18

Synthesis of 2-pyridyldithiol Group Containing Hyaluronic Acid

To a rapidly stirring solution of 200 mg sodium hyaluronate (molecular weight=500 kDa) dissolved in 24 mL of deionized water was added 16 mL acetonitrile in dropwise manner. After addition of acetonitrile was complete, 17.6 mg of chlorodimethoxytriazine in 2 mL of water/acetonitrile (1:1) to the reaction mixture followed by 20 µL of N-methylmorpholine. The reaction was stirred at 25° C. for 1 hr. Subsequently, 26.8 mg of 2-((3-nitropyridin-2-yl)thio) ethanamine hydrochloride dissolved in 1 mL of deionized water was added. The reaction was allowed to stir for 18 hr. The pH of the reaction was adjusted to 6.0 by adding 1M HCl. To the resulting reaction mixture was added 15 mL of pre-washed Amberlite® CG-120 ($Na^+$ form) and the reaction mixture was stirred for 20 minutes. The resin was filtered off and was washed with deionized water (2×5 mL). The Amberlite® CG-120 ($Na^+$ form) treatment process was repeated twice. The solution was diluted with water to form a solution containing 20 vol % of acetonitrile. The solution was spin-filtered using Macrosep® centrifugal devices (30K molecular weight cutoff). The retentate was washed with deionized water (5×200 ml). The retentates were combined and lyophilized yielding 120 mg of the product as an off white solid. The degree of modification was 10%. Another 2-pyridyldithiol group containing hyaluronic acid was synthesized using sodium hyaluronate of molecular weight 70 kDa following the similar procedure.

Example 19

Synthesis of Soluble Maleimide Functionalized HA

In a 100 mL flask were taken 200 mg of hyaluronic acid, sodium salt (mol. wt.=500 kDa) and 24 ml of DI water. It was stirred until a clear solution was obtained. To the rapidly stirred HA solution was added 16 mL of ethanol was added in a. 4-(4,6-Dimethoxy-1,3,5-triazin-2-yl)-4-methylmorpholinium chloride (55 mg, 0.2 mmol) in water/ethanol was added along with N-methylmorpholine (20 µl, 0.2 mmol) and the reaction was aged for one hour. An aqueous solution of 1-(2-(2-aminoethoxy)ethyl)-1H-pyrrole-2,5-dione.trifluoroacetate salt (60 mg, 0.2 mmol) was added. The reaction was left over night. The pH is adjusted to be slightly acidic and pre-washed Amberlite® CG-120, $Na^+$ form (≥15 ml) was added to the reaction mixture and stirred for 20 minutes. The resin was filtered off and washed with water. To the filtrate was again added pre-washed Amberlite® CG-120, $Na^+$ form (≥15 ml) and the same procedure as above was followed. The whole cycle was repeated once more. The solution was diluted with water to form an aqueous solution containing <20% ethanol. The solution was spin-filtered using four Macrosep® centrifugal devices from PALL, 30K molecular weight cutoff (5000 rpm, 15 minutes spin time. The membrane is cleared each time by gently stroking a spatula over it and vigorously shaking the sealed devise). The retentate was washed several times with deionized water (>200 ml). The resulting modified HA concentrates were combined and lyophilized. Recovery is between 50-75%. Degree of modification 20% according to NMR.

Example 20

Estimation of Maleimide Content in Hyaluronic Acid Hydrogels

Estimation of maleimide groups incorporated to HA hydrogels was performed by a colorimetric analysis method. 5-Thio 2-nitrobenzoic acid was prepared by the reduction of 5,5'-dithiobis-(2-nitrobenzoic acid) with Tris-(2-carboxyethyl) phosphine hydrochloride (TCEP) in PBS buffer at pH 7.5. A 20 mol % excess of 5,5'-dithiobis-(2-nitrobenzoic acid) was used to prevent side reactions with TCEP. A predetermined amount of maleimide functionalized hydrogel suspended in 20 mM Succinate buffered saline (SBS) at pH 3.5. Above 5-Thio 2-nitrobenzoic acid solution was added to the hydrogel suspension and the reaction mixture was vortex mixed (2×10 seconds) and was subsequently stirred gently at 25° C. for 45 min. The suspension was subsequently centrifuged at 25° C. for 10 min and an aliquot of the supernatant taken. The absorbance of the supernatant was measured at 412 nm. The concentration 5-thio 2-nitrobenzoic acid in the solution was estimated using a calibration curve. Maleimide concentration in the hydrogels is equivalent to the moles of thiol reacted, which is calculated from the difference between the amount 5-thio 2-nitrobenzoic acid added and that present in the supernatant.

Example 21

Synthesis of Near Infrared Dye (IRDye800CW) Conjugated HA Hydrogel

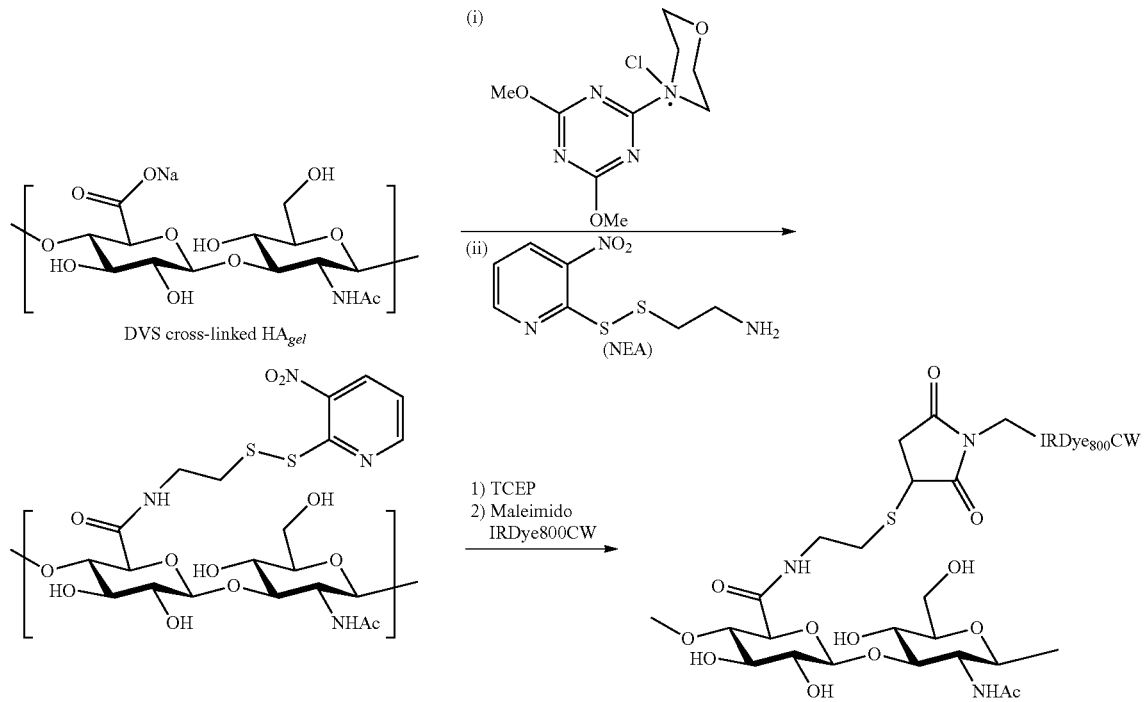

Example 21 a. Synthesis 3-nitro-2-(2'-amino-ethyldisulfanyl)pyridine Hydrochloride (NEA) Conjugated Divinyl Sulfone Cross-Linked Hyaluronic Acid A suspension containing 5.1 g (23 mg/g of water) of divinylsulfone cross-linked hyaluronic acid hydrogel (example 5) and 20 mL of sterile water was gentle stirred at 25° C. for 15 min. To this suspension was added ethanol (20 mL) and the resulting reaction mixture was stirred 25° C. for one hr. To this suspension was added 0.081 g of DMT-MM dissolved in 5 mL of ethanol. The vial containing DMT-MM solution was rinsed with 2.5 mL of ethanol and the washing was added to the suspension. The reaction mixture was stirred at 25° C. for 1 hr. followed by addition of 0.017 g of NEA. After stirring the reaction mixture for 22h at 25° C., 2 mL of brine was added the gel. The solvent was removed by centrifugation was the residue was washed by multiple ethanol treatment (4×10 mL, 1×5 mL). The suspension was centrifuged at 2500 rpm for 5 min followed by at 5000 rpm for 5 min (the temperature of the centrifuge was maintained at 5° C.). The supernatant was decanted and residue was allowed equilibrate for 20 min in sterile water (20 mL). Subsequently, it was subjected to two ethanol treatment (4×10 mL). The slurry was allowed to settle for 30 min and the supernatant decanted. The ethanol treatment process was repeated one more time and the wet gel was stored at 2° C. until next step.

Example 21b. Synthesis of NIR Dye Conjugated HA Hydrogel

Under aseptic condition, 0.224 g NEA modified hyaluronic acid (example 15a) and 13 mL of sterile water were taken in a 50 mL sterile reaction vial and the mixture was allowed to shake gently for 15 min at 25° C. To this suspension was added 20 mL of ethanol and the suspension was stirred for 1 hr. at 25° C. Subsequently, 14 mg of TCEP was added to the suspension and the reaction mixture was stirred for 16 hr. at 25° C. At the end of the reaction, 2 mL of brine was added to the reaction mixture. Subsequently, the gel was subjected to 5 cycles of ethanol treatment (5 mL) and centrifugation (5000 rpm, 5 min., 5° C.). After removal of the supernatant, the residue was treated with 10 mL of in 0.9% sterile saline followed 5 round of ethanol (5 mL) treatment and centrifugation as mentioned above. The residue was suspended in 10 mL of sterile 0.9% saline. To this suspension was added 1.8 mg of maleimide functionalized IRDye800CW dissolved in sterile 0.9% saline (3 mL) using a sterile dehydrogenating filter. The filter was rinsed with 5 mL of ethanol and ethanol/saline 1:1 (2×5 mL) and the washing were added to the reaction mixture. The reaction vessel was agitated gently in dark for 2 hr. at 25° C. and was kept at 2° C. for 66h. Subsequently 11.5 mg of N-methylmaleimide dissolved in 3 mL of ethanol was added to the reaction mixture and the suspension it was shaken gently for additional 3 hr at 25° C. At the end of the reaction, the suspension was centrifuged (5000 rpm, 5° C., 2×15 min) and 20 mL of supernatant was removed. The remaining suspension was precipitated from ethanol (5×5 mL) and further centrifuged (5000 rpm, 5° C., 5 min) and the supernatant was decanted. 10 mL of 0.9% sterile saline was added to the residue, followed by 5 mL of ethanol. The suspension was centrifuged (5000 rpm, 5 min, 5° C.) and supernatant was decanted. The ethanol treatment and centrifugation process was repeated four more time. The residue was treated with 10 mL of sterile 0.9% saline and stored at 2° C. under dark by wrapping the vial with an aluminum foil.

Conjugation of Linker Thio Peptides to Maleimide Functionalized HA Hydrogel

Example 22

General procedure for the thiol terminated trace-linker bearing peptides to maleimide functionalized HA hydrogels.

In a sterile and depyrogenated reactor with medium porosity frit or filter was taken appropriate amount of the maleimide modified HA hydrogel (example 3). Subsequently, appropriate amount of sterile filtered 20 mMol SB buffer (containing 15% v/v propylene glycol and 0.01% w/v Tween 20, pH 3.8) was added to the reaction such that the concentration of the resulting suspension is ~1% w/w. The suspension was allowed to mix for 30-90 minutes with gentle shaking. At the end of this time, appropriate amount of thiol terminated trace-linker bearing peptide dissolved in sterile filtered 20 mMol SB buffer (containing 15% v/v propylene glycol and 0.01% w/v Tween 20, pH 3.8) was added to the reactor and the resulting reaction mixture was allowed to shake gently at ambient temperature for 1.5-24 hours. At the end of the reaction, the supernatant was removed by filtration using a slight excess pressure of nitrogen or by centrifugation of the suspension. The residue was treated with sterile filtered 20 mM SBS buffer (containing 15% v/v propylene glycol and 0.01% w/v Tween 20, pH 3.0) to prepare a suspension 0.7 w/v %, shaken for 3 minutes, centrifuged and the supernatant was removed by decantation. This process was repeated five times. The residue was treated with 10 mM solution of 1-Hydroxy-2-mercaptoethane dissolved in sterile filtered 20 mM SBS buffer (containing 15% v/v propylene glycol and 0.01% w/v Tween 20, pH 3.0) to prepare a ~1 wt % suspension and was allowed to stir gently for 30 minutes with gentle shaking/mixing. The solvent was removed by centrifugation followed by decantation as mentioned above. This process of 1-Hydroxy-2-mercaptoethane treatment was repeated four times. The residue was suspended in sterile filtered 20 mM SBS buffer (containing 15% v/v propylene glycol and 0.01% w/v Tween 20, pH 3.0) to prepare a suspension of ~0.5 wt % concentration and mixed for 3 minutes followed by removal of the by centrifugation and decantation. The resulting residue was suspended in 20 mM SBS buffer (containing 15% v/v propylene glycol and 0.01% w/v Tween 20, pH 6.5) to prepare a 0.7 wt % suspension and stirred for 20 minutes and filtered. After repeating this process one more time, the residue was in 20 mM SBS buffer (containing 15% v/v propylene glycol and 0.01% w/v Tween 20, pH 4.5) to prepare a 0.5 wt. % suspension, stirred for 15 minutes, and filtered. This process was repeated once. The residue was suspended in sterile water (pH 4.5), stirred for 5 minutes, and filtered. The process was repeated five times and. The residue was aseptically filtered using a sterile membrane filter and lyophilized to dryness.

Table 3 summarizes results on the syntheses of various HA hydrogel conjugates of dual agonist peptides obtained by varying reaction conditions and nature of traceless linker.

| Amount of maleimide modified HA hydrogel (mg) | Maleimide content in hydrogel (mol %) | Linker type | Amount of Peptide linker used (mg) | Yield of hydrogel-peptide conjugate (mg) | Peptide loading (wt. %) | Peptide loading (mol %) |
|---|---|---|---|---|---|---|
| 36 | 3.4 | Asn | 2.1 | 20 | 4 | 0.41 |
| 35 | 4.9 | Asn | 2.4 | 31 | 2.4 | 0.24 |
| 297 | 10.8 | Asn | 30.6 | 228 | 4 | 0.41 |
| 57.5 | 3.8 | Asn | 15 | 66.3 | 11.1 | 1.2 |
| 54 | 3.8 | Asn | 23 | 77.8 | 15.9 | 2.18 |
| 48 | 5.7 | Asn | 30 | 60.8 | 21.0 | 2.6 |
| 73.2 | 5.2 | Asn | 15.8 | 51.6 | 11 | 1.2 |
| 137 | N.D. | Asn | 62.5 | 150 | 21.7 | 2.69 |
| 90 | 9.8 | Aib | 13.3 | 78 | 6.5 | 0.69 |
| 50 | 8.8 | D-Ala | 3.7 | 49.3 | N.D. | N.D. |
| 41 | 6.2 | D-Ala | 9.2 | 52 | N.D. | N.D. |

TABLE 3b

The following conjugates were prepared as described in examples 14 to 22

| Amount of crosslinked HA hydrogel (g) | HA content in gel (%) | Maleimide loading in hydrogel after activation (mol %) | Linker type | Amount of Peptide linker used (mg) | Yield of lyophilized hydrogel-peptide conjugate (g) | Peptide content by NMR (mol %) |
|---|---|---|---|---|---|---|
| 200 | 2.3 | 12.1 | Aib | 508 | 6.4 | N.D. |
| 40 | 2.3 | 14.8 | Aib | 102 | 1.2 | N.D. |
| 40 | 2.3 | 9.6 | Aib | 108 | 0.84 | N.D. |
| 40 | 2.3 | 13.6 | Aib | 203 | 0.89 | 6.5 |
| 40 | 2.3 | 11.0 | Aib | 102 | 0.82 | 3.6 |
| 40 | 2.3 | 12.5 | Aib | 104 | 0.71 | 5.9 |
| 40 | 2.3 | 16.8 | Aib | 108 | 0.49 | 9.0 |
| 40 | 2.3 | 8.0 | Aib | 102 | 1.2 | N.D. |
| 40 | 2.3 | 13.5 | Aib | 102 | 1.1 | 4.4 |
| 30 | 2.6 | 22 | Aib | 127 | 0.67 | 5.3 |
| 30 | 2.6 | 18.2 | Aib | 201 | 0.45 | 6.5 |

Conjugation of linker 7 containing thiol functionalized Exendin-4 Seq ID No. 26 with maleimide functionalized hyaluronic acid.

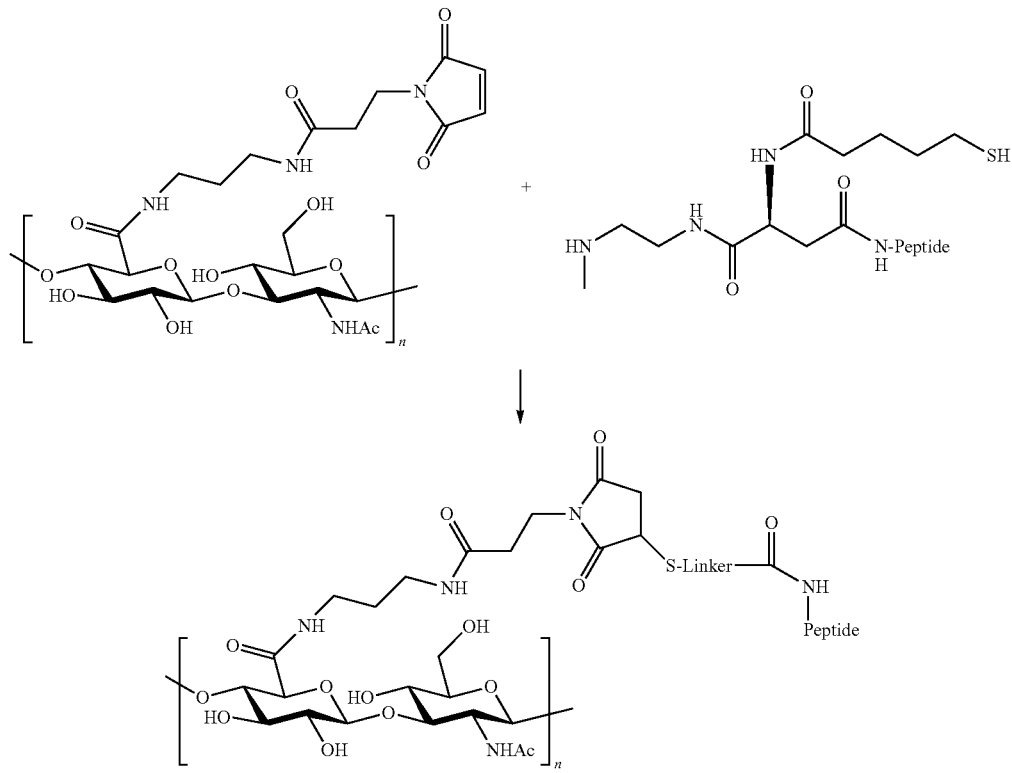

To 53 mg of 3-(3-maleimidopropyl) aminopropane modified DVS-HA hydrogel (example 15) was added 7 mL of the 20 mM SBS containing, 0.01 wt % Tween® 20, propylene glycol (15% v/v). The pH of buffer is 3.8. The suspension was gently agitated at 25° C. for 90 min. To this suspension was added 2.1 mg of thiol functionalized Exendin-4 Seq ID 26 with the linker of example 7 dissolved in 1 ml of above buffer. The peptide vial was rinsed with buffer (2×0.5 mL) and the washing was added to suspension. The reaction mixture was gently agitated at 25° C. for 18h. The suspension was subsequently centrifuged at 1750 rpm for 2 min and the supernatant was carefully decanted. The hydrogel was suspended in 10 mL of 20 mM SBS buffer containing 0.01 wt % Tween® 20, propylene glycol 15% v/v, pH 3, stirred for 2 min, centrifuged at 1750 rpm for 2 min, and the solvent decanted. This process was repeated four more times. The residue was treated with 2 mL of 10 mM 1-Hydroxy-2-mercaptoethane dissolved in 20 mM SBS pH 3 and the reaction was allowed to proceed for 30 min. The reaction mixture was centrifuged at 2000 rpm for 2 min and the solvent decanted. This process was repeated three more times. The residue was suspended in 10 mL of 20 mM SBS containing 0.01 wt % Tween® 20, pH 3, stirred for 2 min, centrifuged at 2000 rpm for 2 min and the solvent decanted. The residue was subsequently suspended in 10 mL of acidified sterile water (pH 3.5) containing 0.01 wt % Tween® 20, stirred for 10 min, centrifuged at 5000 rpm for 5 min and the solvent was decanted. This process was repeated with 8, 7 and 6 mL of the above acidified sterile water. The sample was lyophilized yielding 78 mg of the HA hydrogel conjugated peptide as an off white solid with 4 wt. % loading of peptide in the hydrogel.

Example 23

Conjugation of linker containing thiol functionalized Exendin-4 Seq ID 26 with maleimide functionalized hyaluronic acid.

Reaction and work up were performed using de-oxygenated buffers and under nitrogen atmosphere. To 36 mg of 3-(3-maleimidopropyl) aminopropane modified DVS-HA hydrogel (example 15) was added 6 mL of 20 mM SBS, (containing 0.01 wt % Tween® 20, 10% v/v propylene glycol). The pH of the medium was adjusted 6. The suspension was gently shaken at 25° C. for 30 min. To this suspension was added 2.4 mg of thiol functionalized Exendin-4 Seq ID 26 with linker (example 7) dissolved in 1 ml of the above buffer (pH 6). The peptide vial was rinsed with buffer (2×0.5 mL) and the washing was added to suspension. The reaction mixture was gently shaken at 25° C. for 90 min. The suspension was subsequently centrifuged at 4000 rpm for 2 min and the supernatant was carefully decanted. The hydrogel was suspended in 10 ml of 20 mM SBS at pH 3 (containing 0.01 wt % Tween® 20, and 10 v/v % propylene glycol), mixed for 2 min, centrifuged at 3005G for 2 min, and the solvent decanted. This process was repeated four more times. The residue was treated with 2 mL of 10 mM 1-hydroxy-2-mercaptoethane in 20 mM SBS pH3 for 30 min, centrifuged at 4000 rpm for 2 min and the solvent decanted. This process was repeated three more times. The residue was suspended in 10 mL of 20 mM SBS containing 0.01 wt % Tween® 20 (pH 3), mixed for 2 min, centrifuged at 4000 rpm for 2 min, and the solvent was decanted. This process was repeated four more times. The residue was suspended in acidified (pH 3.5) sterile water containing 0.01 wt % Tween® 20, mixed for 10 min, centrifuged at 5000 rpm for 5 min, and the solvent decanted. This process was repeated using 8, 7 and 6 mL of the above sterile water. The residue was lyophilized to yield 31 mg HA conjugated peptide as an off white solid with 2.4 wt % peptide loading in the hydrogel.

Example 24

Procedure for Estimation of Peptide Loading in the Hydrogel-Peptide Conjugates

A predetermined amount HA hydrogel-peptide conjugate was suspended in CHES buffer (pH9.5) and the suspension was allowed to gently stir at 70° C. The suspension was centrifuged and the aliquot was analyzed for peptide content by HPLC method. The HPLC method comprises of using q C-18 Kinetics column (inner diameter=4.6 mm and length=100 mm, particle size 2.6 µm, Phenomenex) using Agilent 1100 LC. The composition of mobile phase A is 90% water/10% Acetonitrile/0.1% Trifluoroacetic acid (TFA) and the mobile phase B is 10% Acetonitrile/90% water/0.09% TFA. The gradient is from mobile phase 25% B to 55% B in 8 minutes. The flow rate was kept at 1 mL/min. Pure peptides were used as standards to quantify the released peptide from the hydrogel.

Example 25

Determination of In Vivo Residence Time of the HA Hydrogel

The residence time of hydrogels in vivo in the subcutaneous space were investigated by magnetic resonance (MR) imaging. The intensity of water proton contrast inside the hydrogel was used to assess the hydrogels residence time in vivo. For this purpose, CAnN.Cg-Foxn1 nu/Crl mice were used as the animals. The hydrogel was injected using a 31 G needle by following all approved animal care protocols. The MR image of the injection site was taken regularly over a period of time. In one group, the hydrogel was injected and in the other group, a suspension of containing 1:1 (w/w) mixture hydrogel and 800,000 Da soluble HA was used. In the case of pure hydrogel, the gel was evident for 3 weeks with slow loss in intensity (FIG. 2). On the other hand, for the mixture containing soluble HA, the MR signal, which was intense on day 1, has significantly reduced on day 4 (2). This suggests that to improve the residence time of the polymer carrier, it needs to be crosslinked to achieve very high molecular weight.

FIG. 2a. MR of Image of the HA hydrogel at the injection site as a function of time.

FIG. 2b. MR of Image of the polymer suspension containing 1:1 (w/w) HA hydrogel-800 kDa soluble HA at the injection site as a function of time.

Example 26

Release Kinetics In Vitro

An aliquot of GLP-1/Glucagon agonist linker hydrogel 8 (0.5 mg GLP-1/Glucagon agonist) was transferred into a syringe equipped with a filter frit and washed 5 times with pH 7.4 phosphate buffer (60 mM, 3 mM EDTA, 0.01% Tween-20). The hydrogel was suspended in the same buffer and incubated at 37° C. At defined time points (after 1-7 days incubation time each) the supernatant was exchanged and liberated GLP-1/Glucagon agonist was quantified by RP-HPLC at 215 nm. UV-signals correlating to liberated GLP-1/Glucagon agonist were integrated and plotted against incubation time. Curve-fitting software was applied to estimate the corresponding halftime of release.

FIG. 3. In vitro release kinetics of Exendin-4 Seq ID 26 dual agonist with linker from the HA hydrogel (example 23). The half-life is ~5 days.

Example 27

In Vitro Cellular Assays for GLP-1 Receptor, Glucagon Receptor and GIP Receptor Efficacy Agonism of peptides for the receptors was determined by functional assays measuring cAMP response of HEK-293 cell lines stably expressing human GIP, GLP-1 or glucagon receptor.

cAMP content of cells was determined using a kit from Cisbio Corp. (cat. no. 62AM4PEC) based on HTRF (Homogenous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 µl-aliquots dispensed into the wells of 96-well plates. For measurement, 25 µl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/620 nm. In vitro potency of agonists was quantified by determining the concentrations that caused 50% activation of maximal response (EC50).

Example 28

Glucose Lowering in Female Diabetic Dbdb-Mice

Female diabetic dbdb-mice (BKS.CG-m+/+Lepr(db)/J) 24-27 weeks of age at study start were used. Mice arrived in the age of 10-13 weeks were habituated to feeding and housing conditions for at least 1 week, then used in a first study and after a washout period of at least 2 weeks finally reused for the present study. 19 days prior to study start, individual HbA1c values were determined to stratify and thereafter allocate the animals into 4 groups with an N=8 per group to provide groups with as equally as possible mean HbA1c values. Animals had access to food and water ad libitum throughout the entire study period. On the first day of the study blood glucose from tail tip incision was determined just before and 4 hours after single subcutaneous treatment (08:00-09:00 am) with either vehicle (sterile succinate buffer) or the HA-conjugate of GLP-1/Glucagon agonist Seq. ID 26 of example 23 in the doses 50, 100 and 200 nmol/kg diluted in vehicle. Thereafter daily blood glucose measurements were performed for the next 16 days all at a similar day time (08:00-09:00 am) with the exception of days 11 and 12 (weekend). In addition food intake and water consumption was monitored on a daily basis. Glucose data were analyzed by two-way-ANOVA on repeated measurements, followed by Dunnett's post-hoc test with a significance level of p<0.05. Glucose AUC analysis was done using a one-way-ANOVA followed by Dunnett's post-hoc test with a significance level of p<0.05.

FIG. 4 shows the blood glucose concentration relative to the baseline versus time after one injection at various doses of HA-GLP-1/Glucagon agonist conjugate with Seq. ID 26.

Example 28b Glucose Lowering Effects in Female Diabetic dbdb-Mice

Female, obese diabetic db/db-mice (BKS.CG-m+/+Lepr (db)/J and healthy, lean controls (BKS.Cg-m+/+Lepr(db)/J) arrived at the age of 10-11 weeks and were habituated to feeding and vivarium conditions. At the age of 12-13 weeks individual HbA1c values were determined to stratify and allocate animals into different groups with an N=8 per group. Goal wes to provide groups with as equally as possible mean HbA1c values. At the age of 13-14 weeks 2 groups of db/db mice received a s.c. 100 nmol/kg body mass single dose of a conjugate with Seq. ID 26 of either soluble or crosslinked HA. At the same time and a second time on day 7 a third group of db/db mice and the healthy lean references received a s.c. injection of succinate buffer and soluble HA in a 1:1 ratio. In all groups a total volume of 5 ml/kg body mass was injected. Morning-fed blood glucose concentrations were determined just before (between 08:00-09:00 am) and four hours after treatment and thereafter daily between 08:00-09:00 am. Blood was collected from tail tip incisions and concentrations determined via a handheld glucometer (Accu Check). Throughout the entire study period animals had access to food and water ad libitum.

FIG. 4b shows the blood glucose concentration relative to the baseline versus time after one injection of cross-linked and soluble HA-GLP-1/Glucagon agonist conjugate with Seq. ID 26.

Example 28c

Glucose Lowering Effects in Female Diabetic Db/Db-Mice

After arrival female, obese diabetic db/db-mice (BKS.CG-m+/+Lepr(db)/J) were habituated to feeding and vivarium conditions and were 12 weeks old at study start. Individual HbA1c values were determined on day 10 of the predose phase to stratify and allocate animals into different groups with an N=8 per group. Goal was to provide groups with as equally as possible mean HbA1c values. On day 1 of the dosing phase db/db mice received a s.c., single dose of 12.75 mg/kg body mass of either conjugate with Seq ID 45, 46, 48 and 49. Db/db animals of the Vehicle group received a s.c. PBS injection. In all groups a total volume of 10 ml/kg body mass was injected. Morning-fed blood glucose concentrations were determined just before (between 08:00-09:00 am) and four hours after treatment on day 1 of the dosing phase and thereafter daily between 08:00-09:00 am. Blood was collected from tail tip incisions and concentrations determined via a handheld glucometer (Accu Check). Throughout the entire study period animals had access to food and water ad libitum.

Example 29

Injectability Study

A suspension of 3.75% (mg/mL) HA-peptide conjugate was prepared by dispersing appropriate amount of the peptide conjugate in 20 mM succinate buffered saline (SBS) at pH 4.5. In another vial, a 2% (mg/mL) solution of native HA polymer was prepared by dissolving lyophilized HA in 20 mM SBS at pH 4.5. Both the samples were allowed to hydrate for 24 to 48 hours at 2-8° C. The vials were brought to room temperature. After equilibration at room temperature, 1 mL of the peptide-HA hydrogel conjugate suspension and HA was taken in a 3 mL syringe. To this suspension was added 0.25 mL of the soluble HA solution. The resulting suspension was subjected to 20 times of back and forth mixing between two 3 mL syringes. Approximately 220 µl of this suspension was to a 1 ml syringe. To this syringe was attached a 30 g, ½ inch needle. It should be ensured that the needle is not primed with test material. The syringe containing the suspension was loaded into the syringe fixture of the Instron equipment and the crosshead of the Instron was aligned with the plunger of the syringe. The speed of the crosshead was adjusted to achieve target injection rate. The testing was initiated. For each sample, three measurements were performed and result presented is an average of these measurements. The results on injectability force for different peptide-HA hydrogel conjugates are shown in Table 4.

TABLE 4

Effect of HA Modification on Average Injectability Force*

| Compound type | Peptide content in the conjugate | | Average Injectability Force |
|---|---|---|---|
| | (wt. %) | (mol %) | (N) |
| HA Conjugated Seq. ID No. 26, Asn linker | 11.0 | 1.2 | 19.1 ± 0.6 |
| HA Conjugated Seq. ID No. 26, Asn linker | 15.9 | 2.18 | 16.8 ± 1.8 |
| HA Conjugated Seq. ID No. 26, Asn linker | 21.7 | 2.69 | 13.7 ± 1.2 |

*n = 3 per group; injection rate = 12 µl/s

Figure 1A:
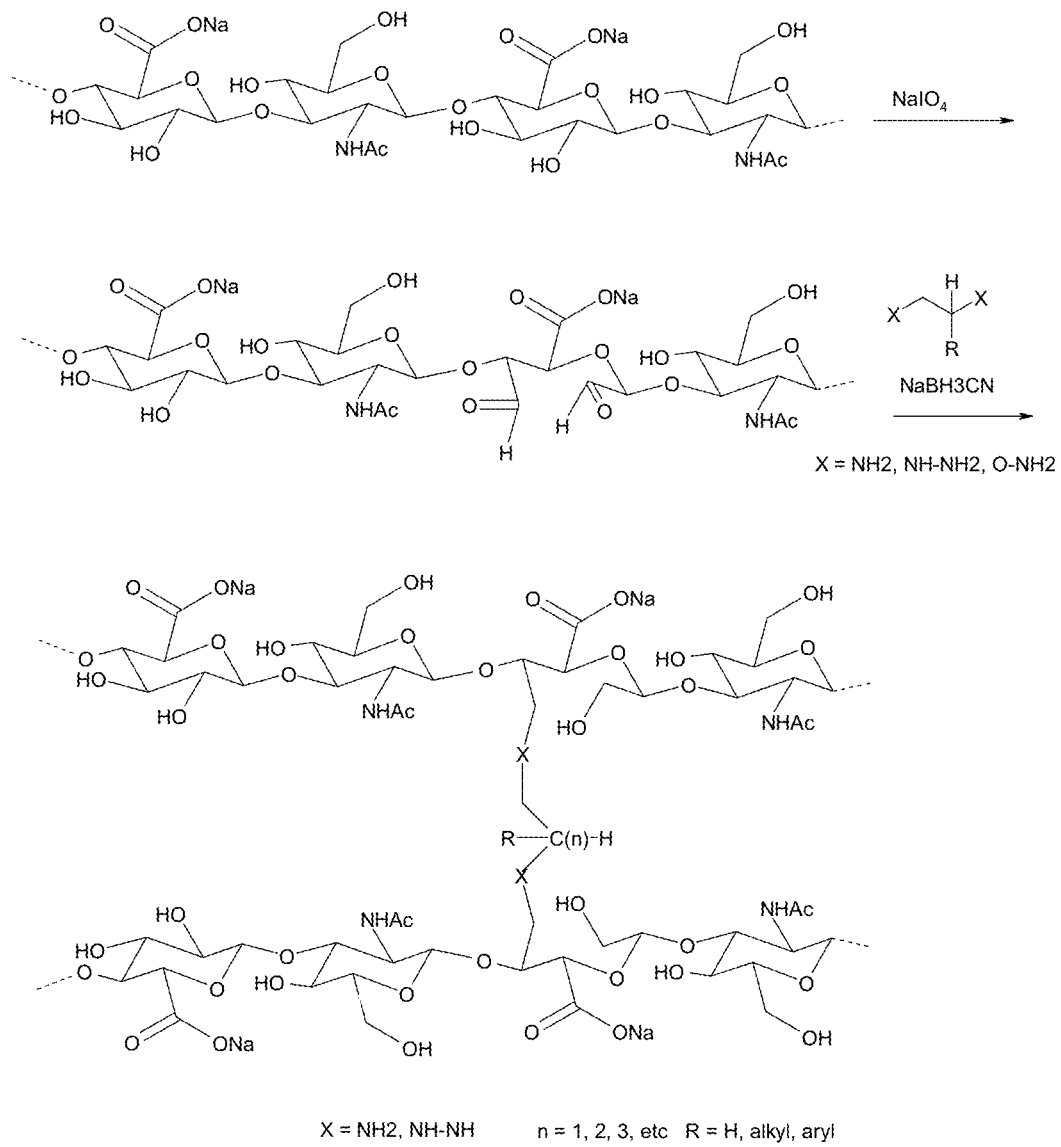
Figure 1A:
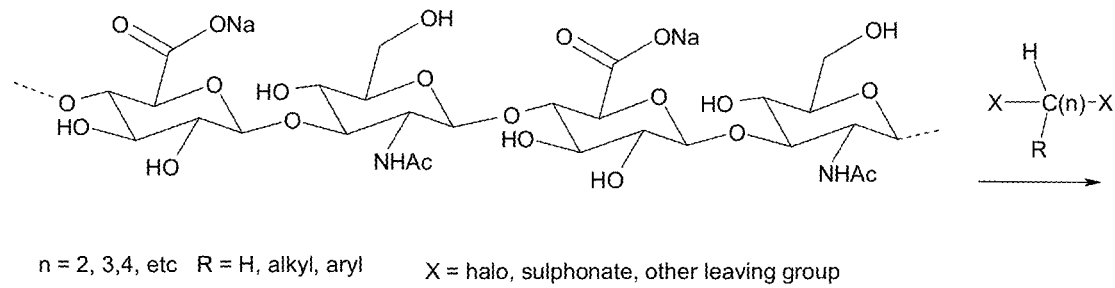
Figure 1A:
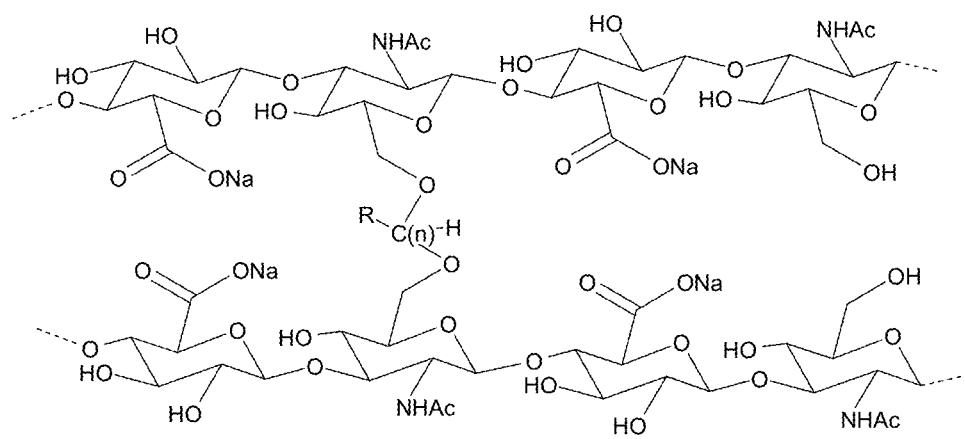
Figure 1A:
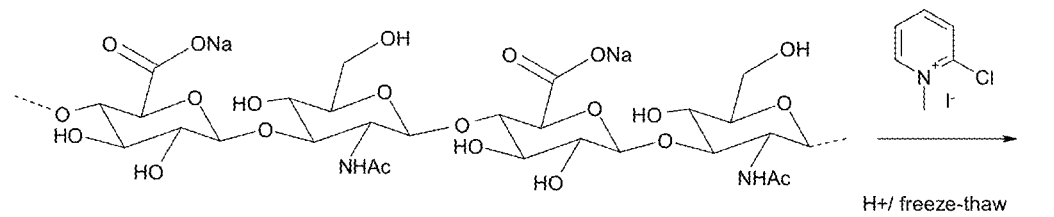
Figure 1A:
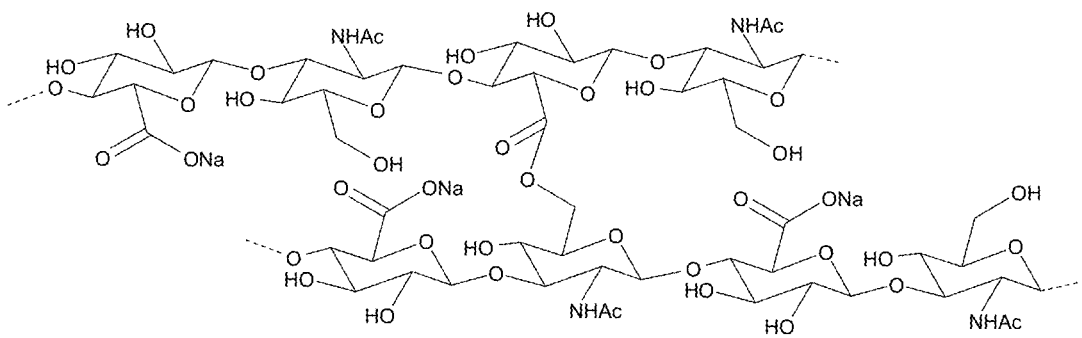
Figure 1B:
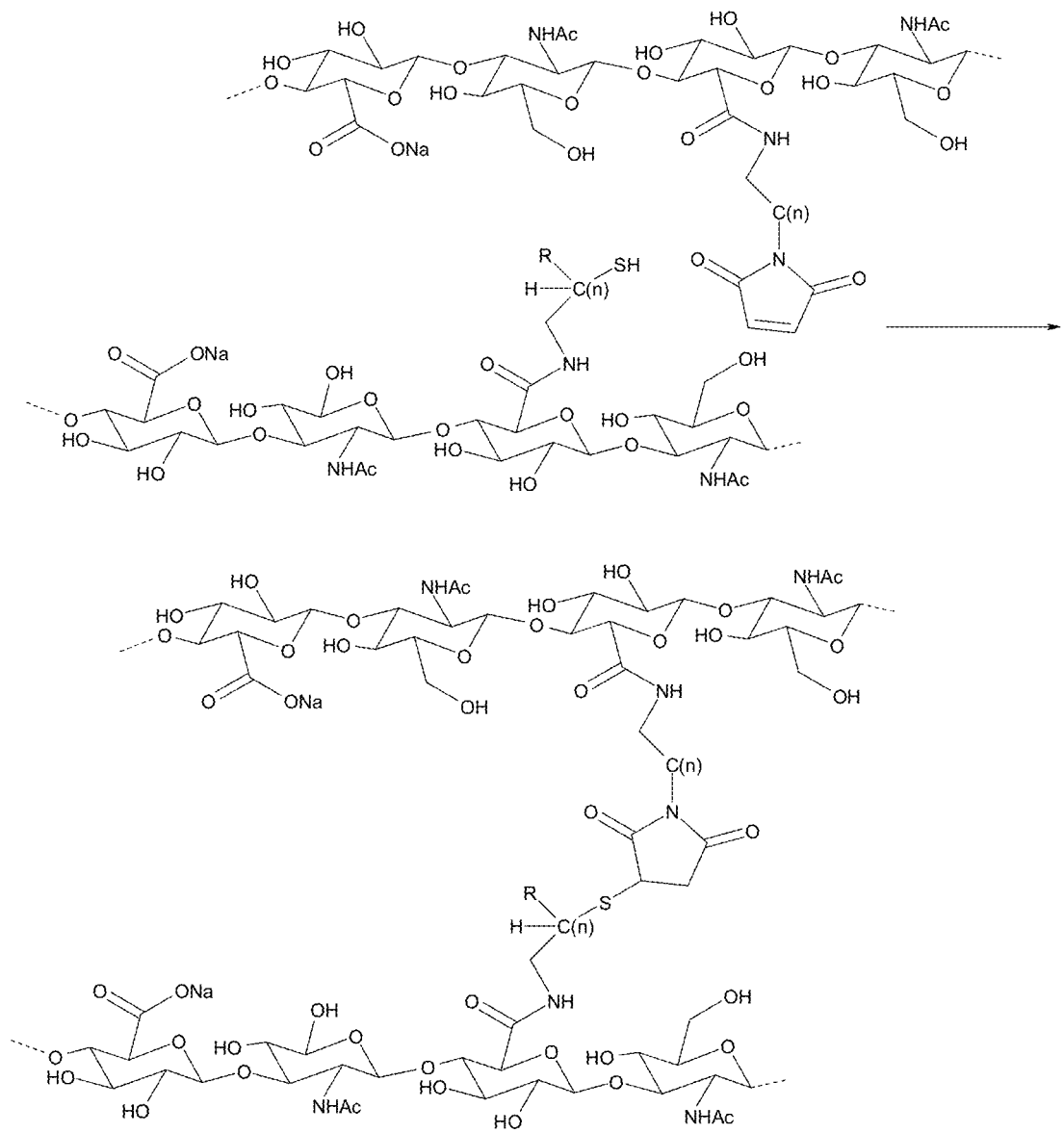
Figure 1B:
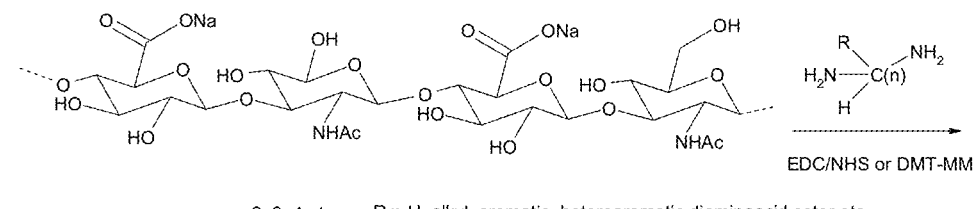
Figure 1B:
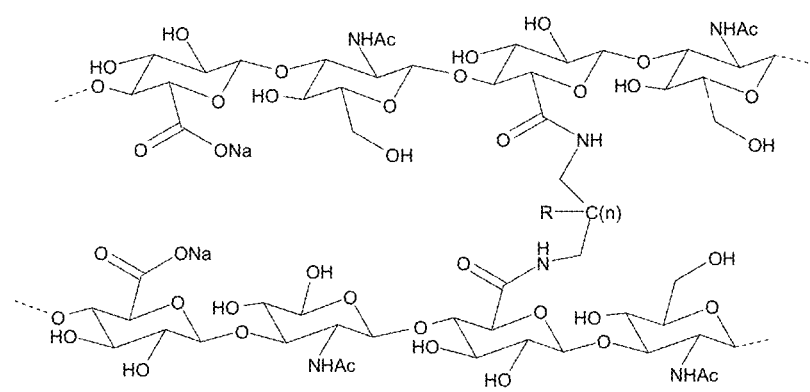
Figure 1B:
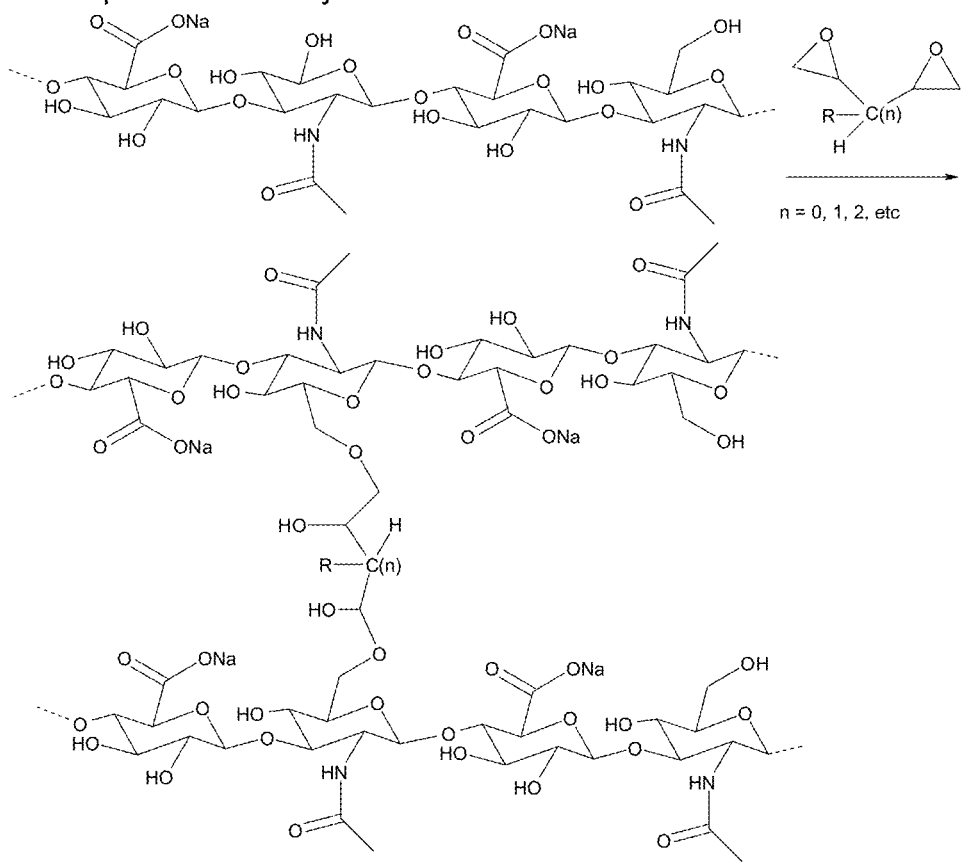
Figure 1C:
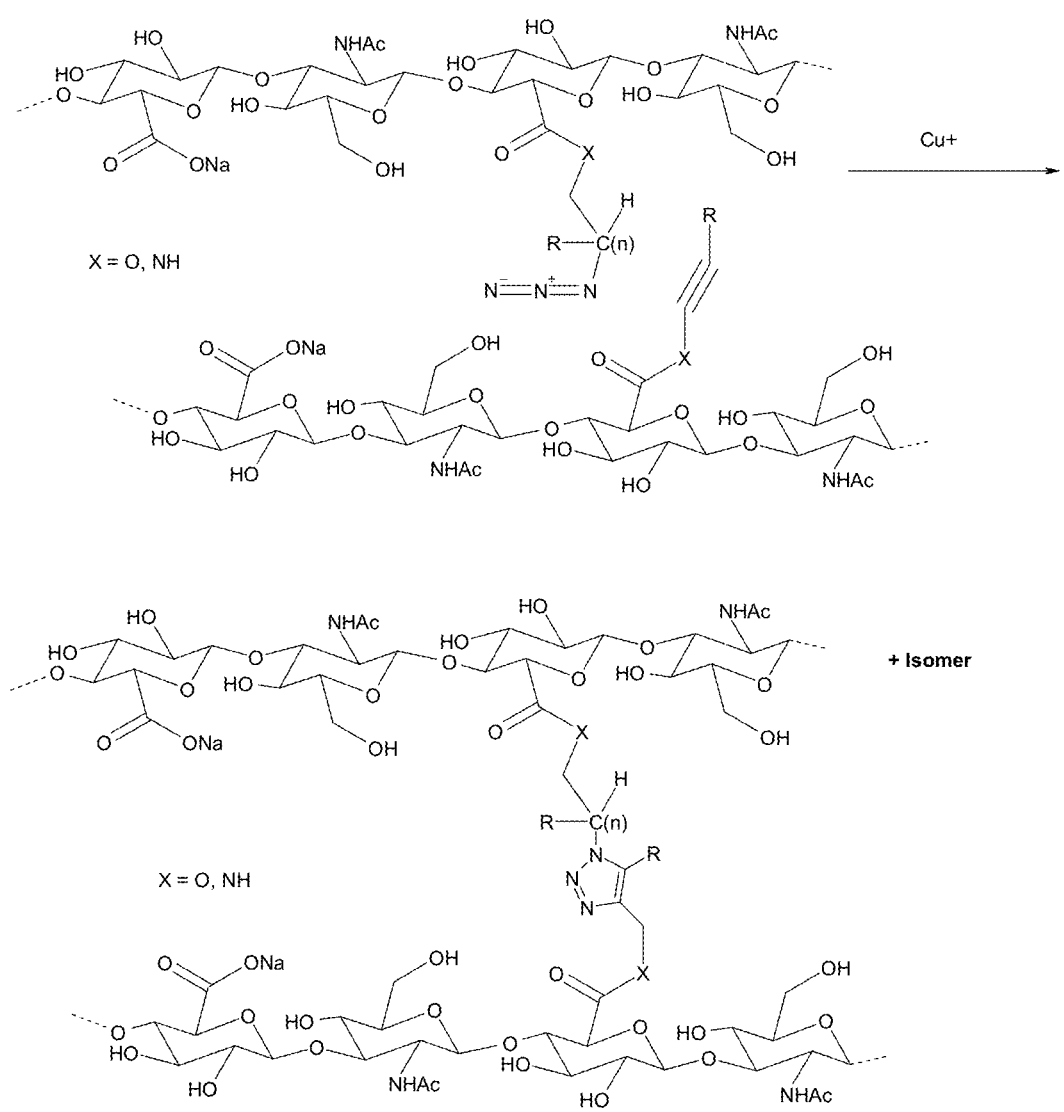
Figure 1C:
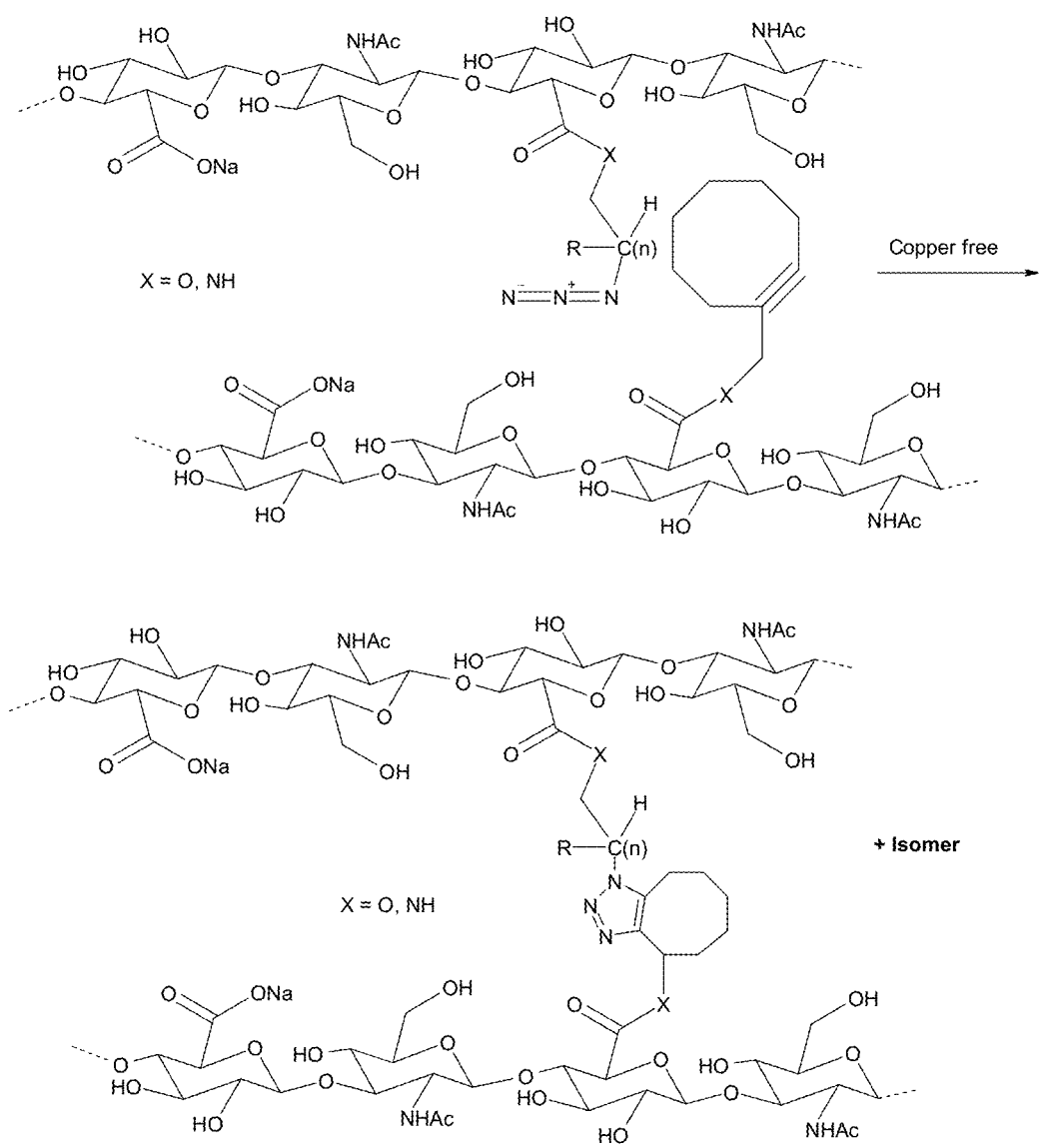
Figure 1C:
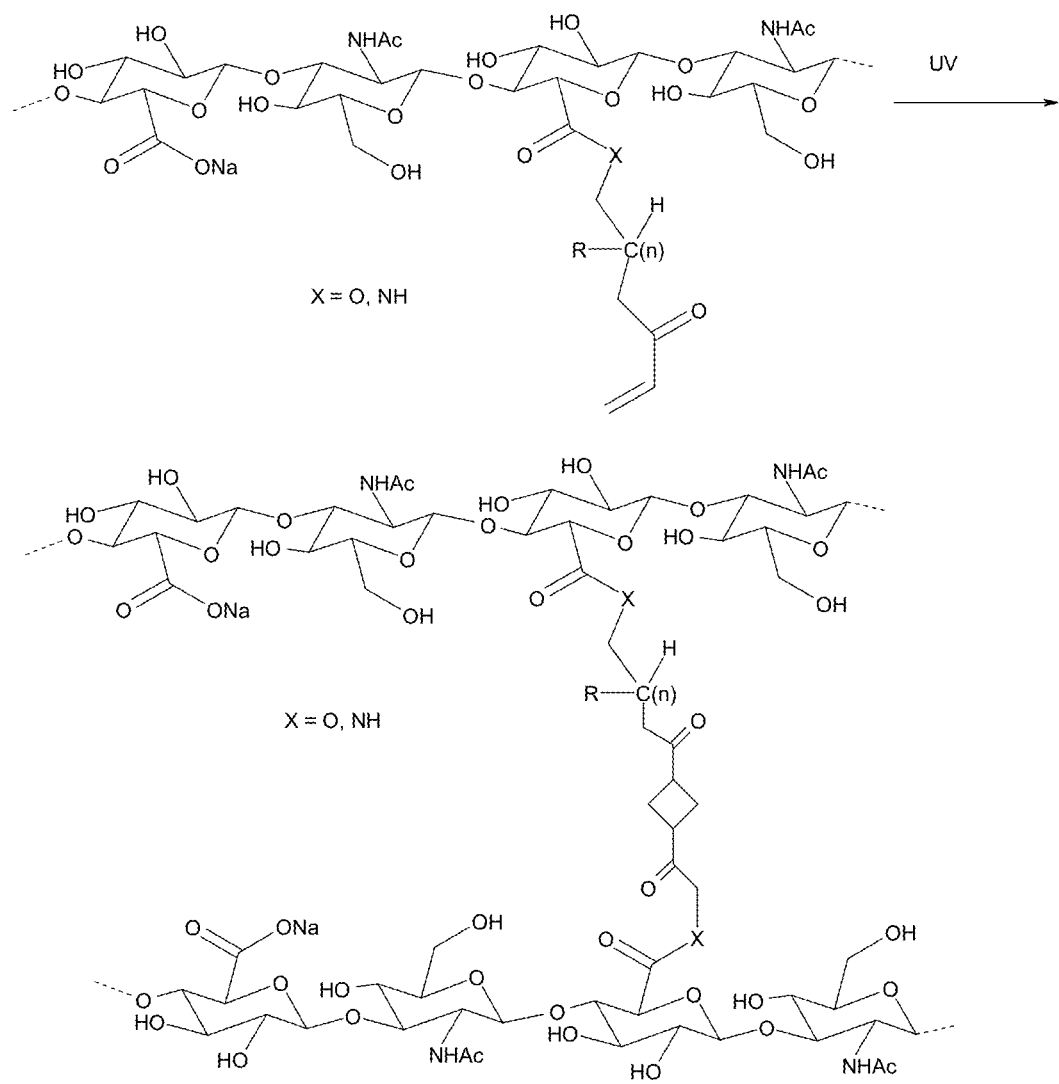
Figure 1C:
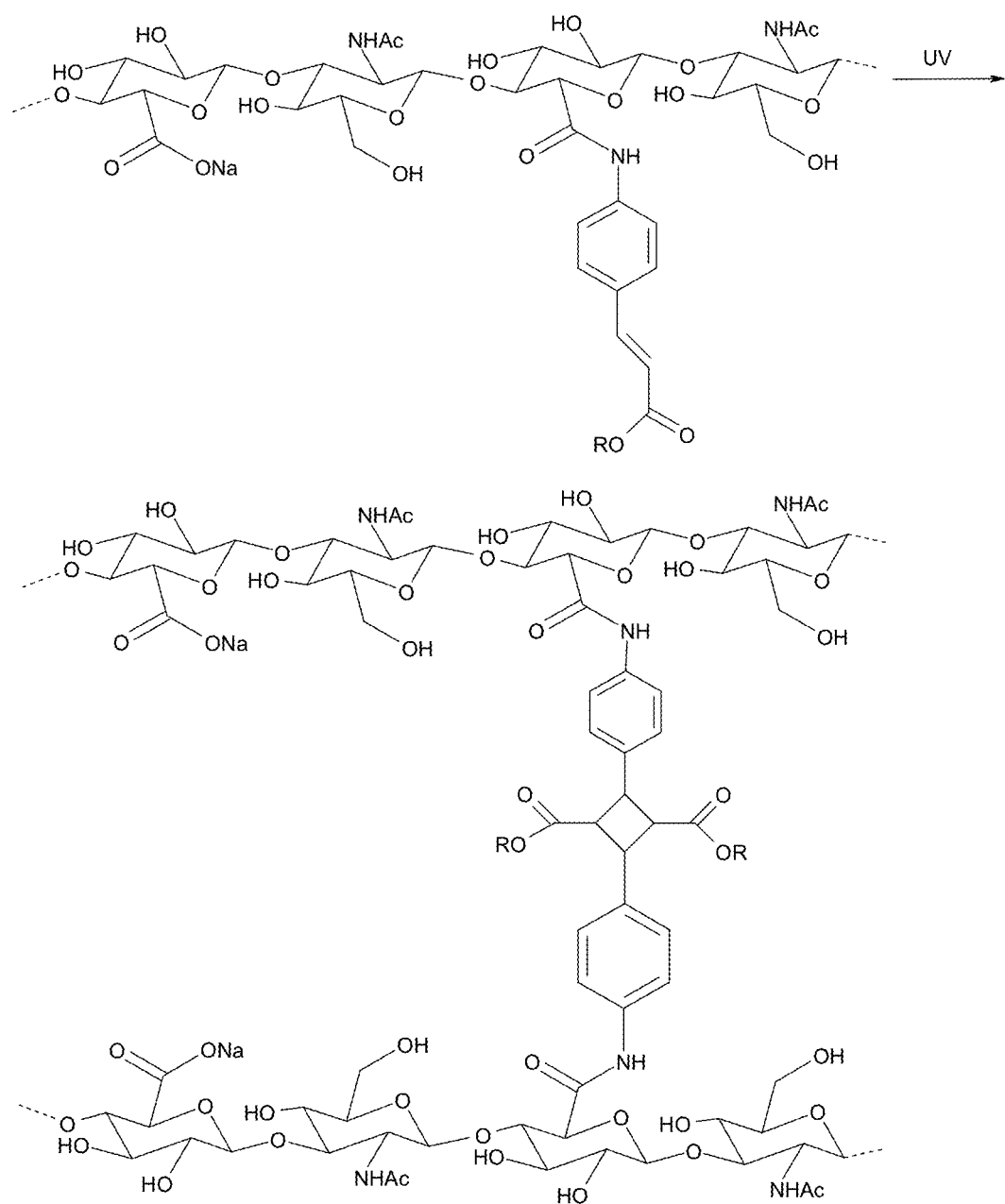
Figure 2A:
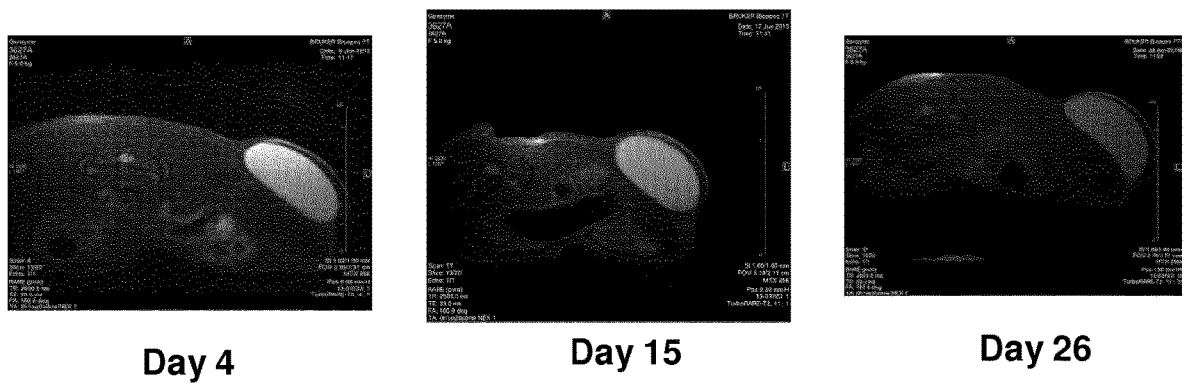
Figure 2B:
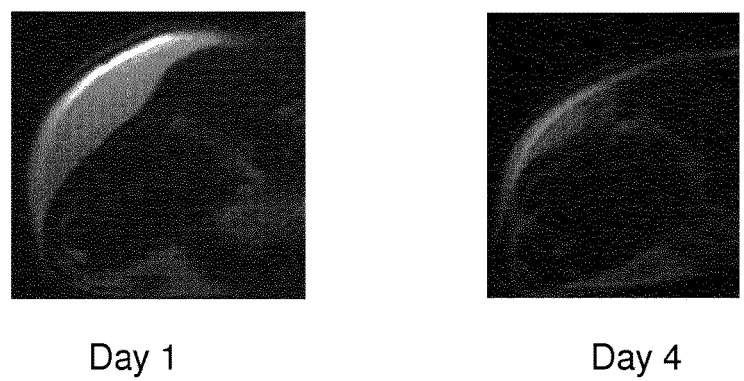
Figure 3:
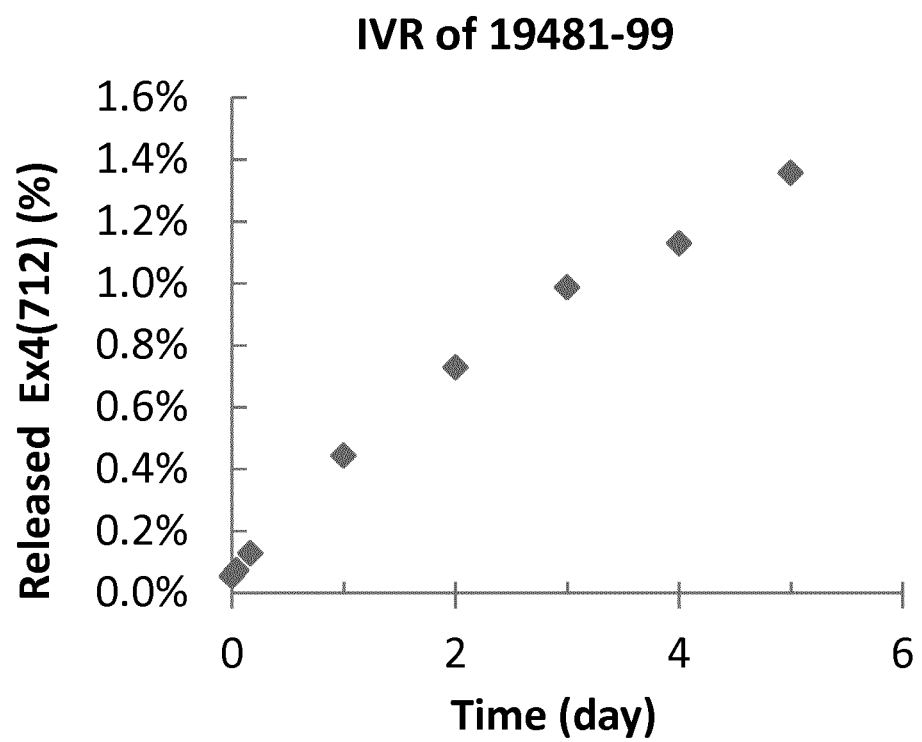
Figure 4:
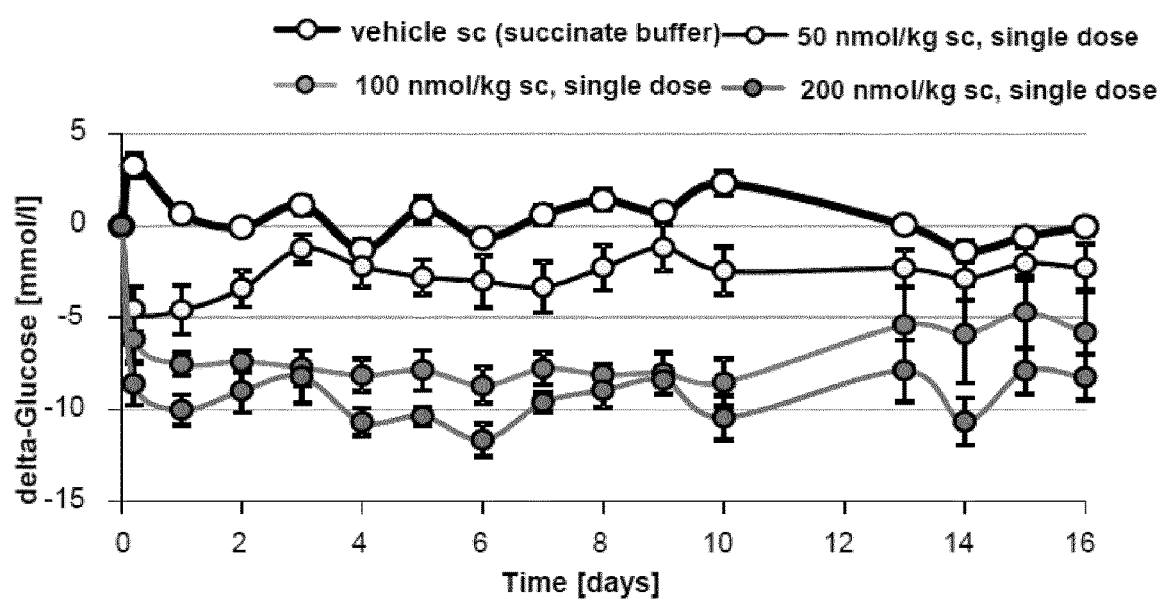
FIG. 4c shows the blood glucose concentration relative to the baseline versus time after one injection at various doses of HA-GLP-1/Glucagon agonist conjugate with Seq. ID 45 (triangles), 46 (squares), 48 (circles).
FIG. 4d shows the blood glucose concentration relative to the baseline versus time after one injection at various doses of HA-GLP-1/Glucagon agonist conjugate with Seq. ID 49 (circles).
Figure 4B:
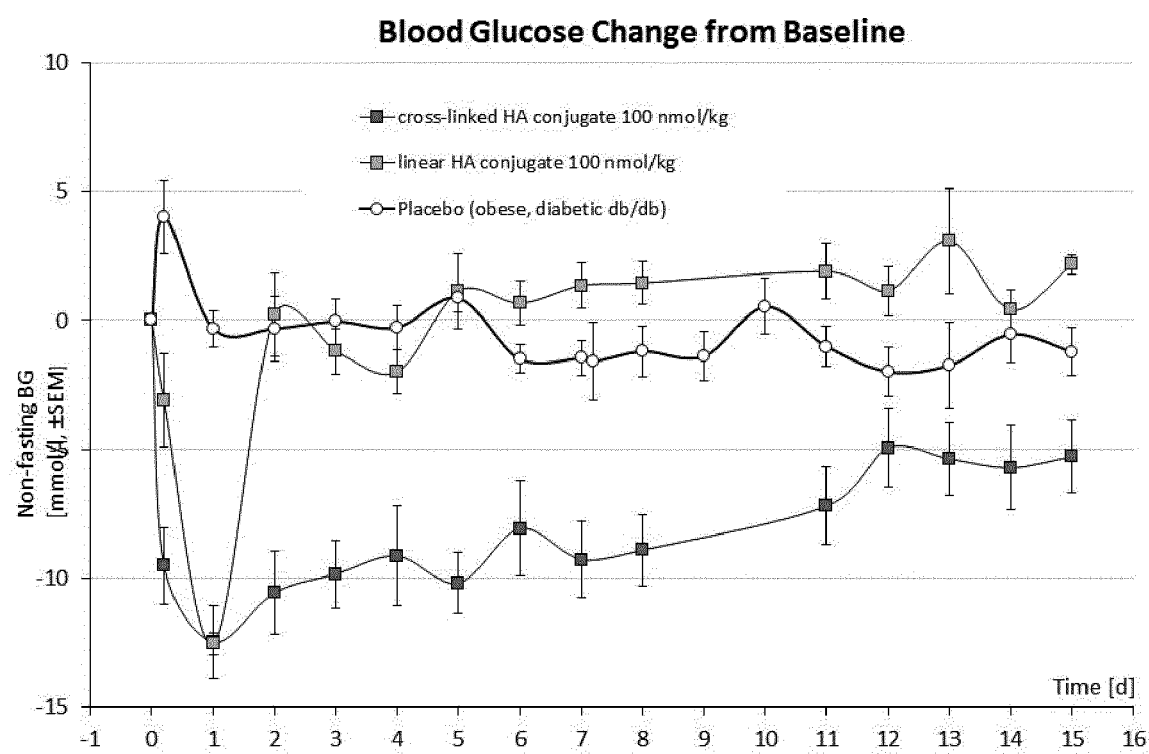
Figure 4C:
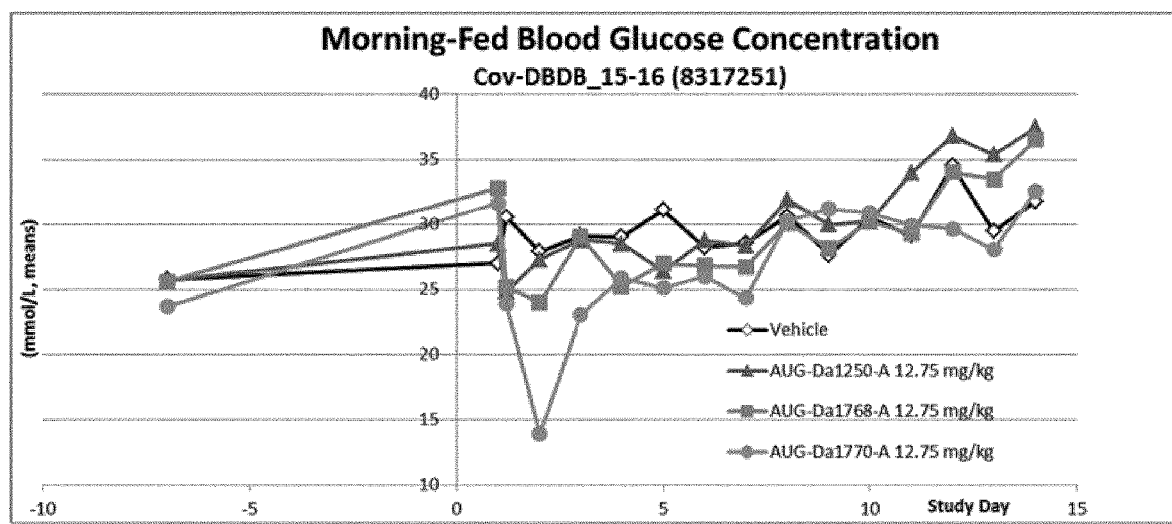
Figure 4D:
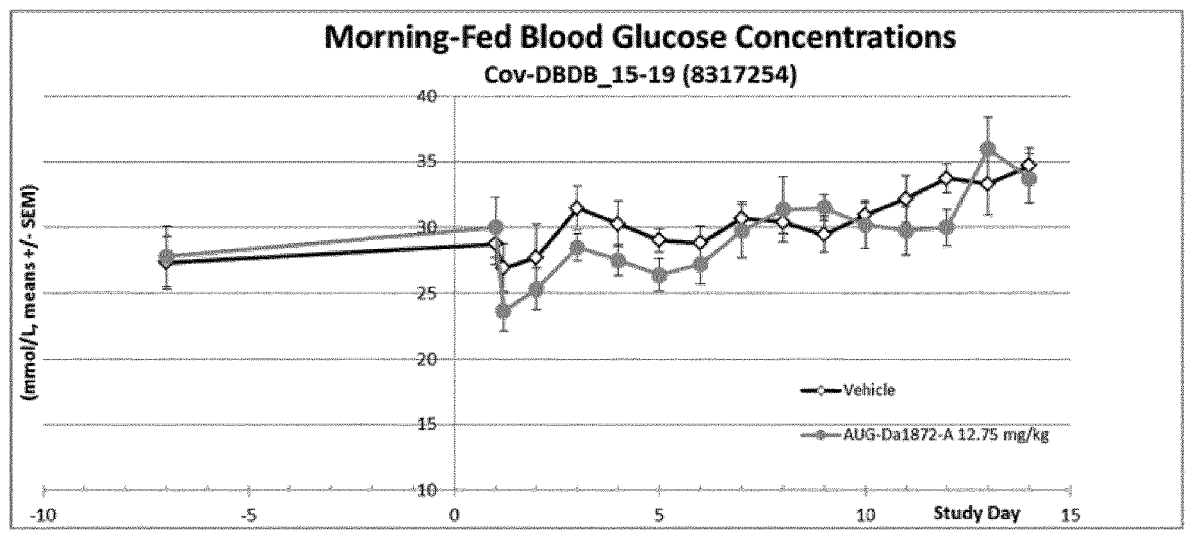
Figure 5:
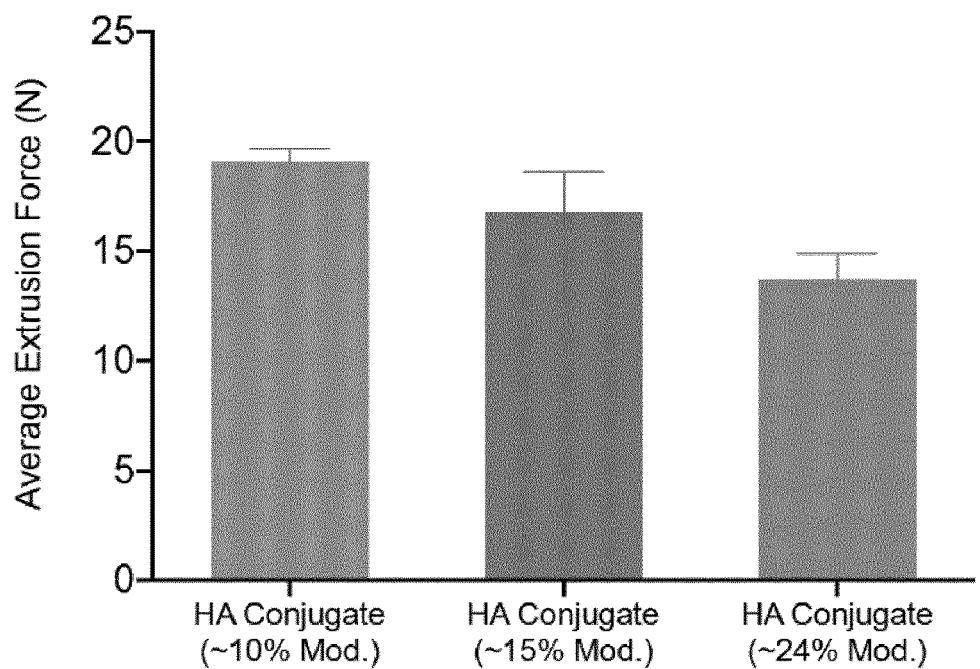

FIG. 5 shows the average extrusion force by pressing the liquid through a 2.5 cm long 30G needle attached to an 1 mL syringe. It is clearly seen that a higher peptide loading on the HA hydrogel leads to lower extrusion forces and therefore enhances injectability.

Example 29b

Injectability Study of HA-Conjugate with Seq. ID No. 45, Aib-Linker

A 1 mL Luer-Lock syringe (BD syringe, inner diameter 4 mm) was filled with approximately 500 μL (460 μL on the syringe scale) of the sample solution and a 29G×12.7 mm needle was attached. The measurement was carried out at the LF Plus dynamometer from Lloyed Instruments. The plunger rod was pushed until a small droplet appeared at the tip of the 29G needle. The syringe was placed in the syringe holder and the dynamometer was moved so that it touches the plunger rod.

The measurement setting was: an abortion force of 50 N and an injection speed of 5.8 mm/s (which equals 100 μL/s in this case).

The measurement was started and was automatically aborted when the plunger rod reached the bottom of the syringe (syringe is empty) or a force higher than 50 N was reached during the measurement.

Table 5 shows the maximum injection forces for different conjugate concentrations with different mixing ratios of soluble HA (sHA).

TABLE 5

| Conjugate [mg/mL] | No sHA | 50:50 | 40:60 | 30:70 | 20:80 | 10:90 |
|---|---|---|---|---|---|---|
| | | 600 kD sHA:conjugate mixing ratio/ sHA 20 mg/mL | | | | |
| 20 | 10.5 N | 10 N | 11.7 N | 11.9 N | 11.2 N | 10.3 N |
| 25 | 13.6 N | — | — | — | — | — |
| 30 | 16.6 N | 12.3 N | 12.1 N | 12.4 N | 12.6 N | 12.6 N |
| | | 2600 kD sHA:conjugate mixing ratio/ sHA 20 mg/mL | | | | |
| 30 | | 15.5 N | 14.5 N | 16.1 N | 14.2 N | 18.5 N |

The injection forces of pure 20 mg/mL 600 kDa sHA solution was 13.3 N and of 2600 kDa sHA: 18.8 N.

---

The invention claimed is:

1. A prodrug or a pharmaceutically acceptable salt thereof comprising a drug linker conjugate of formula (I)

$$Z-L^1-L^2-L-Y—R^{20} \quad (I)$$

wherein Y is a peptide moiety having the formula (II)

(II)
His-X2-X3-Gly-Thr-Phe-Thr-Ser-Asp-Leu-Ser-Lys-Gln-

Leu-Asp-Glu-Gln-X18-Ala-X20-X21-Phe-Ile-Glu-Trp-

Leu-Ile-X28-Gly-Gly-Pro-X32-Ser-Gly-Ala-Pro-Pro-

Pro-Ser

X2 represents an amino acid residue selected from Ser, D-Ser and Aib,
X3 represents an amino acid residue selected from Gln and His,
X18 represents an amino acid residue selected from Arg and Lys
X20 represents an amino acid residue selected from Lys, Gln and His,
X21 represents an amino acid residue selected from Asp and Glu,
X28 represents an amino acid residue selected from Ser and Ala,
X32 represents an amino acid residue selected from Ser and Val,
or wherein Y is a peptide moiety having the formula (III)

(III)
His-X2-X3-Gly-Thr-Phe-Thr-Ser-Asp-Leu-Ser-Lys-Gln-

Leu-Asp-Glu-Gln-X18-Ala-X20-X21-Phe-Ile-Glu-Trp-

Leu-Ile-X28-Gly-Gly-Pro-X32-Ser-Gly-Ala-Pro-Pro-

Pro-Ser

X2 represents an amino acid residue selected from Ser, D-Ser and Aib,
X3 represents an amino acid residue selected from Gln and His,
X18 represents an amino acid residue selected from Leu and His
X20 represents an amino acid residue selected from His, Arg, Lys, and Gln,
X21 represents an amino acid residue selected from Asp and Glu,
X28 represents an amino acid residue selected from Lys, Ser and Ala,
X32 represents an amino acid residue selected from Ser and Val, or
wherein Y is a peptide moiety having the formula (IV)

(IV)
His-X2-X3-Gly-Thr-Phe-Thr-Ser-Asp-Leu-Ser-Lys-Leu-

Leu-Asp-Glu-Gln-X18-Ala-Lys-Asp-Phe-Ile-Glu-Trp-

Leu-Ile-Ala-Gly-Gly-Pro-X32-Ser-Gly-Ala-Pro-Pro-

Pro-Ser

X2 represents an amino acid residue selected from Ser, D-Ser and Aib,
X3 represents an amino acid residue selected from Gln and His,
X18 represents an amino acid residue selected from Arg and Leu,
X32 represents an amino acid residue selected from Ser and Val,
or
wherein Y is a peptide moiety having the formula (IVa)

(IVa)
H₂N-His-Aib-His-Gly-Thr-Phe-Thr-Ser-Asp-Leu-Ser-

Lys-Gln-Leu-X15-Glu-Gln-Leu-Ala-Arg-Asp-Phe-Ile-

Glu-Trp-Leu-Ile-Bal-X29-Gly-X31-X32-Ser-X34-X35-

Pro-Pro-Pro-X39

X15 represents an amino acid residue selected from Asp and Glu,
X29 represents an amino acid residue selected from Gly, D-Ala and Pro,
X31 represents an amino acid residue selected from Pro, His and Trp,
X32 represents an amino acid residue selected from Ser, His, Pro and Arg,
X34 represents an amino acid residue selected from Gly and D-Ala,
X35 represents an amino acid residue selected from Ala, Pro and Lys,
X39 represents Ser or Pro-Pro-Pro, or
wherein Y is a peptide moiety having the formula (IVb)

H$_2$N-His-Aib-Gln-Gly-Thr-Phe-Thr-Ser-Asp-Leu-Ser-Lys-Leu-Leu-Glu-Glu-Gln-Arg-Ala-Arg-Glu-Phe-Ile-Glu-Trp-Leu-Ile-Bal-D-Ala-Gly-Pro-Pro-Ser-D-Ala-Ala-Pro-Pro-Pro-Ser;

or a salt or solvate thereof;
R$^{20}$ is OH or NH$_2$;
L is a linker of formula (Ia),

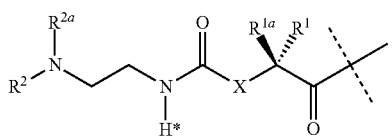
Ia wherein the dashed line indicates the attachment to the N-Terminus of Y by forming an amide bond;
X is C(R$^4$R$^{4a}$); N(R$^4$);
R$^1$, R$^{1a}$, are independently selected from the group consisting of H; and C$_{1-4}$ alkyl;
R$^2$, R$^{2a}$, are independently selected from the group consisting of H; and C$_{1-4}$ alkyl;
R$^4$, R$^{4a}$, are independently selected from the group consisting of H; and C$_{1-4}$ alkyl;
wherein R$^2$, R$^{2a}$, R$^4$ or R$^{4a}$ is substituted with one group L$^2$-L$^1$-Z; wherein
L$^2$ is a single chemical bond or is a C$_{1-20}$ alkyl chain, which is optionally interrupted by one or more groups independently selected from —O— and C(O)N(R$^{3aa}$) and is optionally substituted with one or more groups independently selected from OH and C(O)N(R$^{3aa}$R$^{3aaa}$), wherein R$^{3aa}$ and R$^{3aaa}$ are independently selected from the group consisting of H and C$_{1-4}$ alkyl; and
L$^2$ is attached to L$^1$ via a terminal group selected from the group consisting of

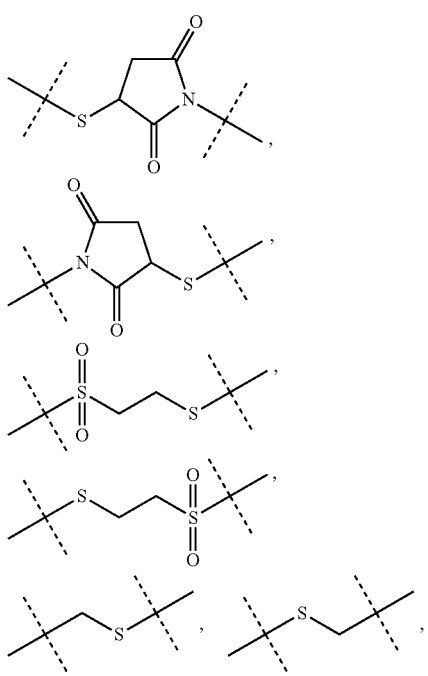

wherein L$^2$ is attached to the one position indicated with the dashed line
and L$^1$ is attached to the position indicated with the other dashed line; and
L$^1$ is a C$_{1-20}$ alkyl chain, which is optionally interrupted by one or more groups independently selected from —O— and C(O)N(R$^{5aa}$) and is optionally substituted with one or more groups independently selected from OH and C(O)N(R$^{5aa}$R$^{5aaa}$), wherein R$^{5aa}$ and R$^{5aaa}$ are independently selected from the group consisting of H and C$_{1-4}$ alkyl; and
L$^1$ is attached to Z via a terminal amino group forming an amide bond with the carboxy group of the beta-1,3-D-glucuronic acid of the hyaluronic acid of Z;
Z is a crosslinked hyaluronic acid hydrogel, in which 0.05 to 20% of the monomeric disaccharide units are crosslinked by a crosslinker; and 0.2 to 8.5% of the monomeric disaccharide units bear L$^1$-L$^2$-L-Y—R$^{20}$ groups.

2. A prodrug or a pharmaceutically acceptable salt thereof comprising a drug linker conjugate of formula (I) as claimed in claim 1

$$Z\text{-}L^1\text{-}L^2\text{-}Y\text{—}R^{20} \qquad (I)$$

wherein Y is a peptide moiety having the formula (II)

(II)
His-X2-X3-Gly-Thr-Phe-Thr-Ser-Asp-Leu-Ser-Lys-Gln-Leu-Asp-Glu-Gln-X18-Ala-X20-X21-Phe-Ile-Glu-Trp-Leu-Ile-X28-Gly-Gly-Pro-X32-Ser-Gly-Ala-Pro-Pro-Pro-Ser

X2 represents an amino acid residue selected from Ser, D-Ser and Aib,
X3 represents an amino acid residue selected from Gln and His, X18 represents an amino acid residue selected from Arg and Lys X20 represents an amino acid residue selected from Lys, Gln and His, X21 represents an amino acid residue selected from Asp and Glu, X28 represents an amino acid residue selected from Ser and Ala, X32 represents an amino acid residue selected from Ser and Val, or wherein Y is a peptide moiety having the formula (III)

(III)
His-X2-X3-Gly-Thr-Phe-Thr-Ser-Asp-Leu-Ser-Lys-Gln-Leu-Asp-Glu-Gln-X18-Ala-X20-X21-Phe-Ile-Glu-Trp-Leu-Ile-X28-Gly-Gly-Pro-X32-Ser-Gly-Ala-Pro-Pro-Pro-Ser

X2 represents an amino acid residue selected from Ser, D-Ser and Aib,

X3 represents an amino acid residue selected from Gln and His,

X18 represents an amino acid residue selected from Leu and His

X20 represents an amino acid residue selected from His, Arg, Lys, and Gln,

X21 represents an amino acid residue selected from Asp and Glu,

X28 represents an amino acid residue selected from Lys, Ser and Ala,

X32 represents an amino acid residue selected from Ser and Val, or wherein Y is a peptide moiety having the formula (IV)

(IV)
His-X2-X3-Gly-Thr-Phe-Thr-Ser-Asp-Leu-Ser-Lys-Leu-Leu-Asp-Glu-Gln-X18-Ala-Lys-Asp-Phe-Ile-Glu-Trp-Leu-Ile-Ala-Gly-Gly-Pro-X32-Ser-Gly-Ala-Pro-Pro-Pro-Ser

X2 represents an amino acid residue selected from Ser, D-Ser and Aib,

X3 represents an amino acid residue selected from Gln and His,

X18 represents an amino acid residue selected from Arg and Leu,

X32 represents an amino acid residue selected from Ser and Val, or a salt or solvate thereof;

$R^{20}$ is OH or $NH_2$;

L is a linker of formula (Ia),

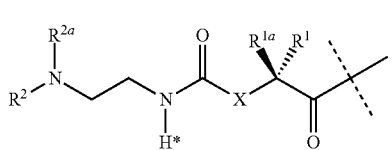

wherein the dashed line indicates the attachment to the N-Terminus of Y by forming an amide bond;

X is $C(R^4R^{4a})$; $N(R^4)$;

$R^1$, $R^{1a}$, are independently selected from the group consisting of H; and $C_{1-4}$ alkyl;

$R^2$, $R^{2a}$, are independently selected from the group consisting of H; and $C_{1-4}$ alkyl;

$R^4$, $R^{4a}$, are independently selected from the group consisting of H; and $C_{1-4}$ alkyl;

wherein $R^2$, $R^{2a}$, $R^4$ or $R^{4a}$ is substituted with one group $L^2$-$L^1$-Z; wherein $L^2$ is a single chemical bond or is a $C_{1-20}$ alkyl chain, which is optionally interrupted by one or more groups independently selected from —O— and $C(O)N(R^{3aa})$ and is optionally substituted with one or more groups independently selected from OH and $C(O)N(R^{3aa}R^{3aaa})$, wherein $R^{3aa}$ and $R^{3aaa}$ are independently selected from the group consisting of H and $C_{1-4}$ alkyl; and $L^2$ is attached to $L^1$ via a terminal group selected from the group consisting of

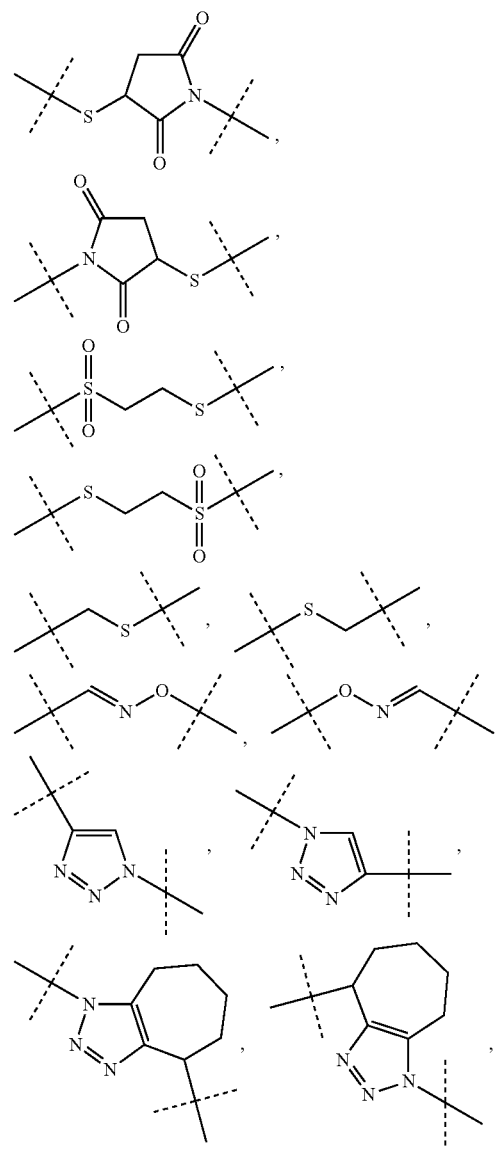

-continued

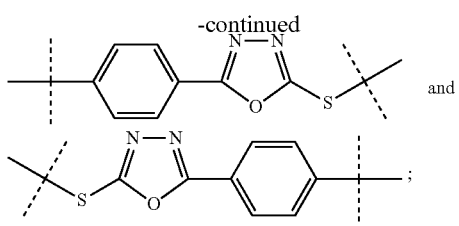

and wherein $L^2$ is attached to the one position indicated with the dashed line
and $L^1$ is attached to the position indicated with the other dashed line; and
$L^1$ is a $C_{1-20}$ alkyl chain, which is optionally interrupted by one or more groups independently selected from —O— and $C(O)N(R^{5aa})$ and is optionally substituted with one or more groups independently selected from OH and $C(O)N(R^{5aa}R^{5aaa})$, wherein $R^{5aa}$ and $R^{5aaa}$ are independently selected from the group consisting of H and $C_{1-4}$ alkyl; and
$L^1$ is attached to Z via a terminal amino group forming an amide bond with the carboxy group of the beta-1,3-D-glucuronic acid of the hyaluronic acid of Z;
Z is a crosslinked hyaluronic acid hydrogel, in which 0.05 to 20% of the monomeric disaccharide units are crosslinked by a crosslinker; and 0.2 to 8.5% of the monomeric disaccharide units bear $L^1$-$L^2$-L-Y—$R^{20}$ groups.

3. The prodrug of claim 1, wherein
L is a linker moiety of formula (Ib),

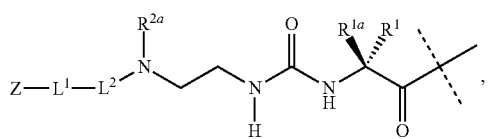
(Ib)

wherein the dashed line indicates attachment to Y by forming an amide bond;
$R^1$, $R^{1a}$, $R^{2a}$ are selected independently from the group consisting of H and $C_{1-4}$ alkyl;
$L^2$-$L^2$-Z is defined as in claim 1.

4. The prodrug of claim 1, wherein
L is a linker moiety -L of formula (Ic),

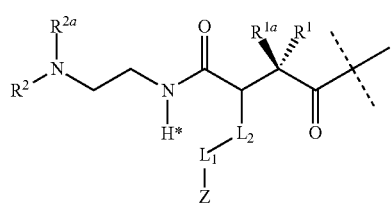
(Ic)

wherein the dashed line indicates attachment to Y by forming an amide bond;
$R^1$ and $R^{1a}$ are H;
$R^2$, $R^{2a}$ are independently selected from the group consisting of H and $CH_3$;
wherein $L^2$-$L^1$-Z is defined as in claim 1.

5. The prodrug of claim 1, wherein
$L^2$ is a $C_{1-6}$ alkyl chain, which is optionally interrupted by one group selected from —O— and $C(O)N(R^{3aa})$ and, wherein $R^{3aa}$ is independently selected from the group consisting of H and $C_{1-4}$ alkyl; and
$L^2$ is attached to $L^1$ via a terminal group selected from the group consisting of

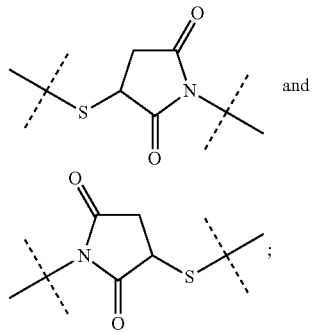

and

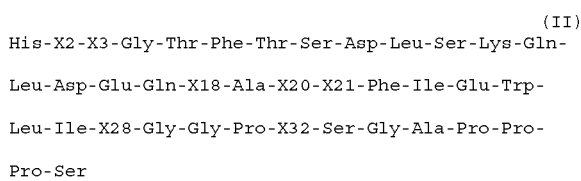

wherein $L^2$ is attached to the one position indicated with the dashed line and $L^1$ is attached to the position indicated with the other dashed line.

6. The prodrug of claim 1,
wherein Y is a peptide moiety having the formula (II)

(II)
His-X2-X3-Gly-Thr-Phe-Thr-Ser-Asp-Leu-Ser-Lys-Gln-

Leu-Asp-Glu-Gln-X18-Ala-X20-X21-Phe-Ile-Glu-Trp-

Leu-Ile-X28-Gly-Gly-Pro-X32-Ser-Gly-Ala-Pro-Pro-

Pro-Ser wherein
X2 represents an D-Ser
X3 represents His,
X18 represents Arg
X20 represents Lys,
X21 represents an amino acid residue selected from Asp and Glu,
X28 represents an amino acid residue selected from Ser and Ala,
X32 represents an amino acid residue selected from Ser and Val;
or wherein Y is a peptide moiety having the formula (III)

(III)
His-X2-X3-Gly-Thr-Phe-Thr-Ser-Asp-Leu-Ser-Lys-Gln-

Leu-Asp-Glu-Gln-X18-Ala-X20-X21-Phe-Ile-Glu-Trp-

Leu-Ile-X28-Gly-Gly-Pro-X32-Ser-Gly-Ala-Pro-Pro-

Pro-Ser wherein
X2 represents Aib,
X3 represents His,
X18 represents Leu,
X20 represents Lys,
X21 represents an amino acid residue selected from Asp and Glu,
X28 represents an amino acid residue selected from Ser and Ala, X32 represents an amino acid residue selected from Ser and Val.

7. The prodrug of claim 1, wherein Y is a peptide moiety having the formula (IVa)

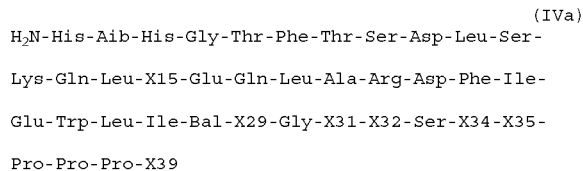

(IVa)
H₂N-His-Aib-His-Gly-Thr-Phe-Thr-Ser-Asp-Leu-Ser-Lys-Gln-Leu-X15-Glu-Gln-Leu-Ala-Arg-Asp-Phe-Ile-Glu-Trp-Leu-Ile-Bal-X29-Gly-X31-X32-Ser-X34-X35-Pro-Pro-Pro-X39

X15 represents an amino acid residue selected from Asp and Glu,
X29 represents an amino acid residue selected from Gly, D-Ala and Pro,
X31 represents an amino acid residue selected from Pro, His and Trp,
X32 represents an amino acid residue selected from Ser, His, Pro and Arg,
X34 represents an amino acid residue selected from Gly and D-Ala,
X35 represents an amino acid residue selected from Ala, Pro and Lys,
X39 represents Ser or Pro-Pro-Pro.

8. The prodrug of claim 1, wherein Y is a peptide moiety having the formula (IVb)

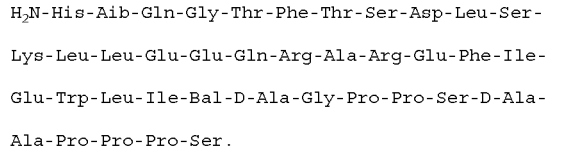

H₂N-His-Aib-Gln-Gly-Thr-Phe-Thr-Ser-Asp-Leu-Ser-Lys-Leu-Leu-Glu-Glu-Gln-Arg-Ala-Arg-Glu-Phe-Ile-Glu-Trp-Leu-Ile-Bal-D-Ala-Gly-Pro-Pro-Ser-D-Ala-Ala-Pro-Pro-Pro-Ser.

9. The prodrug of claim 1, wherein Y—R²⁰ is a GLP-1/Glucagon agonist selected from the group consisting of SEQ ID NOs: 4 to 60.

10. A pharmaceutical composition comprising a prodrug of claim 1 or a pharmaceutical salt thereof together with at least one pharmaceutically acceptable excipient.

11. A pharmaceutical composition comprising a prodrug of claim 1 or a pharmaceutical salt thereof together with at least one pharmaceutically acceptable excipient and a viscosity modifier.

12. A pharmaceutical composition as claimed in claim 11, wherein the viscosity modifier is hyaluronic acid.

13. A pharmaceutical composition as claimed in claim 10 in the form of an injectable formulation.

14. A pharmaceutical composition as claimed in claim 10 in the form of a suspension.

15. A pharmaceutical composition as claimed in claim 10 in the form of a suspension, wherein the prodrug has a concentration of 0.5 to 8 weight/volume percent.

16. A pharmaceutical composition as claimed in claim 10 in the form of a suspension, wherein the prodrug has a concentration of 1.5 to 3 weight/volume percent.

17. A composition according to claim 10, wherein the prodrug is sufficiently dosed in the composition to provide a therapeutically effective amount of GLP1/Glucagon agonist for at least 6 days in one application.

18. A composition according to claim 10, wherein the composition is a single dose composition.

19. A method of treating diseases or disorders which can be treated by GLP-1/Glucagon agonist, comprising administering to a patient in need thereof an effective amount of the prodrug of claim 1.

20. A method of treating diabetes, comprising administering to a patient in need thereof an effective amount of the prodrug of claim 1.

21. A method of treating dyslipdemia, comprising administering to a patient in need thereof an effective amount of the prodrug of claim 1.

22. A method of treating metabolic syndrome, comprising administering to a patient in need thereof an effective amount of the prodrug of claim 1.

23. A method of treating hepatosteatosis, comprising administering to a patient in need thereof an effective amount of the prodrug of claim 1.

24. A GLP-1/Glucagon agonist-linker conjugate intermediate of formula (VIII)

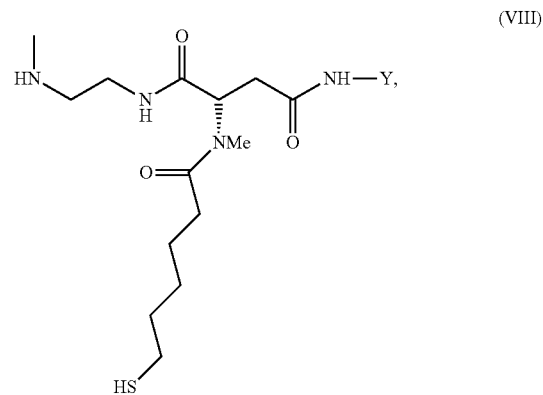

wherein Y is a peptide of Seq ID 4 to 60.

25. An GLP-1/Glucagon agonist-linker conjugate intermediate of formula (IX)

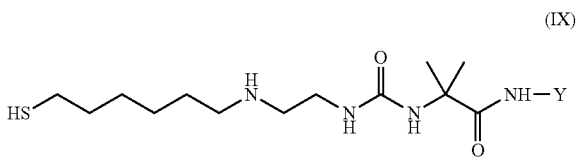

wherein Y is a peptide selected from the group consisting of SEQ ID NOs: 4 to 60.

26. An GLP-1/Glucagon agonist-linker conjugate intermediate of formula (X)

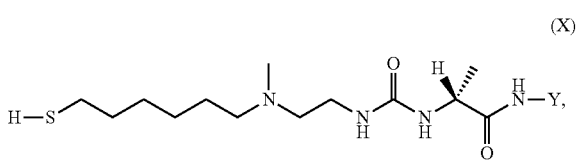

wherein Y is a peptide selected from the group consisting of SEQ ID NOs: 4 to 60.

27. The composition of claim 18, wherein the prodrug is in the form of a suspension, and wherein the prodrug suspension can be administered by injection through a needle smaller than 0.26 mm inner diameter.

28. A method of treating non-alcoholic liver-disease (NAFLD) or non-alcoholic steatohepatitis (NASH), comprising administering to a patient in need thereof an effective amount of the prodrug of claim 1.

\* \* \* \* \*